US009499803B2

(12) United States Patent
Tang et al.

(10) Patent No.: US 9,499,803 B2
(45) Date of Patent: *Nov. 22, 2016

(54) VARIANT LOVD POLYPEPTIDE

(71) Applicant: The Regents of the University of California, Oakland, CA (US)

(72) Inventors: Yi Tang, San Gabriel, CA (US); Xue Gao, Los Angeles, CA (US); Xinkai Xie, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/615,792

(22) Filed: Feb. 6, 2015

(65) Prior Publication Data

US 2015/0218531 A1 Aug. 6, 2015

Related U.S. Application Data

(63) Continuation-in-part of application No. 13/499,356, filed as application No. PCT/US2010/052038 on Oct. 8, 2010, now Pat. No. 8,981,056.

(60) Provisional application No. 61/249,894, filed on Oct. 8, 2009.

(51) Int. Cl.
*A61K 38/00* (2006.01)
*C12N 9/10* (2006.01)

(52) U.S. Cl.
CPC ......... *C12N 9/1029* (2013.01); *C07K 2319/00* (2013.01)

(58) Field of Classification Search
None
See application file for complete search history.

(56) References Cited

U.S. PATENT DOCUMENTS

| 6,391,583 | B1 | 5/2002 | Hutchinson et al. | |
|---|---|---|---|---|
| 8,981,056 | B2 * | 3/2015 | Tang | C12N 9/1029 435/6.1 |
| 2009/0191602 | A1 | 7/2009 | Tang et al. | |

FOREIGN PATENT DOCUMENTS

| WO | 0037629 | 6/2000 |
|---|---|---|
| WO | 03010324 | 2/2003 |
| WO | WO03/010324 | 2/2003 |
| WO | 2007147801 | 12/2007 |
| WO | 2009077523 | 6/2009 |
| WO | 2011041231 | 4/2011 |

OTHER PUBLICATIONS

European Office Action dated Oct. 15, 2013 for European Patent Application No. 10822785.1.
Database UniProt [Online] Oct. 17, 2006, "Sub-Name: Full=Putative uncharacterized protein;" retrieved from EBI accession No. UNIPROT:Q0C8M0 Database accession No. Q0C8M0.
Database Genesq [Online] May 26, 2011, "Aspergillus terreus mutant LovD acyltransferase sequence, SEQ ID 60.", retrieved from EBI accession No. GSP:AZH26666 Database accession No. AZH26666.
Chinese Office Action (with English translation) dated Aug. 5, 2013 for Chinese Patent Application No. 201080055195.X.
European Search Report dated Feb. 26, 2013, Application No. 10822785.1.
Abe, Y., et al., "Molecular cloning and characterization of an ML-236B (compactin) biosynthetic gene cluster in Penicillium citrinum", Molecular Genetics and Genomics (2002) 267, pp. 636-646, XP-002472854.
Abe, Y., et al., "Effect of increased dosage of the ML-236B (compactin) biosynthetic gene cluster on ML-236B production in Penicillium citrinum", Molecular Genetics and Genomics (2002) 268, pp. 130-137, XP-002400771.
Abe, Y., et al., "Subname: Ful=Transesterase", Mar. 1, 2003, XP-002691905, retrieved from EBI accession No. UNIPROT:Q8J0G0.
Gao, Xue, et al., Supplemental Data—Directed Evolution and Structural Characterization of a Simvastatin Synthase, Chemistry & Biology 16, Oct. 30, 2009, nine (9) pages, XP55052867.
Klaassen, P., et al, "Monascus pilosus esterase sequence, SEQ 51", Jul. 23, 2009, XP002691903, retrieved from EBI accession No. GSP: AXB24807.
Klaassen, P., et al., "Penicillium citrinum esterase sequence, SEQ 49", Jul. 23, 2009, XP002691904, retrieved from EBI accession No. GSP: AXB24805.
Xie et al., "Biosynthesis of Lovastatin Analogs with a Broadly Specific Acyltransferase Chemistry & Biology 13", 1161-1169, Nov. 2006.
Kennedy, J., et al., "Modulation of Polyketide Synthase Activity by Accessory Proteins During Lovastatin Biosynthesis", Science, American Association for the Advancement of Science, Washington, D.C; US, vol. 284, No. 5418, Jan. 1, 1999, pp. 1368-1372, XP000914559 ISSN: 0036-8075 DOI:10.1126/ SCIENCE.284. 5418.1368.
European Search Report dated Nov. 17, 2010, Application No. 07777257.2.
CN Office Action dated May 25, 2011 (CN application No. 200780027455.0) with translation.
GenBank: Q8FCT4 dated Sep. 13, 2005.
Sorensen, J. L., et al., "Transformations of cycilc nonaketides by Aspergillus terreus mutants blocked for lovastatin biosynthesis at the lovA and lovC genes", Org Biomol Chem, 1(1):50-59, Nov. 21, 2002.
Guo et al., "Protein tolerance to random amino acid change". 2004, Proc. Natl. Acad. Sci USA 101: 9205-9210.
Lazar et al., "Transforming Growth Factor Alpha: Mutation of Aspartic Acid 47 and Leucine 48 Results in Different Biological Activity". 1988, Mol. Cell. Biol. 8: 1247-1252.

(Continued)

*Primary Examiner* — Hope Robinson
(74) *Attorney, Agent, or Firm* — Gates & Cooper LLP

(57) ABSTRACT

The invention disclosed herein relates to methods and materials for producing simvastatin and related compounds such as huvastatin. In particular, the disclosure teaches that variants of the LovD acyltransferase polypeptide can be engineered to exhibit properties that facilitate their use in the production of simvastatin and/or huvastatin. The materials and processes disclosed herein are designed so that fermentation facilities currently producing lovastatin can be converted to producing simvastatin and related compounds with minimal modifications.

10 Claims, 28 Drawing Sheets

(56) References Cited

OTHER PUBLICATIONS

Hill et al., Functional Analysis of conserved Histidines in ADP-Glucose Pyrophosphorylase from *Escherichia coli*, 1998, Biochem. Biophys. Res. Comm. 244:573-577.

Wacey et al., "Disentangling the perturbational effects of amino acid substitutions in the DNA-binding domain of p53". Hum Genet, 1999, vol. 104, pp. 15-22.

PCT International Search Report dated Apr. 7, 2011 for PCT/US2010/52038.

Gao et al., "Directed Evolution and Structural Characterization of a Simvastatin Synthase", Chem. Biol., Oct. 30, 2009; 16(10): 1064-1074 doi: 10.1016/j.chembiol.2009.09.017.

Xie et al., "Efficient Synthesis of Simvastatin by Use of Whole-Cell Biocatalysis", Applied and Environmental Microbiology, Apr. 2007, p. 2054-2060, American Society for Microbiology.

Xie et al., "Rational Improvement of Simvastatin Synthase Solubility in Escherichia coli Leads to Higher Whole-Cell Biocatalytic Activity", Biotechnology and Bioengineering, vol. 102, No. 1, Jan. 1, 2009.

Chinese Office Action dated May 25, 2011, Appln. No. 200780027455.0.

Sorensen et al., "Transformations of cyclic nonaketides by Aspergillus terreus mutants blocked for lovastatin biosynthesis at the lovA and lovC", Org. Biomol. Chem., 2003, 1, 50-59, published Feb. 6, 2002.

GenBank: Q8FCT4, "RecName: Full=Carboxylesterase BioH; AltName: Full=Biotin synthesis", published Sep. 13, 2005.

\* cited by examiner

FIG. 13

FIG. 13: Amino acid substitutions and characterization of LovD variants

| | Mutations | Whole cell Activity* | $k_{cat}$ (min⁻¹) | $K_M$ of MJA (mM)† | $K_M$ of DMB-SMMP (mM)‡ | Soluble protein (mg/L)§ | $T_m$(°C)¶ |
|---|---|---|---|---|---|---|---|
| G0 | | 1 | 0.66±0.03 | 0.77±0.17 | 0.67±0.12 | 138±11 | 39.5±0.4 |
| G1 | A86V | 1.2 | 0.79±0.03 | 0.74±0.16 | 0.66±0.19 | 140±5.4 | 41±0.7 |
| G2.1 | A86V D12G G275S | 1.9 | 1.14±0.03 | 0.91±0.17 | 0.62±0.10 | 184±8.7 | 40.5±0.4 |
| G2.2 | A86V A190T | 1.8 | 1.20±0.09 | 0.74±0.21 | 0.69±0.17 | 168±17 | 41±0.4 |
| G3 | A86V D12G A190T G275S | 3.6 | 1.86±0.09 | 0.77±0.11 | 0.70±0.19 | 205±23 | 41±0.4 |
| G4.1 | A86V D12G A190T G275S A10V K26E | 4.8 | 2.13±0.03 | 0.70±0.24 | 0.66±0.16 | 183±18 | 43.5±0.7 |
| G4.2 | A86V D12G A190T G275S H161Y K227R | 5.2 | 2.16±0.12 | 0.80±0.24 | 0.64±0.16 | 221±9.3 | 42.5±1.9 |
| G5 | A86V D12G A190T G275S K26E H161Y | 6.4 | 2.61±0.03 | 0.74±0.03 | 0.69±0.14 | 206±5.7 | 46.5±0.4 |
| G6 | A86V D12G A190T G275S K26E H161Y V334D L361M | 9.3 | 3.30±0.06 | 0.70±0.07 | 0.63±0.15 | 212±3.9 | 47±0.1 |
| G7 | A86V D12G A190T G275S K26E H161Y V334F | 11.2 | 4.80±0.06 | 0.70±0.04 | 0.69±0.17 | 214±6.3 | 48.5±0.7 |

FIG. 20: Statistics of X-ray data collection and atomic refinement (numbers in parentheses refer to the outer shell of data).

| Protein | G0 | SeMet G0 | G5 | G5 | G5' | G5' | G5' |
|---|---|---|---|---|---|---|---|
| Ligand | none | none | none | MJA | MJA | SVA | LVA |
| Data collection | | | | | | | |
| Space group | P1 | C2 | P2₁2₁2₁ | P2₁2₁2₁ | P2₁2₁2₁ | P2₁2₁2₁ | P2₁2₁2₁ |
| Cell dimensions | | | | | | | |
| $a, b, c$ (Å) | 56.7,79.7,104.1 | 209.5,85.2,210.4.0 | 58.2, 75.0, 131.6 | 58.5, 75.2, 133.5 | 58.0, 75.2, 132.7 | 58.5, 75.1, 131.8 | 59.0, 75.2, 131.7 |
| α, β, γ (°) | 94.1,91.6,106.8 | 90.0,117.5,90.0 | 90.0, 90.0, 90.0 | 90.0, 90.0, 90.0 | 90.0, 90.0, 90.0 | 90.0, 90.0, 90.0 | 90.0, 90.0, 90.0 |
| protomers/asymmetric unit | 4 | 4 | 1 | 1 | 1 | 1 | 1 |
| Resolution (Å) | 100.00-3.40 (3.66-3.40) | 80.00-2.50 (2.59-2.50) | 90.00-2.00 (2.07-2.00) | 60.00-2.00 (2.07-2.00) | 60.00-2.05 (2.12-2.05) | 60.00-2.00 (2.07-2.00) | 60.00-2.00 (2.07-2.00) |
| $R_{merge}$ (%) | 20.8 (43.4) | 11.8 (45.3) | 4.9 (37.8) | 15.6 (39.6) | 6.8 (40.2) | 6.9 (31.4) | 11.8 (39.6) |
| $I/\sigma I$ | 5.1 (2.9) | 10.2 (1.7) | 47.2 (6.5) | 13.0 (4.8) | 38.3 (6.6) | 19.5 (3.9) | 13.33 (4.64) |
| Completeness (%) | 99.3 (98.9) | 89.9 (46.7) | 99.9 (100.0) | 99.8 (100.0) | 99.9 (99.8) | 97.7 (99.6) | 98.5 (99.5) |
| Redundancy | 3.7 (3.7) | 5.3 (3.0) | 11.6 (11.7) | 6.2 (6.4) | 15.4 (12.9) | 4.9 (4.9) | 6.4 (6.5) |
| wavelength (Å) | 0.9793 | 0.9793 | 0.9794 | 0.9794 | 0.9792 &1.5418 | 0.9717 | 0.9795 |
| Refinement | | | | | | | |
| Resolution (Å) | 103.7- 3.4 (3.5- 3.4) | 65.9- 2.50 (2.56-2.50) | 65.80- 2.00 (2.05- 2.00) | 46.18- 2.00 (2.05- 2.00) | 49.86- 2.05 (2.10- 2.05) | 49.51- 2.00 (2.05- 2.00) | 46.42- 2.00 (2.06- 2.00) |
| No. reflections | 22457 (1669) | 47728 (1657) | 37539 (2837) | 38325 (2910) | 35223 (2686) | 36938 (2714) | 37005 (2671) |
| $R_{work} / R_{free}$ (%) | 23.1/27.5 (31.9/35.5) | 24.8/29.0 (35.6/40.5) | 17.9/20.6 (20.4/24.4) | 17.9/21.3 (21.5/26.1) | 17.7/20.9 (19.8/23.7) | 17.6/20.9 (23.1/25.1) | 16.2/18.9 (18.3/21.8) |
| No. atoms | | | | | | | |

| | | | | | | |
|---|---|---|---|---|---|---|
| Protein | 12328 | 12547 | 3289 | 3332 | 3355 | 3351 | 3343 |
| Ligand/ion 1 | 0 | 65 (sulfate) | 13 (PEG) | 48 (MJA) | 24 (MJA) | 31(SVA) | 30 |
| Ligand/ion 2 | 0 | 0 | 6 (glycerol) | 12 (formate) | 8 (dithiothreitol) | 0 | 0 |
| Water | 0 | 21 | 151 | 275 | 157 | 179 | 230 |
| B-factors (Å$^2$) | | | | | | | |
| Protein | 6.3 | 51.7 | 34.4 | 27.6 | 35.4 | 32.2 | 31.4 |
| Ligand/ion 1 | n/a | 68.0 (SO$_4$) | 58.6 (PEG) | 58.8 (MJA) | 46.5 (MJA) | 45.5 (SVA) | 38.3 (LVA) |
| Ligand/ion 1 | n/a | n/a | 58.2 (glycerol) | 38.6 (formate) | 74.2 (dithiothreitol) | n/a | n/a |
| Water | n/a | 39.4 | 36.9 | 32.8 | 37.6 | 36.1 | 37.2 |
| R.M.S. deviations | | | | | | | |
| Bond lengths (Å) | 0.011 | 0.006 | 0.009 | 0.009 | 0.008 | 0.008 | 0.008 |
| Bond angles (°) | 1.3 | 0.995 | 1.199 | 1.230 | 1.202 | 1.193 | 1.193 |
| Ramachandran Plot (%) | | | | | | | |
| most favored | 88.0 | 90.0 | 91.2 | 89.4 | 89.7 | 90.3 | 90.6 |
| additionally allowed | 11.4 | 9.7 | 8.5 | 10.3 | 10.0 | 9.4 | 9.1 |
| generously allowed | 0.6 | 0.3 | 0.3 | 0.3 | 0.3 | 0.3 | 0.3 |
| disallowed | 0.0 | 0.0 | 0.0 | 0.0 | 0.0 | 0.0 | 0.0 |
| PDB ID code | 3HL9 | 3HLB | 3HLC | 3HLD | 3HLE | 3HLF | 3HLG |

FIG. 20 (Continued)

VARIANT LOVD POLYPEPTIDE

CROSS REFERENCE TO RELATED APPLICATIONS

This application is a continuation application that claims the benefit under 35 U.S.C. §120 of U.S. patent application Ser. No. 13/499,356, filed Mar. 30, 2012, now U.S. Pat. No. 8,981,056, which is the National Stage International Application No. PCT/US10/52038 (International Publication No. WO2011/044496), filed Oct. 8, 2010, which claims priority under Section 119(e) from U.S. Provisional Application Ser. No. 61/249,894 filed Oct. 8, 2009, the contents of which are incorporated herein by reference. This application is related to International Application No. PCT/US2007/012362 (International Publication No. WO 2007/139871), the contents of which are incorporated herein by reference.

STATEMENT OF GOVERNMENT SUPPORT

This invention was made with Government support under R21 HL091197, awarded by the National Institutes of Health. The Government has certain rights in this invention.

FIELD OF THE INVENTION

The invention relates to methods and materials for biosynthesizing compounds such as simvastatin including procedures using microbial hosts.

BACKGROUND OF THE INVENTION

Simvastatin is a semisynthetic derivative of the natural product lovastatin, which can be isolated from the fermentation broth of *Aspergillus terreus*. Both lovastatin and simvastatin are cholesterol lowering drugs that substantially lower the risk of heart disease among adults. Lovastatin and simvastatin are marketed by Merck Co. as Mevacor and Zocor, respectively. Simvastatin is a more potent derivative of lovastatin and is the second best selling drug in the United States in 2005, with an expect sales of $4.5 billion in the US alone.

The gene cluster for lovastatin biosynthesis in *A. terreus* (see, e.g., J. Kennedy, K. et. al., *Science*, 1999, 284, 1368-1372; and C. R. Hutchinson, J. et. al., *Antonie Van Leeuwenhoek* 2000, 78, 287-295) has been described previously (see, e.g., U.S. Pat. No. 6,391,583, the contents of which are herein incorporated by reference). Encoded in the gene cluster is a 46 kD protein LovD, that was initially identified as an esterase homolog. Monacolin J, the immediate biosynthetic precursor of lovastatin, is assembled by the upstream megasynthase LovB (see, e.g., L. Hendrickson, C. R. et. al., *Chem. Biol.* 1999, 6, 429-439), (also known as lovastatin nonaketide synthase, LNKS), enoylreductase LovC and CYP450 oxygenases. The five carbon unit side chain is synthesized by LovF (lovastatin diketide synthase, LDKS) through condensation between an acetyl-CoA and a malonyl-CoA. The condensed diketide undergoes methylation and reductive tailoring by the individual LovF domains to yield an α-S-methylbutyryl thioester covalently attached to the phosphopantetheine arm on the acyl carrier protein (ACP) domain of LovF (see, e.g., J. Kennedy, K. et. al., *Science*, 1999, 284, 1368-1372 and C. R. Hutchinson, J. et. al., *Antonie Van Leeuwenhoek* 2000, 78, 287-295), and Lovastatin is subsequently produced from monacolin J. Inactivation of either LovD or LovF in *A. terreus* leads to accumulation of the precursor monacolin J (see, e.g., J. Kennedy, K. et. al., *Science*, 1999, 284, 1368-1372 and C. R. Hutchinson, J. et. al., *Antonie Van Leeuwenhoek* 2000, 78, 287-295).

Once lovastatin is produced via fermentation in an *A. terreus* host for example, simvastatin can be produced from lovastatin. Currently, simvastatin is a semisynthetic derivative of lovastatin. Lovastatin is obtained via fermentation of the *A. terreus* host. After purification of the compound, the semisynthesis can proceed as follows: 1) the 2-methylbutyrate side arm can be hydrolyzed in the presence of base to yield the intermediate monacolin J; 2) lactonize the free acid; 3) the alcohol functional group at C13 is protected with a protection group (such as tert-butyldimethylsilyl); 4) Esterification of the exposed C8 alcohol with an acyl substrate such as 2-dimethylbutyryl chloride to yield a C13 protected version of simvastatin, and 5) Deprotection of C13 OH to yield simvastatin.

Various multistep synthesis of simvastatin have been described previously (see, e.g., PCT WO 2005/066150 and U.S. Application Nos. 20050080275 and 20040068123, the contents of which are herein incorporated by reference). For example, a widely used process starts with the hydrolysis of the C8 ester in lovastatin to yield the triol monacolin J, followed by selective silylation of the C13 alcohol, esterification of C8 alcohol with dimethylbutyryl chloride and deprotection of C13 alcohol to yield simvastatin (see, e.g., W. F. Hoffman, et. al., *J. Med. Chem.* 1986, 29, 849-852). Enzymatic transformations using lipases and esterases have been investigated as alternatives to chemical derivation (see, e.g., PCT WO 2005/040107, PCT WO 94/26920 and T. G. Schimmel, et. al., *Appl. Environ. Microbiol.* 1997, 63, 1307-1311, the contents of which are herein incorporated by reference). However, the requirement of regioselective esterification invariably involves protection of other alcohol groups and often leads to lowered overall yield. Therefore, a specific reagent that is able to selectively acylate C8 of monacolin J is important towards the efficient synthesis of simvastatin and additional statin analogs.

Variations of the above schemes are common, however, most procedures will invariably involve isolation of lovastatin first, hydrolysis of the methylbutyrate side chain, protection of the free alcohol, reaction with an acyl substrate, and deprotection. Although the chemical transformations involved are relatively simple, they are inefficient and involve multiple steps and therefore contribute to the current high cost of manufacturing simvastatin ($3 per pill). For this reason, methods and materials that facilitate the cost effective manufacture of simvastatin and related compounds are highly desirable.

SUMMARY OF THE INVENTION

As disclosed in detail below, it is now possible to generate simvastatin and related compounds both in vitro or in vivo using variants of the LovD acyltransferase polypeptide that have been engineered to exhibit properties that facilitate their use in the production of simvastatin and/or huvastatin. The materials and processes disclosed herein are designed so that fermentation facilities currently producing lovastatin can be converted to producing simvastatin and related compounds with minimal modifications.

Embodiments of the present invention provide methods and materials designed to take advantage of biological processes by which lovastatin is made in order to produce the lovastatin derivative, simvastatin. The present invention also provides methods and materials designed to take advantage of biological processes by which lovastatin is made in order to produce related compounds such as the pravastatin derivative, huvastatin. Embodiments of the invention include materials and methods useful for generating simvastatin without the multiple chemical synthesis steps that are currently employed to generate this compound. Typical embodiments of the invention do not require the purification of lovastatin as a first step, followed by the further semi-synthetic procedures and instead combine variants of the LovD acyltransferase polypeptide with acyl thioester compounds in a fermentation process that results in the production of simvastatin and/or huvastatin.

The invention disclosed herein has a number of embodiments. An illustrative embodiment of the invention is a variant of a LovD polypeptide shown in SEQ ID NO:1, the variant LovD polypeptide comprising at least one specific amino acid substitution such as A10V; D12G; K26E; C40A; C60N; A86V; H161Y; A190T; K227R; G275S; V334D; V334F; and/or L361M. A related embodiment of the invention is a variant of a LovD polypeptide shown in SEQ ID NO:1, the variant LovD polypeptide comprising a set of amino acid substitutions, for example a set of at least three amino acid substitutions at amino acid residue positions C40 and C60; and at least one further substitution at amino acid residue position: A10; D12; K26; A86; A190; H161; K227; G275; V334; or L361. In such substitution variants of the LovD polypeptide, the amino acid substitution can comprise any one of the 19 amino acids not found at the amino acid residue position on the LovD polypeptide shown in SEQ ID NO:1. Typically, the substitution variant exhibits one or more altered properties as compared to the LovD polypeptide shown in SEQ ID NO:1, for example, a decreased aggregation; an improved thermal stability; an improved catalytic activity; an improved $k_{cat}/K_m$ value; an improved soluble expression level; and/or an improved whole cell activity at 25° C.

As noted above, certain embodiments of the invention include specific constellations of amino acid substitutions. For example, in some embodiments of the invention, the variant LovD polypeptide comprises amino acid substitutions at: amino acid residue positions C40; C60; and A86; or amino acid residue positions C40; C60; A86; and A190; or amino acid residue positions C40; C60; D12; A86; and G275; or amino acid residue positions C40; C60; D12; A86; C40; C60; A190; and G275; or amino acid residue positions C40; C60; D12; K26; A86; C40; C60; H161; A190; and G275; or amino acid residue positions C40; C60; D12; A86; A190; and G275; or amino acid residue positions C40; C60; A10; D12; K26; A86; A190; and G275; or amino acid residue positions C40; C60; D12; K26; A86; H161; A190; and G275; or amino acid residue positions C40; C60; D12; K26; A86; H161; A190; G275; V334 and L361; or amino acid residue positions C40; C60; D12; K26; A86; H161; A190; G275; and V334. Specific illustrative embodiments of these variants include those having amino acid substitutions: D12G, C40A, C60N, A86V, A190T and G275S; or D12G, K26E, C40A, C60N, A86V, H161Y, A190T and G275S; or D12G, K26E, C40A, C60N, A86V, H161Y, A190T; G275S and V334F.

Embodiments of the invention include polynucleotides encoding the substitution variants disclosed herein, for example an isolated polynucleotide having at least a 95%-100% sequence identity to a polynucleotide encoding a variant LovD polypeptide as disclosed herein. Related embodiments of the invention include a vector comprising these polynucleotides (e.g. an expression vector including control sequences recognized by a host cell transformed with the vector) as well as host cells comprising such vectors. Optionally, the host cell is an *Escherichia coli, Aspergillus terreus, Monascus ruber, Monascus purpureus, Monascus pilosus, Monascus vitreus, Monascus pubigerus, Candida cariosilognicola, Aspergillus oryzea, Doratomyces stemonitis, Paecilomyces virioti, Penicillum citrinum, Penicillin chrysogenum, Scopulariopsis brevicaulis, Neurospora crassa* or *Trichoderma viride*. A related embodiment of the invention is a process for producing a variant LovD polypeptide comprising culturing a host cell transformed with a encoding a variant LovD polypeptide under conditions suitable for expression of a polypeptide, so that the variant LovD polypeptide is produced. In certain embodiments of the invention, the variant LovD polypeptide can be fused to a heterologous amino acid sequence, for example one that facilitates its manipulation (e.g. a polyhistidine sequence).

Yet another embodiment of the invention is a method of making a variant of a LovD polypeptide shown in SEQ ID NO:1 comprising: using a polynucleotide mutagenesis procedure to generate a population of mutants of the LovD polynucleotides; and expressing a population of LovD polypeptide variants encoded by the population of LovD polynucleotide mutants; so that a variant of a LovD polypeptide is made. Optionally, the polynucleotide mutagenesis procedure is a saturation mutagenesis or an error prone polymerase chain reaction procedure. Typically these embodiments of the invention include screening one or more members of the population of LovD polypeptide variants so as to identify a variant that exhibits: a decreased aggregation; an improved thermal stability; an improved acyltransferase activity; an improved kcat/Km value; an improved soluble expression level; and/or an improved whole cell activity at 25° C., as compared to the wild type LovD polypeptide shown in SEQ ID NO:1. Optionally the polynucleotide mutagenesis procedure is controlled so as to generate a substitution mutation at a codon that encodes amino acid residue position: A10; D12; K26; A86; A190; H161; K227; G275; V334; and/or L361. In a related embodiment of the invention, the polynucleotide mutagenesis procedure is controlled so as to generate a variant comprising C40A and C60N; and a further a substitution mutation at a codon that encodes amino acid residue position: A10; D12; K26; A86; A190; H161; K227; G275; V334; and/or L361.

Yet another embodiment of the invention is a method of making simvastatin comprising the steps of: combining together monacolin J; an acyl thioester that donates an acyl moiety to the C8 hydroxyl group of monacolin J in the presence of LovD acyltransferase; and a variant of a LovD acyltransferase polypeptide shown in SEQ ID NO:1, the variant LovD polypeptide comprising at least one amino acid substitution at residue position: A10; D12; K26; A86; A190; H161; K227; G275; V334; or L361; and then allowing the variant LovD polypeptide to use an acyl group from the acyl thioester to regioselectively acylate the C8 hydroxyl group of monacolin J; so that simvastatin is made. In certain embodiments of the invention, the monacolin J; the acyl thioester and the variant LovD polypeptide are combined in a fermentation media in the presence of an isolated organism that produces the LovD acyltransferase wherein the isolated organism is at least one of: *Aspergillus terreus; Aspergillus terreus* that does not express LovF polypeptide of SEQ ID NO: 3; *Escherichia coli*; or *Escherichia coli* that does not express bioH polypeptide of SEQ ID NO: 4. Optionally in such embodiments, the acyl thioester is selected a butyrlyl-thioester, a N-acetylcysteamine thioester or a methyl-thioglycolate thioester; comprises medium chain length (C3-C6) acyl group moieties; and/or is able to cross the cellular membranes of *Escherichia coli* or *Aspergillus terreus* cells growing within a fermentation media (e.g. α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB)).

In the methods for making simvastatin, the isolated organism can be grown under at least one of the following conditions: at a temperature between 25-40° C.; for a time period between at least 4 to at least 48 hours; at a pH between 7-8; and/or in a fermentation media comprising LB, F1 or TB media. Optionally the methods further comprise purifying the simvastatin made by the method by at least one purification step comprising: lysis of cells of an isolated organism present in the combination; centrifugation; precipitation of a free acid form of simvastatin; conversion of a free acid form of simvastatin to a simvastatin salt; filtration; or high performance liquid chromatography (HPLC). In certain embodiments, the method produces a composition of matter comprising 0%-1% of the monacolin J that was initially combined with the acyl thioester that donates an acyl moiety to the C8 hydroxyl group of monacolin J in the presence of a LovD acyltransferase variant; and/or results in at least 95% of the monacolin J added to the combination being converted to simvastatin. Optionally in these methods, the variant LovD polypeptide comprises amino acid substitutions: D12G, C40A, C60N, A86V, A190T and G275S; D12G, K26E, C40A, C60N, A86V, H161Y, A190T and G275S; or D12G, K26E, C40A, C60N, A86V, H161Y, A190T; G275S and V334F. A related embodiment of this invention is a composition of matter comprising: monacolin J; an acyl thioester that donates an acyl moiety to the C8 hydroxyl group of monacolin J in the presence LovD acyltransferase; a variant of a LovD acyltransferase polypeptide shown in SEQ ID NO:1, the variant LovD polypeptide comprising an amino acid substitution at: amino acid residue positions C40 and C60; and at least one amino acid residue position: A10; D12; K26; A86; A190; H161; K227; G275; V334; or L361; and simvastatin.

Yet another embodiment of the invention is a method of making huvastatin comprising the steps of: combining together hydrolyzed pravastatin tetra-ol; an acyl thioester that donates an acyl moiety to the C8 hydroxyl group of hydrolyzed pravastatin tetra-ol in the presence of LovD acyltransferase; and a variant of a LovD acyltransferase polypeptide shown in SEQ ID NO:1, the variant LovD polypeptide comprising an amino acid substitution at amino acid residue position: A10; D12; K26; C40; C60; A86; A190; H161; K227; G275; V334; and/or L361; and allowing the variant LovD polypeptide to use an acyl group from the acyl thioester to regioselectively acylate the C8 hydroxyl group of hydrolyzed pravastatin tetra-ol; so that huvastatin is made. A related embodiment of the invention is a composition of matter comprising: hydrolyzed pravastatin tetra-ol; an acyl thioester that donates an acyl moiety to the C8 hydroxyl group of hydrolyzed pravastatin tetra-ol in the presence LovD acyltransferase; a variant of a LovD acyltransferase polypeptide shown in SEQ ID NO:1, the variant LovD polypeptide comprising an amino acid substitution at amino acid residue position: A10; D12; K26; C40; C60; A86; A190; H161; K227; G275; V334; and/or L361; and huvastatin. Optionally this variant LovD polypeptide comprises amino acid substitutions: D12G, C40A, C60N, A86V, A190T and G275S; D12G, K26E, C40A, C60N, A86V, H161Y, A190T and G275S; or D12G, K26E, C40A, C60N, A86V, H161Y, A190T; G275S and V334F.

In certain embodiments of the invention, further components and/or methodological steps can be combined with one or more of the methods and materials discussed above. For example, the methods can further comprise using high cell-density fermentation to increase the effective concentration of one or more LovD acyltransferase variants used to make simvastatin and/or huvastatin and optimise fermentation conditions or increasing LovD acyltransferase catalytic efficiencies and the like. Many other components or methods can be used to increase the production of simvastatin or of an intermediary or related compound that facilitates the production of simvastatin and/or huvastatin.

Embodiments of the invention also include articles of manufacture and/or kits designed to facilitate the methods of the invention. Typically such kits include instructions for using the elements therein according to the methods of the present invention. Such kits can comprise a carrier means being compartmentalized to receive in close confinement one or more container means such as vials, tubes, and the like, each of the container means comprising one of the separate elements to be used in the method. One of the containers can comprise a vial, for example, containing a plasmid encoding a LovD acyltransferase variant, optionally within a microbial host such as *E. Coli* or *A. terreus* and another vial containing a thioester compound or the like, both of which can be added to a fermentation mixture to produce simvastatin and/or huvastatin or the like.

Additional embodiments of the invention are discussed below.

BRIEF DESCRIPTION OF THE DRAWINGS

(FIG. 8A) A structure-based sequence alignment between LovD and EstB. Secondary structure elements assigned from the structure of LovD are shown above the sequence. The colors are ramped from blue at the N-terminus to red at the C-terminus. The active site residues in EstB are indicated by an asterisk "*" below the amino acid. (FIG. 8B) A ribbon diagram showing the G5'-LVA complex. (FIG. 8C) Structure of LovD. Highlighted in green are segments that are not conserved in EstB. These five loops project around the circumference of the active site like the fingers in a catcher's mitt. (FIG. 8D) Structure of EstB. Highlighted in magenta are segments that are not conserved in LovD. (FIG. 8E) The overlay of LovD and EstB structures. Notably absent from LovD is a loop that covers the active site in EstB (residues 244-260).

(FIG. 9A) An agar diffusion-based assay was used to quantify the amount of SVA in the whole-cell activity experiments. N. crassa was embedded in the agar prior to spotting the reaction mixture. The numbers (1-8) designate different incubation times of 2.5, 4, 5.5, 7, 8, 9, 10, 12 hours following addition of MJA and DMB-SMMP to E. coli expressing wild type LovD. (FIG. 9B) Directed evolution of LovD mutants towards higher whole cell activities. There are a total of seven generations of LovD mutants. Four generations were derived from random mutagenesis including G1, G2.1, G2.2, G4.1, G4.2, and G6. Two generations were derived from combination of beneficial mutations from previous generation mutants including G3 and G5. G7 was derived though saturated mutagenesis of G6 at positions V334 and L361. All mutants with two amino acid changes were subjected to site directed mutagenesis to determine beneficial or deleterious mutations (G2.1, G4.1 and G4.2). (x) indicates that the mutant had lower whole cell activity comparing to the previous generation. (√) indicates that the mutant had higher whole cell activity comparing to the previous generation.

FIG. 13. To dissect the contributions that led to the increases in whole cell activity, kinetic parameters ($k_{cat}$, $K_m$), soluble protein levels and thermal stability of all the improved mutants were characterized and listed. The whole-cell activity of LovD mutants are compared to G0, which has a conversion rate of 1.7 mM/hr and is normalized to 1. $^{†}K_M$ of MJA is derived at 25° C. when DMB-SMMP is fixed at 2 mM. $^{‡}K_M$ of DMB-SMMP is derived when MJA is fixed at 2 mM. $^{§}$The amounts of soluble proteins are measured from purified protein levels. $^{552}$Tm is measure by circular dichroism. All results represent mean values of triplicate determinations ±SD.

(FIG. 16A) Structure of LovD with secondary structure element from N-terminal (blue) to C-terminal (red) and topology diagram of LovD secondary structure (arrows represent β-sheet and rectangles represent α-helix). LVA was shown in grey stick. (FIG. 16B) The positively charged tunnel to the active site of LovD and the positively charged ridges (circled area) may interact with the ACP domain and the pPant arm of LovF. (FIG. 16C) Hydrophobic and aromatic amino acids involved in the MJA binding pocket.

(FIG. 18A) The K26E mutation might improve stability of the enzyme by breaking up a patch of positively charged residues (R22, K23, K26, and R28) on the surface of helix A. The patch is highlighted with a circle in both G0-Semet and G5. (FIG. 18B) The G275S mutation appears to improve stability of the enzyme by adding a hydrogen bond with S278 on helix I.

(FIG. 19A) Proposed residues involved in LovD reaction. (FIG. 19B) Superimposition of the active site residues between LovD (gray) and EstB (magenta). (FIG. 19C) LVA biosynthesis using MJA and MB-LovF_ACP as substrate. Ser76 acts as the catalytic nucleophile to catalyze the ester exchange reaction. The hydroxyl groups Ser76 and MJA (C8) are deprotonated by Tyr188, which is stabilized by Lys79.

FIG. 20. Statistics of X-ray data collection and atomic refinement (numbers in parentheses refer to the outer shell of data). $R_{merge}=\Sigma|I-<I>|^2/\Sigma I^2$, where I is the observed intensity. Both summations involve all input reflections for which more than one symmetry equivalent is averaged. $R_{work}=\Sigma\|F_o|-|F_c\|/\Sigma|F_o|$, where $F_o$ and $F_c$ refer to observed and calculated structure factors, respectively. $R_{free}$ is similar to $R_{work}$, but is based on a subset of the reflections, which were withheld from refinement for cross validation (Brünger, A. T. (1992). Nature, 355, 472-474). The acronym R.M.S. stands for root mean square value.

DETAILED DESCRIPTION OF THE INVENTION

Figure 1:
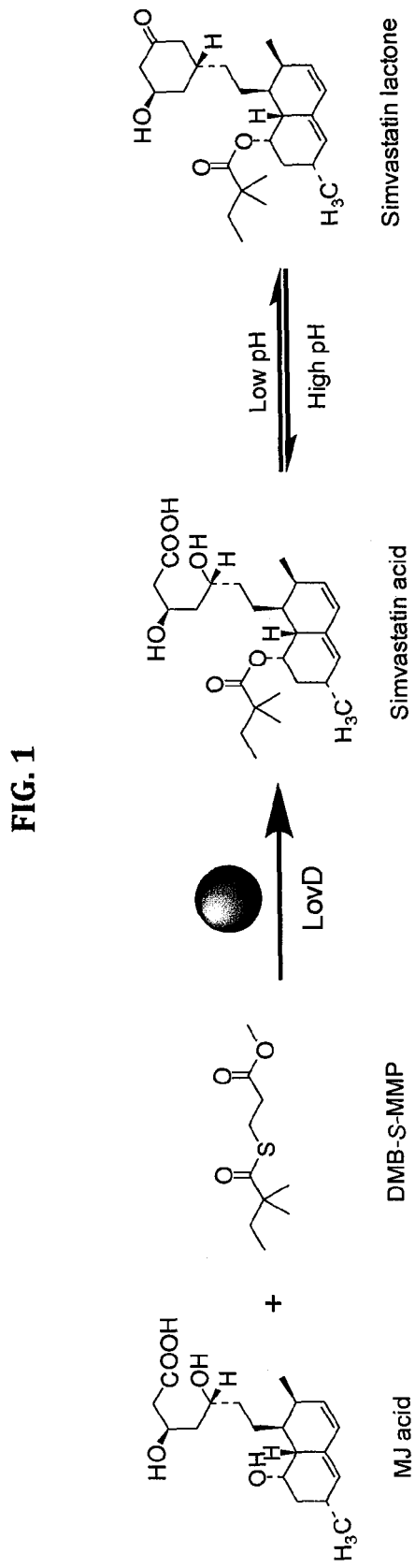
FIG. 1. *E. coli* strain overexpressing the acyltransferase LovD was used as a biocatalyst to convert Monacolin J (MJ) acid and DMB-S-MMP to simvastatin in one step. Simvastatin acid form will automatically convert to lactone form at low pH and the lactone will convert to acid form in high pH conditions. The wild type LovD has a $k_{cat}$ of 0.6 $min^{-1}$. In vivo experiment showed that the wild type LovD expressed in *E. coli* YT2 can convert 15 mM MJ acid into simvastatin acid in 12 hours.

The techniques and procedures described or referenced herein are generally well understood and commonly employed using conventional methodology by those skilled in the art, such as, for example, the widely utilized molecular cloning methodologies described in Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted. Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Disclosures describing methods and materials which can be adapted for use with embodiments of the invention disclosed herein include, for example, International Publication No. WO 2007/139871; and Xie et al., Biotechnology and Bioengineering, Vol. 102, No. 1 (2008). All numbers recited in the specification and associated claims that refer to values that can be numerically characterized can be modified by the term "about".

The definitions of certain terms are provided below.

"Lovastatin" (Mevacor) is a fungal polyketide produced by *Aspergillus terreus* (see, e.g., A. W. Alberts, J. et. al., Proc. Natl. Acad. Sci. U.S.A., 1980, 77, 3957-3961 and A. Endo, J. Antibiot. 1980, 33, 334-336; and J. K. Chan, et. al., J. Am. Chem. Soc. 1983, 105, 3334-3336; Y. Yoshizawa, et. al., J. Am. Chem. Soc. 1994, 116, 2693-2694). It is a pharmaceutically important compound because of its potent inhibitory activities towards hydroxymethylglutaryl coenzyme A reductase (HMGR), the rate-limiting step of cholesterol biosynthesis, and therefore it is widely used in the treatment of hyperlipidemia, hypercholesterolemia, and the like. Lovastatin is also referred to as Mevacor.

"Simvastatin" is an analog of lovastatin. It is favored over lovastatin because of the absence of adverse side effects and its high absorbability in the stomach. Also, it has been reported that simvastatin prevents and reduces the risk of Alzheimer's disease(AD) by retarding the production of Ab42, β-amyloid protein associated with AD. It is known in the art that simvastatin can be synthetically prepared by way of direct methylation of the 8'-methylbutyryloxy side chain of lovastatin of formula using a methyl halide in the presence of a metal amide base. The C-methylation step has to be carried out at extremely low temperatures (−75 to −30°) using a strong base under anhydrous condition which is difficult to handle in mass production (see, e.g., U.S. Pat. No. 5,393,893, U.S. Pat. No. 4,582,915, U.S. Pat. No. 5,763,646, U.S. Pat. No. 5,763,653, EP Patent No. 299,656 and International Patent Publication No. WO 99/45003, the contents of which are herein incorporated by reference). Other methods of synthetically producing simvastatin is also known in the art. For example, lovastatin can be hydrolyzed with an excessive amount of lithium hydroxide to remove the 2-methylbutyryl side chain and to simultaneously open its 6-membered lactone ring to produce a triol acid. The triol acid compound can then be heated to obtain a diol lactone. The hydroxy group on the lactone ring of the diol lactone can be protected to obtain a tert-butyldimethylsilyl ether and then the hydroxy group at C8 of the hexahydronaphthalene ring system can be acylated with 2,2-dimethylbutaonic acid in the presence of dicyclohexyl carbodiimide, or 2,2-dimethyl chloride to produce a compound. The t-butyldimethylsilyl protecting group of the compound can then be removed in the final step using tetrabutylammonium fluoride to produce simvastatin (see, e.g., U.S. Pat. No. 4,444,784, the contents of which are herein incorporated by reference).

Figure 2:
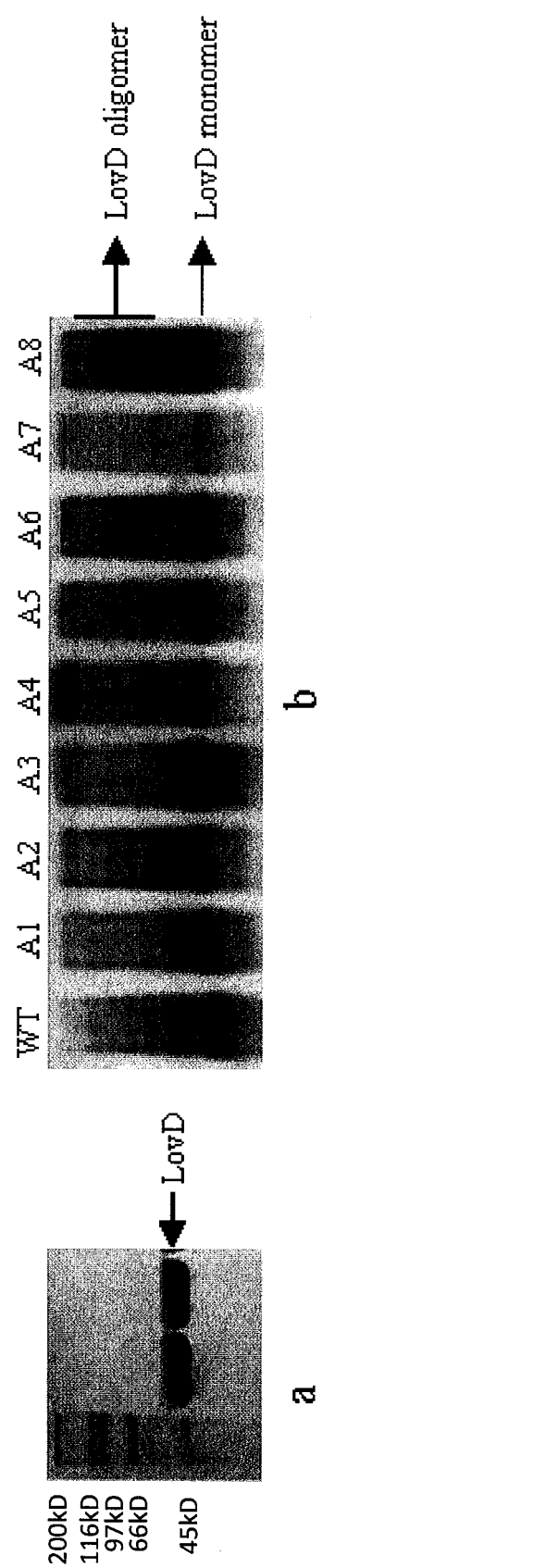
FIG. 2. (a) SDS-PAGE gel LovD protein (WT) from *E. coli* BL21(DE3)/pAW31; (b) native gel of LovD protein (WT) and A1-A8 respectively, DTT was fixed at 2 mM for all samples. A1 has slightly less oligomer compared to WT; A3 eliminated most of the oligomer; A2, A6 and A8 are very similar to WT; A4, A5, and A7 showed less proteins due to the unstability of these mutants; A9 was not included due to no soluble proteins. The results indicated that only C1 and C3 may be responsible for intermolecular disulfide bonds.

"Lovastatin derivatives" as used herein comprises lovastatin derivatives or precursors for example pravastatin, huvastatin, simvastatin, or hydrolyzed pravastatin tetra-ol. "Monacolin J variants" refers to monacolin J variants disclosed in the art, for example hydrolyzed pravastatin tetra-ol or 6-hydroxyl-6-desmethylmonacolin J and the like. In certain embodiments of the invention, "Monacolin J variants" refers to Monacolin J compounds having substitutions at the C6 position in FIG. 2. In describing compounds such as simvastatin, pravastatin, monacolin J and variants etc., those of skill in the art understand that this language is intended to encompass these compounds as well as the salts of these compounds (e.g. pharmaceutically acceptable salts known in the art). For example, as is known in the art, simvastatin can occur both a free acid form as well as a simvastatin sodium, potassium or ammonium salts, and other salts derived from alkaline earth elements or other metallic salts.

"Aspergillus terreus" or "A. terreus" is a filamentous ascomycete commonly found in soil. A variety of A. terreus strains are know in the art, for example those deposited as, e.g., ATCC 20542 and ATCC 20541.

As is known in the art, genes related to biosynthesis of secondary metabolites of filamentous fungi can form a cluster on the fungal genome and are referred to as "gene clusters." For example, "Lovastatin-producing gene cluster" can refer to a set of genes that produce lovastatin, the set of genes comprising, LovA, a P450I; LovC, a dehydrogenase; LovD, an esterase and acyltransferase; and LovF, a ScPKS or LDKS. It has been determined previously that each of these four genes (LovA, LovC, LovD, and LovF) is required for lovastatin synthesis (see, e.g., U.S. Pat. No. 6,943,017, the contents of which are herein incorporated by reference). LovF (LDKS gene) is characterized as a polyketide synthase gene. LovD is a putative esterase/carboxypeptidase-like gene. Disruption of the LovF gene has been done previously (see, e.g., U.S. Pat. No. 6,943,017, the contents of which are herein incorporated by reference). LovD interacts with LovF to produce lovastatin; however, the LovD-LovF interaction is not required for the production of simvastatin. Moreover, another gene in the lovastatin-producing gene cluster is LovE, which is a Zn finger that can regulate the transcription of the other genes. The lovastatin-producing gene cluster also comprises LovB (NPKS gene).

"LDKS" or "LDKS gene" refers to the protein encoded by the LovF gene, a member of the lovastatin-producing gene cluster. LDKS stands for lovastatin diketide synthase. LovF is the gene that produces LDKS. LovF is also the gene that produces LovF protein. "LDKS gene" also refers to the gene that produces LDKS. In the synthesis of lovastatin, LDKS synthesizes the five carbon unit side chain of monacolin J through condensation between an acetyl-CoA and a malonyl-CoA. The condensed diketide undergoes methylation and reductive tailoring by the individual LovF domains to yield an α-S-methylbutyryl thioester covalently attached to the phosphopantetheine arm on the acyl carrier protein (ACP) domain of LovF.

"LovD acyltransferase" as used herein refers to those polypeptides such as the A. terreus LovD polypeptide (e.g. SEQ ID NO: 1) that can use a acyl thioester to regiospecifically acylate the C8 hydroxyl group of monacolin J so as to produce simvastatin. As also disclosed herein, this LovD enzyme can further utilize a acyl thioester to regiospecifically acylate the C8 hydroxyl group of hydrolyzed pravastatin tetra-ol so as to produce huvastatin.

LovD acyltransferases include homologous enzymes to A. terreus LovD polypeptide (e.g. SEQ ID NO: 1) that can be found in for example, but not limited to, fungal polyketide gene clusters. For example, the art provides evidence that Mlc in the compactin biosynthetic pathway catalyzes the identical transacylation reaction (see, e.g., Y. Abe, T. et. al., Mol Genet Genomics. 2002, 267, 636-646), whereas an acyltransferase in the squalestatin pathway can catalyze a similar reaction between an ACP-bound tetraketide thioester and an aglycon (see, e.g., R. J. Cox, F. et. al., Chem Commun (Camb) 2004, 20, 2260-2261). The amino acid sequence of A. terreus LovD polypeptide (e.g. SEQ ID NO: 1) resembles type C β-lactamase enzymes, which catalyze the hydrolytic inactivation of the β-lactam class of antibiotics (see., e.g., E. Lobkovsky, E. M. et. al., Biochemistry, 1994, 33, 6762-6772 and A. Dubus, D. et. al., Biochem. J. 1993, 292, 537-543).

Alignment of A. terreus LovD polypeptide (e.g. SEQ ID NO: 1) with the enterobacter cloacae P99 lactamse (see, e.g., S. D. Goldberg, et. al., Protein Sci. 2003, 12, 1633-1645) shows moderate sequence homology, including potentially conserved active site residues, such as the catalytic Ser76, Lys79, Tyr188, and Lys315 (see. e.g. S. D. Goldberg, et. al., Protein Sci. 2003, 12, 1633-1645).

LovD acyltransferases can also refer to both genetically engineered and naturally occurring enzymes that are related to A. terreus LovD polypeptide (e.g. SEQ ID NO: 1) in sequence but containing slight amino acid differences (e.g. 1-10 amino acid substitution mutations). Simvastatin, for example, can be produced from naturally occurring enzymes that are similar to A. terreus LovD polypeptide (e.g. SEQ ID NO: 1) in sequence (e.g. the MlCH from the compactin cluster). "LovD acyltransferases" can also refer to mutants of A. terreus LovD polypeptide (SEQ ID NO: 1). It is known in the art that mutants can be created by standard molecular biology techniques to produce, for example, mutants of SEQ ID NO: 1 that improve catalytic efficiencies or the like. For example, we used rational and directed evolution approaches to improve the catalytic turnover rates of A. terreus LovD. Typically such mutants will have a 50%-99% sequence similarity to SEQ ID NO: 1. In this context, the term "LovD homologous enzyme" includes a LovD polypeptide having at least 80%, 85%, 90%, 95%, 97%, 98% or 99% sequence identity with the amino acid sequence set out in SEQ ID NO: 1, wherein the polypeptide has the ability to utilize a acyl thioester to regiospecifically acylate the C8 hydroxyl group of monacolin J so as to produce simvastatin and/or utilize a acyl thioester to regiospecifically acylate the C8 hydroxyl group of hydrolyzed pravastatin tetra-ol so as to produce huvastatin. Such mutants are readily made and then identified in assays which observe the production of a desired compound such as simvastatin (typically using A. terreus LovD polypeptide (e.g. SEQ ID NO: 1) as a control). These mutants can be used by the methods of this invention to make simvastatin or huvastatin, for example. The terms "variant LovD polypeptide", "LovD polypeptide variant" "LovD acyltransferase variant" and the like refer to an active LovD polypeptide as disclosed herein and having at least about 90%-99% amino acid sequence identity with LovD having the amino acid sequence shown in SEQ ID NO:1. Such variants include, for instance, LovD polypeptides wherein one or more amino acid residues in SEQ ID NO:1 are substituted, added, or deleted.

"Heterologous" as it relates to nucleic acid sequences such as coding sequences and control sequences denotes sequences that are not normally associated with a region of a recombinant construct, and/or are not normally associated with a particular cell. Thus, a "heterologous" region of a nucleic acid construct can be an identifiable segment of nucleic acid within or attached to another nucleic acid molecule that is not found in association with the other molecule in nature. For example, a heterologous region of a construct can include a coding sequence flanked by sequences not found in association with the coding sequence in nature. Similarly, a host cell transformed with a construct, which is not normally present in the host cell, would be considered heterologous (see, e.g., U.S. Pat. Nos. 5,712,146 6,558,942, 6,627,427, 5,849,541 the contents of which are herein incorporated by reference). For instance, a construct with Lov genes can be isolated and expressed in non-lovastatin producing fungi or yeast host cells, and lovastatin can thereby be produced (see, e.g., U.S. Pat. Nos. 6,391,583 and 6,943,017, the contents of which are herein incorporated by reference). As another example, prokaryotes such as bacteria can be host cells also, as is known in the art. Fungal genes may also be cloned into an expression vector for expression in prokaryotes (see, e.g., U.S. Pat. No. 5,849,541, the contents of which are herein incorporated by reference).

A prokaryote such as *E. coli* can be used as a heterologous host. A plasmid can be constructed with a gene of interest and the plasmid can be transformed into *E. coli*. The gene of interest can be translated and the protein derived from the gene of interest can be purified thereafter. This method of expression and protein purification is known in the art. For example, LovD exons from *A. terreus* can be individually amplified from the genomic DNA of *A. terreus* and spliced to yield a continuous open reading frame using splice overlap extension PCR. Restriction sites can be introduced, and the gene cassette can be ligated to a vector to yield an expression construct that can be transformed into *E. coli*. Thereby, *E. coli* can be used as a heterologous host for expression of *A. terreus* genes. *E. coli* can be co-cultured with another strain that produces another substrate of interest. Additionally, substrates can be added to this culture or co-culture. Heterologous expression of the lovastatin biosynthesis genes is known in the art (see, e.g., U.S. Pat. Nos. 6,391,583 and 6,943,017, the contents of which are herein incorporated by reference).

As another example, certain polyketides, such as polyketides from fungi, or other organisms, can be heterologously expressed in *E. coli*, yeast, and other host organisms. These host organisms can be supplemented with other substrates, since they can require both the heterologous expression of a desired PKS and also the enzymes that produce at least some of the substrate molecules required by the PKS (see, e.g., U.S. Pat. No. 7,011,959, the contents of which are herein incorporated by reference). Similarly, fungal Lov genes can be expressed in *E. coli* or other bacterium, and these host bacteria can be supplemented with other substrates, such as acyl-SNAC or other acyl donor groups. These acyl donor groups can be cell permeable, and enter the bacterial cell.

"Expression vector" refers to a nucleic acid that can be introduced into a host cell. As is known in the art, an expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which typically is translated into a polypeptide in the cell or cell extract. For example, suitable promoters for inclusion in the expression vectors of the invention include those that function in eukaryotic or prokaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (b/a), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1I, pBR and pET (e.g. pET28). For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, can be used and confer a selectable phenotype on transformed cells when the cells are grown in an appropriate selective medium. For example, an expression vector containing the Lov gene cluster or portions thereof can be introduced into a heterologous host, such as *E. coli*. Thus, recombinant expression vectors can contain at least one expression system, which, in turn, can be composed of at least a portion of Lov and/or other biosynthetic gene coding sequences operably linked to a promoter and optionally termination sequences that operate to effect expression of the coding sequence in compatible host cells.

A "coding sequence" can be a sequence which "encodes" a particular gene, such as a gene from the Lov gene cluster, for example. A coding sequence is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence will usually be located 3' to the coding sequence.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof.

"Lovastatin-producing organism" refers to the wide variety of different organisms known in the art to produce lovastatin. These organisms that produce lovastatin can modified to produce simvastatin by the methods of this invention. *A. terreus* is an example of a lovastatin producing organism. Microorganisms other than *A. terreus* reported to produce lovastatin (mevinolin) include *Monascus* species, for example *M. ruber, M. purpureus, M. pilosus, M. vitreus, M. pubigerus,* as well as *Penicillium, Hypomyces, Doratomyces, Phoma, Eupenicillium, Gymnoascus,* and *Trichoderma* species, *Pichia labacensis, Candida cariosilognicola, Aspergilus ogea, Doratomyces stemonitis, Paecilomyces virioti, Penicillum citrinum, Penicillin chrysogenum, Scopulariopsis brevicaulis* and *Trichoderma viride* (see, e.g., U.S. Pat. No. 6,391,583; Juzlova et al., J. Ind. Microbiol. 16:163-170; Gunde-Cimerman et al., FEMS Microbiol. Lett. 132:39-43 (1995); and Shindia et al., Folio Microbiol. 42:477-480 (1997), the contents of which are herein incorporated by reference).

"Non-lovastatin-producing organisms" as used herein refers to a number organisms that do not produce lovastatin absent manipulation by man (e.g. *E. Coli*). These organisms can be induced to produce LovD, or cultured in the presence of LovD to produce lovastatin or simvastatin by the methods of this invention, for example.

"*A. terreus* having a disruption in the LDKS gene" comprises an *A. terreus* without the LDKS gene, having a LDKS gene that is mutated, having a LDKS gene that is knocked-out, having a LDKS gene that is deleted, having a LDKS gene whose expression is disrupted, or having a LDKS gene that is disrupted. "*A. terreus* having a disruption in the LDKS gene" comprises an *A. terreus* having a LDKS gene that is silenced by methods known in the art. "*A. terreus* having a disruption in the LDKS gene" refers to an *A. terreus* that cannot produce functional LDKS. "*A. terreus* having a disruption in the LDKS gene" can also refer to an *A. terreus* that produces functional LDKS. The LDKS can be inactivated or inhibited by methods known in the art such as gene knock out protocols. The amount of LDKS present can be reduced by methods known in the art. Other methods of inhibition, inactivation, or disruption of LDKS gene or protein include, but or not limited to, antisense, siRNA, RNAi, or RNA interference as is known in the art. "LDKS gene" as used herein can also refer to the LovF gene. Disruption of the LovF gene is known in the art (see, e.g., U.S. Pat. No. 6,391,583 the contents of which are herein incorporated by reference. "*A. terreus* having a disruption in the LDKS gene" is typically a genetically manipulated organism. Genetic manipulation of *A. terreus* is known in the art. Gene disruption of the Lov genes in *A. terreus* has been done previously (see, e.g., U.S. Pat. Nos. 6,391,583 and 6,943,017, the contents of which are herein incorporated by reference). Disruption of specifically the LovF gene (producing LDKS) in *A. terreus* has been done previously (see, e.g., U.S. Pat. No. 6,943,017, the contents of which are herein incorporated by reference). Disruption of the LovF gene can occur by other methods as is known in the art. *A. terreus* having a disruption in the LDKS gene can be in a fermentation mixture. Substrates can be added to the fermentation mixture of an *A. terreus* having a disruption in the LDKS gene to produce lovastatin analogs.

"A component or method to increase the production of simvastatin" as used herein refers to a compound or substrate, synthetic or natural, that increases the production of certain intermediaries to increase the amount of simvastatin produced for scale-up and large-scale synthesis of simvastatin. Components and methods for increasing the production of certain intermediaries are known in the art. For example, compounds that are added to the fermentation mixture to increase the amount of intermediaries, such as monacolin J, in the production of lovastatin are known in the art (see, e.g., U.S. Pat. No. 6,943,017, the contents of which are herein incorporated by reference). Some of these intermediaries, such as monacolin J, can also be used in the production of simvastatin. Compounds for increasing the production of monacolin J thereby can be added to increase the production of simvastatin. For example, compounds for increasing the production of monacolin J can be directly added to the fermentation mixture to increase the amount of simvastatin produced. An example of a component for increasing the production of simvastatin is a clone containing the D4B segment of the lovastatin producing gene cluster that is deposited in ATCC accession number 98876. This clone can be transformed into a non-lovastatin producing organism to produce monacolin J as is known in the art. This clone can also be transformed into a lovastatin-producing organism to increase the production of monacolin J and thereby increase the production of simvastatin. Moreover, another example of a component for increasing the production of simvastatin is the LovE/zinc finger gene, which can be transformed into a lovastatin-producing organism to increase the production of simvastatin. Preferably, this lovastatin-producing organism would have a disruption in the LDKS gene (see, e.g., U.S. Pat. No. 6,391,583, the contents of which are herein incorporated by reference). Components and methods to increase the production of simvastatin can refer to many others and are not limited to the examples listed above.

As disclosed herein, an "Acyl donor" or "acyl carrier" is a compound having an acyl group that can be transferred to simvastatin and/or a simvastatin precursor or a related compound. Typically, "Acyl donor" or "acyl carrier" is an acyl thioester that donates an acyl moiety to the C8 hydroxyl group of monacolin J. A wide variety of such agents are known in the art that are further shown herein to have this activity (see, e.g. the illustrative acyl-thioesters in Table 1). In addition to those known in the art and further shown by the instant disclosure to have this activity, any potential acyl donor/carrier known in the art (or synthesized de novo) having an ability to acylate C8 of monacolin J so as to produce simvastatin can be easily identified by comparative experiments with the acyl donors disclosed herein (e.g. acyl-SNAC). As is known in the art, an acyl group can have the formula RCON; wherein R can be an alkyl or aryl and N can be —Cl, —OOCR, —NH2, —OR, or the like. Compounds that have an acyl group includes, but is not limited to, acid chlorides, esters, amides, or anhydrides and the like. These compounds can be aliphatic or aromatic, substituted or unsubstituted. Examples include, but are not limited to, benzoyl chloride, benzoic anhydride, benzamide, or ethyl benzoate, and the like. Other examples of acyl donors include, but are not limited to, α-dimethylbutyryl-SNAC, acyl-thioesters, acyl-CoA, butyryl-CoA, benzoyl-CoA, acetoacetyl-CoA, β-hydroxybutyryl-CoA, malonyl-CoA, palmitoyal-CoA, butyryl-thioesters, N-acetylcyteamine thioesters (SNAC), methyl-thioglycolate (SMTG), benzoyl-SNAC, benzoyl-SMTG, or α-S-methyl-butyryl-SNAC. These compounds can be produced naturally or synthetically, and, in some cases, can penetrate the cell membrane. A number of these compounds can be added to LovD in the presence of monacolin J to produce simvastatin for example.

"Acyl-SNAC" as used herein refers to α-dimethylbutyryl-SNAC. As is known in the art, acyl-SNAC can penetrate the cell membrane under in vivo conditions. LovD can use acyl-SNAC as a substrate to initiate the reaction from monacolin J to simvastatin by regiospecifically acylating the C8 hydroxyl group of monacolin J. Acyl-SNAC can donate its acyl group to LovD.

TYPICAL EMBODIMENTS OF THE INVENTION

Those of skill in the art will understand that the disclosure provided herein allows artisans to produce a wide variety of embodiments of the invention. Illustrative embodiments of the invention include methods of making simvastatin (or related compounds such as huvastatin) by combining together monacolin J; an acyl thioester that donates an acyl moiety to the C8 hydroxyl group of monacolin J in the presence of a LovD (and/or a LovD acyltransferase variant as disclosed herein); and a LovD acyltransferase variant; and then allowing this LovD acyltransferase variant use an acyl group from the acyl thioester to regioselectively acylate the C8 hydroxyl group of monacolin J; so that simvastatin (or the related compound) is made.

Another illustrative embodiment of the invention is a variant of a LovD polypeptide shown in SEQ ID NO:1 comprising at least one amino acid substitution at residue position: A10; D12; K26; C40; C60; A86; A190; H161; K227; G275; V334; or L361. While such LovD single substitution variants can exhibit improved properties over the wild type protein, LovD substitution variants having multiple substitutions are shown to further improved properties. Consequently, using the disclosure provided herein, the artisan can construct LovD substitution variants having a substitution at any first position identified above in combination with a substitution at any second position identified above; or in combination with a substitution at any second as well as at any third position identified above; or in combination with a substitution at any second as well as at any third position, fourth position, fifth position etc. etc. identified above. For example, in some embodiments of the invention, the variant LovD polypeptide comprises at least one specific amino acid substitution such as A10V; D12G; K26E; C40A; C60N; A86V; H161Y; A190T; K227R; G275S; V334D; V334F; and/or L361M. In another illustrative embodiment of the invention is a variant of a LovD polypeptide shown in SEQ ID NO:1, the variant LovD polypeptide comprising a set of amino acid substitutions at: amino acid residue positions C40 and C60; and at least one further amino acid residue position: A10; D12; K26; A86; A190; H161; K227; G275; V334; or L361. Typically, the substitution variant exhibits one or more altered properties as compared to the LovD polypeptide shown in SEQ ID NO:1, for example, a decreased aggregation; an improved thermal stability; an improved catalytic activity; an improved $k_{cat}/K_m$ value; an improved soluble expression level; and/or an improved whole cell activity at 25° C.

For purposes of shorthand designation of LovD polypeptide variants described herein, it is noted that numbers refer to the amino acid residue position along the amino acid sequence of the LovD polypeptide. Amino acid identification uses the single-letter alphabet of amino acids, i.e.,

| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | ASN | N | Asparagine |

In this context, a variant LovD polypeptide having a "C40A" substitution is one where the cysteine amino acid ("C") at amino acid position 40 of SEQ ID NO: 1 has been substituted for alanine ("A"). In such substitution variants of the LovD polypeptide, the amino acid substitution can comprise any one of the 19 amino acids not found at the amino acid residue position on the LovD polypeptide shown in SEQ ID NO:1. In particular, the pertinent art teaches that in situations where methodical experimentation has established that the properties of a specific residue at a particular position within the polypeptide chain are crucial for maintaining some aspect of a protein's functional integrity (i.e. as is disclosed herein), an alteration in the size, shape, charge, hydrogen-bonding capacity or chemical reactivity of the amino acid side chain at one of these "active" amino acid positions is likely to affect the function of the protein in some way (Rudiger et al., Peptide Hormones, University Park Press (1976)). In this context, the disclosure that is included in the Examples below (e.g. mutagenesis protocols and processes for the characterization of mutant properties) shows that the properties LovD variants having 1, 2, 3, 4, 5, 6, 7, or more amino acid substitutions in LovD at the positions disclosed herein (e.g. the specific substitutions shown in FIG. 13 or any one of the other 19 amino acids not found at the corresponding wild-type amino acid residue position) can be determined with only routine experimentation.

Certain embodiments of the invention include specific constellations of amino acid substitutions (see, e.g. FIG. 13). For example, in some embodiments of the invention, the variant LovD polypeptide comprises amino acid substitutions at: amino acid residue positions C40; C60; and A86; amino acid residue positions C40; C60; A86; and A190; amino acid residue positions C40; C60; D12; A86; and G275; amino acid residue positions C40; C60; D12; A86; C40; C60; A190; and G275; amino acid residue positions C40; C60; D12; K26; A86; C40; C60; H161; A190; and G275; amino acid residue positions C40; C60; D12; A86; A190; and G275; amino acid residue positions C40; C60; A10; D12; K26; A86; A190; and G275; amino acid residue positions C40; C60; D12; K26; A86; H161; A190; and G275; amino acid residue positions C40; C60; D12; K26; A86; H161; A190; G275; V334 and L361; or amino acid residue positions C40; C60; D12; K26; A86; H161; A190; G275; and V334. Specific illustrative embodiments of these variants include those having amino acid substitutions: D12G, C40A, C60N, A86V, A190T and G275S; D12G, K26E, C40A, C60N, A86V, H161Y, A190T and G275S; or D12G, K26E, C40A, C60N, A86V, H161Y, A190T; G275S and V334F.

One illustrative mutant having a specific constellations of amino acid substitutions is designated GX12 and comprises six mutations: C40A, C60N, A86V, D12G, G275S and A190T. The expression level of soluble LovD, the Michaelis-Menten kinetic constant ($k_{cat}/K_m$) and the whole cell activity of GX12, were then compared to those of the wild type enzyme. GX12 showed a 2.83-fold improvement of the $k_{cat}/K_m$ value, 2.3-fold of the soluble expression level and a 7.5-fold improvement in whole-cell activity at 25° C. Another mutant designated GX27 comprises eight mutations: C40A. C60N, A86V, D12G, G275S, A190T, 11161Y, and K26E. The expression level of soluble LovD, the Michaelis-Menten kinetic constant ($k_{cat}/K_m$) and the whole cell activity of GX27 were then compared to that of wild type enzyme. GX27 showed 3.45-fold improvement of the $k_{cat}/K_m$ value and 4-fold improvement of the soluble expression level, and a 11-fold improvement in the whole-cell activity 25° C.

Embodiments of the invention include polynucleotides encoding the substitution variants disclosed herein, for example an isolated polynucleotide having at least a 95-%100% sequence identity to a polynucleotide encoding a variant LovD polypeptide as disclosed herein. Using a LovD polynucleotide as shown in SEQ ID NO: 5 for example, and a knowledge of codon usage (e.g. as found at page 168 of GENES IV, Oxford University Press, Benjamin Lewin Ed), one can make any substitution variant of the LovD polypeptide disclosed herein such as C40A, for example by altering the codon that codes for a cysteine amino acid at position 40 ("UGC") so that it instead codes for alanine amino acid (e.g. "GCU"). Illustrative embodiments of such methods are shown for example in Example 1. In addition, a wide variety of techniques for generating variant polynucleotides and polypeptides have been well known in the art for many years, for example site-directed mutagenesis (see, e.g. Carter et al., 1986, Nucl. Acids Res. 13:4331; Zoller et al., 1987, Nucl. Acids Res. 10:6487), Related embodiments of the invention include a vector comprising these polynucleotides (e.g. an expression vector including control sequences recognized by a host cell transformed with the vector) as well as host cells comprising such vectors. Optionally, the host cell is an *Escherichia coli, Aspergillus terreus, Monascus ruber, Monascus purpureus, Monascus pilosus, Monascus vitreus, Monascus pubigerus, Candida cariosilognicola, Aspergillus oryzea, Doratomyces stemonitis, Paecilomyces virioti, Penicillum citrinum, Penicillin chrysogenum, Scopulariopsis brevicaulis* or *Trichoderma viride*. A related embodiment of the invention is a process for producing a variant LovD polypeptide comprising culturing a host cell transformed with a encoding a variant LovD polypeptide under conditions suitable for expression of a polypeptide, so that the variant LovD polypeptide is produced. In certain embodiments of the invention, the variant LovD polypeptide can be fused to a heterologous amino acid sequence, for example one that facilitates its manipulation. A variety of such heterologous sequences are known in the art and used in such contexts, for example heterologous polyhistidine sequences that are commonly used to purify polypeptides via a Ni-NTA column.

Yet another embodiment of the invention is a method of making a variant of a LovD polypeptide shown in SEQ ID NO:1 comprising: using a polynucleotide mutagenesis procedure to generate a population of mutants of the LovD polynucleotides; and expressing a population of LovD polypeptide variants encoded by the population of LovD polynucleotide mutants; so that a variant of a LovD polypeptide is made. Optionally, the polynucleotide mutagenesis procedure is a saturation mutagenesis or an error prone polymerase chain reaction procedure. Typically these embodiments of the invention include screening one or more members of the population of LovD polypeptide variants so as to identify a variant that exhibits: a decreased aggregation; an improved thermal stability; an improved acyltransferase activity; an improved kcat/Km value; an improved soluble expression level; and/or an improved whole cell activity at 25° C., as compared to the LovD polypeptide shown in SEQ ID NO:1. Optionally the polynucleotide mutagenesis procedure is controlled so as to generate a substitution mutation at a codon that encodes amino acid residue position: A10; D12; K26; A86; A190; H161; K227; G275; V334; and/or L361. In a related embodiment of the invention, the polynucleotide mutagenesis procedure is controlled so as to generate a variant comprising C40A and C60N; and a further a substitution mutation at a codon that encodes amino acid residue position: A10; D12; K26; A86; A190; H161; K227; G275; V334; and/or L361.

Yet another embodiment of the invention is a method of making simvastatin comprising the steps of: combining together monacolin J; an acyl thioester that donates an acyl moiety to the C8 hydroxyl group of monacolin J in the presence of a LovD acyltransferase variant; and a variant of a LovD acyltransferase polypeptide shown in SEQ ID NO:1, the variant LovD polypeptide comprising: amino acid residue positions C40 and C60; and at least one amino acid residue position: A10; D12; K26; A86; A190; H161; K227; G275; V334; or L361; and then allowing the variant LovD polypeptide to use an acyl group from the acyl thioester to regioselectively acylate the C8 hydroxyl group of monacolin J; so that simvastatin is made. In certain embodiments of the invention, the monacolin J; the acyl thioester and the variant LovD polypeptide are combined in a fermentation media in the presence of an isolated organism that produces the LovD acyltransferase variant wherein the isolated organism is at least one of: *Aspergillus terreus; Aspergillus terreus* that does not express LovF polypeptide of SEQ ID NO: 3; *Escherichia coli*; or *Escherichia coli* that does not express bioH polypeptide of SEQ ID NO: 4. Optionally in such embodiments, the acyl thioester is selected a butyrlyl-thioester, a N-acetylcysteamine thioester or a methyl-thioglycolate thioester; comprises medium chain length (C3-C6) acyl group moieties; and/or is able to cross the cellular membranes of *Escherichia coli* or *Aspergillus terreus* cells growing within a fermentation media (e.g. α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB)).

In the methods for making simvastatin, the isolated organism can be grown under at least one of the following conditions: at a temperature between 25-40° C.; for a time period between at least 4 to at least 48 hours; at a pH between 7-8; and/or in a fermentation media comprising LB, F1 or TB media. Optionally the methods further comprise purifying the simvastatin made by the method by at least one purification step comprising: lysis of cells of an isolated organism present in the combination; centrifugation; precipitation of a free acid form of simvastatin; conversion of a free acid form of simvastatin to a simvastatin salt; filtration; or high performance liquid chromatography (HPLC). In certain embodiments, the method produces a composition of matter comprising 0%-1% of the monacolin J that was initially combined with the acyl thioester that donates an acyl moiety to the C8 hydroxyl group of monacolin J in the presence of A LovD acyltransferase variant; and/or results in at least 95% of the monacolin J added to the combination being converted to simvastatin. Optionally in these methods, the variant LovD polypeptide comprises amino acid substitutions: D12G, C40A, C60N, A86V, A190T and G275S; D12G, K26E, C40A, C60N, A86V, H161Y, A190T and G275S; or D12G, K26E, C40A, C60N, A86V, H161Y, A190T; G275S and V334F. A related embodiment of this invention is a composition of matter comprising: monacolin J; an acyl thioester that donates an acyl moiety to the C8 hydroxyl group of monacolin J in the presence LovD acyltransferase; a variant of a LovD acyltransferase polypeptide shown in SEQ ID NO:1, the variant LovD polypeptide comprising an amino acid substitution at: amino acid residue positions C40 and C60; and at least one amino acid residue position: A10; D12; K26; A86; A190; H161; K227; G275; V334; or L361; and simvastatin.

Yet another embodiment of the invention is a method of making huvastatin comprising the steps of: combining together hydrolyzed pravastatin tetra-ol; an acyl thioester that donates an acyl moiety to the C8 hydroxyl group of hydrolyzed pravastatin tetra-ol in the presence of LovD acyltransferase; and a variant of a LovD acyltransferase polypeptide shown in SEQ ID NO:1, the variant LovD polypeptide comprising an amino acid substitution at amino acid residue position: A10; D12; K26; C40; C60; A86; A190; H161; K227; G275; V334; and/or L361; and allowing the variant LovD polypeptide to use an acyl group from the acyl thioester to regioselectively acylate the C8 hydroxyl group of hydrolyzed pravastatin tetra-ol; so that huvastatin is made. A related embodiment of the invention is a composition of matter comprising: hydrolyzed pravastatin tetra-ol; an acyl thioester that donates an acyl moiety to the C8 hydroxyl group of hydrolyzed pravastatin tetra-ol in the presence LovD acyltransferase; a variant of a LovD acyltransferase polypeptide shown in SEQ ID NO:1, the variant LovD polypeptide comprising an amino acid substitution at amino acid residue position: A10; D12; K26; C40; C60; A86; A190; H161; K227; G275; V334; and/or L361; and huvastatin. Optionally this variant LovD polypeptide comprises amino acid substitutions: D12G, C40A, C60N, A86V, A190T and G275S; D12G, K26E, C40A, C60N, A86V, H161Y, A190T and G275S; or D12G, K26E, C40A, C60N, A86V, H161Y, A190T; G275S and V334F.

As discussed in detail below, the isolated organism can be grown under one of a variety of fermentation conditions known in the art and the exact conditions are selected, for example based upon fermentation parameters associated with optimized growth of a specific organism used in an embodiment of the invention (see, e.g. Miyake et al., Biosci. Biotechnol. Biochem., 70(5): 1154-1159 (2006) and Hajjaj et al., Applied and Environmental Microbiology, 67: 2596-2602 (2001), the contents of which are incorporated by reference). Typically, the organism is grown at a temperature between 30-40° C., for a time period between at least 4 to at least 48 hours. Typically, the organisms are grown at a pH between 6.5-8.5. In certain embodiments of the invention, the pH of the fermentation media can be 6.9, 7.0, 7.1, 7.2, 7.3, 7.4, 7.5, 7.6, 7.7, 7.8, 7.9, 8.0 or 8.1. In illustrative embodiments, the organism is grown in a fermentation media comprising LB, F1 or TB media.

Optionally, the monacolin J that is combined with the other constituents in the methods of the invention is produced by an isolated organism within the fermentation media, for example, one of the organisms listed above that also produces the LovD acyltransferase variant. Alternatively, the monacolin J that is combined with the other constituents in the methods of the invention is produced by a different organism that produces this compound that is added to the fermentation media and grows along with the organism that produces the LovD acyltransferase variant. In another embodiment of the invention, monacolin J is derived from an exogenous source and added to the fermentation mixture. Optionally, the method of the invention produces a composition of matter comprising 0%-1% of the monacolin J that was initially added to the combination. In certain embodiments of the invention, the method results in at least 95% of the monacolin J added to the combination being converted to simvastatin.

In typical embodiments of the invention, acyl thioester that can donate an acyl moiety to the C8 hydroxyl group of monacolin J in the presence of LovD acyltransferase is derived from an exogenous source (e.g. a chemical synthesis process) and added to the fermentation mixture. A variety of such acyl thioesters are disclosed herein. Typically, the acyl thioester is a butyrlyl-thioester, a N-acetylcysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of *Escherichia coli* or *Aspergillus terreus* cells growing within a fermentation media. Typically, the acyl thioester is selected from the group consisting of α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB). In an illustrative embodiment, the acyl thioester is α-dimethylbutyryl-S-methyl-mercaptopropionate that is combined in fermentation media in a concentration range of 1 mM-100 mM.

Certain embodiments of the methods for making simvastatin include further steps to purify simvastatin by the combination. For example, some embodiments of the invention include at least one purification step comprising lysis of cells of an isolated organism present in the combination. Embodiments can include at least one purification step comprising centrifugation of cells or cell lysates of an isolated organism present in the combination. Embodiments can include at least one purification step comprising precipitation of one or more compounds present in the combination. Embodiments can include at least one purification step comprising filtration of one or more compounds present in the combination. Embodiments can include at least one purification step comprising a high performance liquid chromatography (HPLC) analysis of one or more compounds present in the combination.

The disclosure provided herein shows that variety of permutations of these methods can be used to make simvastatin and huvastatin and the like. In certain embodiments of the invention for example, the host organism produces the acyl thioester and/or the monacolin J. Alternatively, the acyl thioester and/or the monacolin J are added to the organism as part of the process for producing simvastatin. The methods can further comprise adding an expression vector having one or more *A. terreus* genes that are known to facilitate the production of simvastatin and/or huvastatin or the like such as the genes that encode SEQ ID NO: 1 (and/or a variant as disclosed herein) or SEQ ID NO: 2 and transforming it into the heterologous host, wherein the polypeptide having the acyltransferase activity is thereby expressed. In another embodiment, monacolin J can be produced from a heterologous host.

Another embodiment of the invention is a method of producing simvastatin from monacolin J in an organism which expresses a LovD acyltransferase gene encoding a variant disclosed herein comprising coculturing this first organism that expresses the LovD acyltransferase variant with a second organism (e.g. in a fermentation mixture) that produces the acyl thioester and/or the monacolin J, wherein the acyl thioester interacts with LovD acyltransferase gene product in the presence of monacolin J to produce simvastatin. Optionally, the first organism is an organism that does not produce lovastatin naturally (e.g. *E. coli* transduced with a gene encoding a LovD acyltransferase variant). Alternatively, the first organism is a lovastatin-producing organism such as *A. terreus* (e.g. *A. terreus* having an inactivated LovF/LDKS gene). The method can further comprise adding one or more exogenous components to the fermentation mixture to increase the production of simvastatin precursors such as monacolin J to thereby increase the production of simvastatin.

The methods of the invention can further comprise adding further components to the fermentation mixture to increase the production of monacolin J and to thereby increase the production of simvastatin and/or huvastatin. As one illustrative embodiment of this method, the component can be a clone with the LovE gene, wherein the organism is transformed with the clone and LovE is translated and thereby the production of simvastatin is increased. As another illustrative embodiment of this method, the component can be a clone containing the D4B segment of the *A. terreus* genome (ATCC accession 98876), wherein the organism is transformed with the clone so that the production of monacolin J is increased.

Yet another embodiment of the invention is a method of converting monacolin J to simvastatin in vitro or in vivo in the presence of an exogenous acyl thioester. Preferably, the acyl thioester is capable of penetrating the cell membrane. In yet another embodiment of the invention, is a method of converting monacolin J to simvastatin directly within the organism in the presence of the acyl thioester wherein the organism produces LovD. In an illustrative embodiment of the invention, the organism is an *A. terreus* having a disrupted LDKS gene.

Yet another embodiment of the invention is a simvastatin product made by a process comprising the steps of combining together monacolin J; an acyl thioester that donates an acyl moiety to the C8 hydroxyl group of monacolin J in the presence of LovD acyltransferase; and a LovD acyltransferase variant; and allowing the LovD acyltransferase variant to use an acyl group from the acyl thioester to regioselectively acylate the C8 hydroxyl group of monacolin J so that the simvastatin product is made. A related embodiment of the invention is a huvastatin product made by a process comprising the steps of combining together hydrolyzed pravastatin tetra-ol; an acyl thioester that donates an acyl moiety to the C8 hydroxyl group of hydrolyzed pravastatin tetra-ol in the presence of a LovD acyltransferase variant; and LovD acyltransferase; and allowing the LovD acyltransferase variant to use an acyl group from the acyl thioester to regioselectively acylate the C8 hydroxyl group of hydrolyzed pravastatin tetra-ol; so that the huvastatin product is made.

Another embodiment of the invention is a method of producing simvastatin comprising hydrolyzing lovastatin into monacolin J in the presence of LovD of SEQ ID NO: 1 or a LovD variant as disclosed herein and acylating monacolin J, wherein said hydrolyzation and acylation produce simvastatin. Another related embodiment of the invention is a method of producing huvastatin comprising pravastatin into hydrolyzed pravastatin in the presence of LovD of SEQ ID NO: 1 or a LovD variant as disclosed herein and acylating a monacolin J variant, wherein said hydrolyzation and acylation produce huvastatin.

Embodiments of the invention include composition of matter used to make and or made by the processes disclosed herein. For example, one embodiment of the invention is a composition of matter comprising monacolin J; an acyl thioester that donates an acyl moiety to the C8 hydroxyl group of monacolin J in the presence a LovD acyltransferase variant. Certain embodiments of these compositions of matter further comprise a LovD acyltransferase variant. Certain embodiments of these compositions of matter further comprise simvastatin. Optionally, the composition further comprises an isolated organism such as *Escherichia coli, Aspergillus terreus, Monascus ruber, Monascus purpureus, Monascus pilosus, Monascus vitreus, Monascus pubigerus, Candida cariosilognicola, Aspergillus ogea, Doratomyces stemonitis, Paecilomyces virioti, Penicillum citrinum, Penicillin chrysogenum, Scopulariopsis brevicaulis* or *Trichoderma viride*. In typical embodiments, the organism in the composition is *Aspergillus terreus* or *Escherichia coli* that expresses LovD polypeptide of SEQ ID NO:1. In one embodiment of the invention the organism is *Aspergillus terreus* that does not express LovF polypeptide of SEQ ID NO: 3. In another embodiment of the invention the organism is *Escherichia coli* that does not express bioH polypeptide of SEQ ID NO: 4. In certain embodiments of the invention, isolated organism within the composition has been transduced with an expression vector encoding *Aspergillus terreus* LovD polypeptide of SEQ ID NO: 1.

A variety of acyl thioesters that can be used in the compositions of the invention are disclosed herein. Typically, the acyl thioester is a butyrlyl-thioester, a N-acetyl-cysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of *Escherichia coli* or *Aspergillus terreus* cells growing within a fermentation media. Typically, the acyl thioester is selected from the group consisting of α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB). In an illustrative embodiment, the acyl thioester is α-dimethylbutyryl-S-methyl-mercaptopropionate that is combined in fermentation media in a concentration range of 1 mM-100 mM and can typically be about 10, 20, 30, 40, 50, 60, 70, 80 or 90 mM. In some embodiments of the invention, the composition further comprises lovastatin and the amount of simvastatin in the composition is greater than the amount of lovastatin in the composition.

As is discussed in detail below, the methods and materials of the invention that are used to make simvastatin can be adapted to produce compounds that are structurally similar to simvastatin, for example huvastatin. In this context, one embodiment of the invention is a method of making huvastatin comprising the steps of combining together hydrolyzed pravastatin tetra-ol; an acyl thioester that donates an acyl moiety to the C8 hydroxyl group of hydrolyzed pravastatin tetra-ol in the presence of LovD acyltransferase; and a LovD acyltransferase variant; and then allowing the LovD acyltransferase use an acyl group from the acyl thioester to regioselectively acylate the C8 hydroxyl group of hydrolyzed pravastatin tetra-ol, so that huvastatin is made. A related embodiment of the invention is a composition of matter comprising: hydrolyzed pravastatin tetra-ol; an acyl thioester that donates an acyl moiety to the C8 hydroxyl group of hydrolyzed pravastatin tetra-ol in the presence LovD acyltransferase; a LovD acyltransferase variant; and huvastatin.

Yet another embodiment of the invention is a composition of matter comprising one or more of the huvastatin precursors, for example, hydrolyzed pravastatin tetra-ol or 6-hydroxyl-6-desmethylmonacolin J in the presence of thioester selected for its ability to acylate the C8 hydroxyl group of monacolin J or a monacolin J variant such as hydrolyzed pravastatin tetra-ol. Typically, such compositions can further include an organism as discussed above. Consequently, embodiments of the invention include processes for making simvastatin or huvastatin composition of matter substantially as herein disclosed and exemplified.

In situations where a modified organism that produces simvastatin (e.g. *A. terreus* with a disruption in the LDKS gene) also produces lovastatin (e.g. some minimal residual amount), the methods and materials disclosed herein allow the manipulation of the biochemical pathways/processes in the organism so that simvastatin or a related compound such as huvastatin is the predominant product of these pathways. A related embodiment is a composition of matter comprising an organism and simvastatin and/or huvastatin produced by that organism, wherein the amount of simvastatin and/or huvastatin in the composition is greater than the amount of lovastatin in the composition.

A related embodiment of the invention is a composition of matter comprising a LovD variant as disclosed herein, hydrolyzed pravastatin, and an acyl thioester. In illustrative embodiments, the composition of matter comprises an *E. coli* that produces huvastatin. In related embodiments, the composition of matter is an *A. terreus* (e.g. *A. terreus* with a disruption in the LDKS gene) that produces huvastatin. In situations where a modified organism that produces huvastatin (e.g. *A. terreus* with a disruption in the LDKS gene)

also produces lovastatin (e.g. some minimal residual amount), the methods and materials disclosed herein allow the manipulation of the biochemical pathways/processes in the organism so that huvastatin is the predominant product of these pathways. A related embodiment is a composition of matter comprising an organism and huvastatin produced by that organism, wherein the amount of huvastatin in the composition is greater than the amount of lovastatin in the composition.

In certain embodiments of the invention, further components and/or methodological steps can be combined with one or more of the methods and materials discussed above. For example, the methods can further comprise using high cell-density fermentation to increase the effective concentration of LovD acyltransferase and optimise fermentation conditions and/or increasing LovD acyltransferase catalytic efficiencies towards the one or more acyl thoiesters via protein engineering. Many other components or methods can be used to increase the production of simvastatin or of an intermediary compound that facilitates the production of simvastatin.

As disclosed herein, an "acyl thioester to regioselectively acylate the C8 hydroxyl group of monacolin J" is a compound having an acyl group that can be transferred to monacolin J or a related compound so as to make simvastatin or a related compound using LovD and/or a LovD variant as disclosed herein. A wide variety of such agents are known in the art that are further shown herein to have this activity (see, e.g. the illustrative acyl-thioesters in Table 1). In addition to those known in the art and further shown by the instant disclosure to have this activity, any potential acyl donor/carrier known in the art (or synthesized de novo) that further has an ability to acylate C8 of monacolin J so as to produce simvastatin can be easily identified by comparative experiments with the acyl donors disclosed herein (e.g. acyl-SNAC). Typically in such experiments, the acyl thioester is a butyrlyl-thioester, a N-acetylcysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of *Escherichia coli* or *Aspergillus terreus* cells growing within a fermentation media. Typically, the acyl thioester is selected from the group consisting of α-dimethylbutyryl-S-methylmercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB).

As shown by the instant disclosure, the nature of the instant invention allows one to readily identify a compound as a "acyl thioester to regioselectively acylate the C8 hydroxyl group of monacolin J" with minimal experimentation. In one illustrative procedure for identifying a compound as a "acyl thioester to regioselectively acylate the C8 hydroxyl group of monacolin J", a first step is to make a mixture of monacolin J and *A. terreus*. In a second step, this mixture is then combined with a test compound in a fermentation mixture and allowed to grow. In a third step, the mixture is then tested for the presence of simvastatin, for example by using a HPLC analysis, wherein the presence of simvastatin identifies the compound as having this activity. In view of the high throughput screening methodologies known in this art (see, e.g. Kittel et al., *Metab. Eng.* 2005, 7(1): 53-58, which is incorporated herein by reference), such methods can be performed on a large number of test samples so as to easily determine where and which species of acyl donor compounds possess a utility that allows them to be used in the embodiments of the invention disclosed herein.

Embodiments of the invention also include articles of manufacture and/or kits designed to facilitate the methods of the invention. Typically such kits include instructions for using the elements therein according to the methods of the present invention. Such kits can comprise a carrier means being compartmentalized to receive in close confinement one or more container means such as vials, tubes, and the like, each of the container means comprising one of the separate elements to be used in the method. For example, one of the containers can comprise a vial, for example, containing a plasmid encoding a LovD variant as disclosed herein, optionally within a microbial host such as E. *Coli* or *A. terreus* (e.g. *A. terreus* having a disruption in the LDKS gene) and another vial containing an acyl-SNAC compound or the like, both of which can be added to a fermentation mixture to produce simvastatin.

In a typical embodiment of the invention, an article of manufacture containing materials useful for production of simvastatin is provided. The article of manufacture comprises a container and a label. Suitable containers include, for example, bottles, vials, syringes, and test tubes. The containers may be formed from a variety of materials such as glass or plastic. The container can hold a composition of matter (e.g. an acyl carrier and an organism) which can produce simvastatin, for example. The label on, or associated with, the container indicates that the composition is used for examining cellular polypeptides. The article of manufacture may further comprise a second container comprising another compound or substrate for addition to the fermentation mixture for example. This compound or substrate, for example, might be used to increase the production of certain intermediaries in the production of simvastatin, such as monacolin J. It may further include other materials desirable from a commercial and user standpoint, including other buffers, diluents, filters, needles, syringes, and package inserts with instructions for use.

Further biological aspects of the invention are discussed in the following sections.

Biochemical Aspects of Embodiments of the Invention

An appreciation of certain aspects of the invention is facilitated by discussions of biochemical aspects of LovD. In the immediately following sections, the LovD acyltransferase is the *A. terreus* LovD polypeptide shown in SEQ ID NO: 1, and is typically referred to as "LovD" or the "LovD enzyme". As shown in the Examples below, LovD variants are useful in contexts in which wild type LovD is used. Portions of these sections discuss previously known biochemical aspects of wild type LovD (e.g. those disclosed in International Publication No. WO 2007/139871) in order to more clearly demonstrate the utility of embodiments of the invention disclosed herein.

In International Publication No. WO 2007/139871, the promiscuity of the LovD enzyme towards alternative acyl donors was demonstrated. This disclosure teaches that the acyl carrier/donor does not need to be attached to the LDKS. Alternative thiol containing carriers are suitable, including acyl-CoA (coenzyme A) and more importantly, the membrane permeable acyl-SNAC. LovD does not need to interact with LovF and can accept an acyl group from a variety of different donors. Moreover LovD can transfer a variety of acyl substrates to the C8-hydroxyl group of monacolin J to yield an assortment of lovastatin analogs. LovD can regioselectively acylate the C8 hydroxyl position in monacolin J with a variety of acyl substrates. Amongst the successful acyl groups is α-dimethylbutyryl-SNAC, which yields simvastatin in the presence of LovD and monacolin J. The transacylation activity of LovD has been confirmed in vitro and can be reconstituted in a heterologous host. LovD directly acylates monacolin J with α-dimethybutyrate to yield the pharmaceutically important simvastatin. α-Dimethylbutyryl-SNAC is cell-permeable. The cell permeable properties of α-dimethylbutyryl-SNAC has an important implication: the compound can be supplied as a precursor in vivo to an organism, such as a prokaryote or an eukaryote, expressing LovD. The prokaryote or eukaryote, when fermented in the presence of monacolin J (either made endogenously, or supplied exogenously to the fermentation media) can directly afford simvastatin. E. coli, for example, can be used as a microbial host for the bioconversion of monacolin J into simvastatin. In International Publication No. WO 2007/139871, both monacolin J and dimethylbutyryl-SNAC were added to a growing culture of an E. coli strain overexpressing the LovD enzyme, with simvastatin then being isolated from the fermentation broth of the culture in good yield.

As noted above, LovD can catalyze the final acyl transfer step during lovastatin biosynthesis and can regiospecifically acylate the C8 hydroxyl group in monacolin J. LovD can display broad substrate specificity towards the decalin aglycon, the acyl carrier, and the acyl group. When supplemented with the unnatural substrate α-dimethylbutyryl-SNAC, LovD can produce the pharmaceutically important simvastatin both in vitro and in vivo. When an α-dimethylbutyryl-thioester precursor is supplied to a LovF-deficient strain of A. terreus, the lovastatin biosynthetic pathway can be redirected to afford simvastatin directly.

International Publication No. WO 2007/139871 teaches the tolerance of LovD towards different acyl substituents by performing the transacylation assay with various commercially available acyl-CoAs. Assays were performed with 1 mM monacolin J, 4 mM acyl-CoA and 10 uM LovD for 10 hours. The results clearly indicate LovD polypeptide displays preference towards medium chain length (C3-C6) acyl groups with butyryl-CoA being the optimal alkylacyl-CoA substrate. The bulkier benzoyl-CoA was one of the best acyl substrate examined, with nearly 70% conversion of simvastatin to the corresponding 8-benzoxy-lovastatin analog (apparent $k_{cat}$=0.16 min$^{-1}$). Introducing α-β unsaturation significantly decreased the reaction rate, as seen in the 6% acylation of monacolin J in the presence of crotonyl-CoA. Acetoacetyl-CoA and β-hydroxylbutyryl-CoA were both excellent substrates of LovD, in good agreement with the isolation of monacolin X (see, e.g., A. Endo, K. et. al. J. Antibiot, 1986, 38, 321-327) and monacolin M (see, e.g., A. Endo, D. et. al., J. Antibiot. 1986, 39, 1670-1673) from the natural host, respectively. Among the CoA substrates assayed, LovD was inactive towards malonyl- and palmitoyl-CoA.

International Publication No. WO 2007/139871 further examined the substrate specificities of LovD towards alternative acyl carriers, especially those that are simpler to prepare synthetically, and can penetrate cell membrane under in vivo conditions. N-acetylcysteamine thioesters (SNAC) have been used extensively as probes and precursors in studying natural product biochemistry (see, e.g. Auclair et al., Science, 1997, 277, 367-369). Methyl-thioglycolate (SMTG) was recently shown to be a cost-effective substitute for SNAC in the precursor-directed biosynthesis of erythromycin (see, e.g., S. Murli, K. S. et. al., Appl. Environ. Microbiol. 2005, 71, 4503-4509). Both SNAC and SMTG thioesters substituted for butyryl-CoA efficiently, with apparent $k_{cat}$ values of 0.09 min and 0.23 min$^{-1}$, respectively, further highlighting that protein-protein interactions between LovD and LovF, as well as the interaction between LovD and the phosphopantetheine arm are not required for acyl transfer.

International Publication No. WO 2007/139871 teaches that synthesized α-S-methylbutyryl-SNAC and α-dimethylbutyryl-SNAC can be used in assays for the in vitro chemoenzymatic synthesis of lovastatin and simvastatin, respectively. The results are shown in FIG. 8 of International Publication No. WO 2007/139871. This disclosure teaches that the natural, α-S-methylbutyrate side chain was surprisingly a poorer substrate compared to butyryl-, pentanoyl- and hexanoyl-SNAC. The apparent $k_{cat}$ (~0.04 min$^{-1}$) of lovastatin synthesis is more than 50% slower than that of LovD towards butyryl-SNAC. This provides evidence that the wild type LovD has not been optimized towards transferring the branched substrate. Addition of a second methyl substituent at the α-position further attenuated the rate of acylation, likely attributed to the increased steric hindrance of the dimethyl moiety. This disclosure in International Publication No. WO 2007/139871 in combination with the disclosure provided herein provides evidence that LovD can be mutated towards desirable properties such as those relating to transferring the branched substrate, decreased aggregation; an improved thermal stability; an improved catalytic activity; an improved $k_{cat}/K_m$ value; an improved soluble expression level; and/or an improved whole cell activity at 25° C. (e.g. using the directed protein evolution methods such as those disclosed in Example 2 below).

Throughout this application, various publications are referenced. The disclosures of these publications are hereby incorporated by reference herein in their entireties.

EXAMPLES

The Examples below provide illustrative methods and materials that can be used in the practice the various embodiments of the invention disclosed herein. Skilled artisans are aware that aspects of this technology that can be adapted for use with embodiments of the invention disclosed herein are taught in International Publication No. WO 2007/139871; Xie et al., Chem Biol. 2006 13(11):1161-9; Xie et al., Appl Environ Microbiol. 2007 April; 73(7):2054-60; Xie et al., Biotechnol Bioeng. 2009 1; 102(1):20-8; Xie et al., J Am Chem Soc. 2009; 131(24):8388-9; and Gao et al., Chem Biol. 2009 Oct. 30; 16(10):1064-74; the contents of each of which are incorporated by reference.

Example 1

Site-Directed Mutagenesis of LovD Leads to Elevated Whole-Cell Simvastatin Production This Example demonstrates how site-directed mutagenesis of LovD leads to LovD variants capable of elevated whole-cell simvastatin production.

In this Example, we use site-directed mutagenesis to improve the solubility of LovD. The resultant mutant A1N3 was more efficient than the wild type in the whole cell experiment. We also optimized the High-cell-density fermentation to produce more recombinant proteins in shorter time to increase the whole cell LovD activities, which can be served as a platform to produce simvastatin in large scale. Combined optimization on LovD protein and fermentation gave us much higher simvastatin production than before, and the ~20 g/L yield of simvastatin can be an attractive alternative to current multi-step methods.

Briefly, when using the *Escherichia coli* bioH deficient strain YT2/pAW31 as the whole cell biocatalyst, the overexpressed acyltransferase, LovD, catalyzed the conversion of 15 mM Monacolin J (MJ) acid and 18 mM DMB-S-MMP to simvastatin acid in 12 hours. SDS-PAGE analysis of LovD showed that more than half of the LovD protein in *E. coli* was expressed insolubly, and the native gel study of LovD showed that recombinant expression of LovD formed ~20% oligomer even at high DTT concentration. To determine the cysteine residues responsible for oligomerization, each of the nine cysteines in LovD was substituted for alanine by site directed mutagenesis to create nine mutants (named A1-A9). The results indicated that seven out of the nine cysteines are essential for the intact monomer structure of LovD, while the first and third cysteines may form intermolecular disulfide bonds leading to oligomerization. Further study on these mutants showed that breaking intermolecular disulfide bonds (A1 and A3) increased the solubility of the resultant protein and improved whole cell bioconversion (defined as activity). Due to the higher activity of A1 and A3, we further explored the effects of other residues on these two sites such as Ser (S), Thr (T), Asn (N), and Glu (Q). We found that A1 and LovD C60N (N3) have higher whole cell activity than the other mutants at the relevant sites. Both mutants showed ~25% higher activity than the wild type. As we expected, the double mutant A1N3 combined the benefit of the two mutations and gave the highest whole cell activity, with ~50% improvement when compared to the wild type. When using YT2/A1N3 as the whole cell biocatalyst, optimized high-cell-density fermentation study showed that the mutant can completely (>99.5%) convert 45 mM MJ acid to simvastatin acid within 18 hours, while under the same conditions the wild type YT2/pAW31 can only reach 91% conversion even with prolonged time (26 hours). Equipped with the mutant A1N3 and the optimized fermentation method, the whole process can be easily scaled up for industrial production of simvastatin.

Materials and Methods
General Procedures

*E. coli* XL-1 Blue (Stratagene) were used for the DNA cloning. The substrates Monacolin J (MJ) acid, and DMB-S-MMP were prepared as described previously (see, e.g. Xie et al., 2007; Appl Environ Microbiol 73: 2054-2060). YT2 was used as protein expression host. All reagents were purchased from standard sources. Analysis of compounds were performed with HPLC with a reverse phase C18 column (Alltech Apollo 5u, 150 mm×4.6 mm); linear gradient: 60% CH3CN in water (0.1% trifluoroacetic acid [TFA]) to 95% CH3CN in water (0.1% TFA) for 10 min, and the flow rate was 1 ml/min.

Site-Directed Mutagenesis:

LovD C40A (A1), C49A (A2), C60A (A3), C72A (A4), C89A (A5), C216A (A6), C266A (A7), C380A (A8), C395A (A9), C40S (S1), C60S (S3), C40T (T1), C60T (T3), C40N (N1), C60N (N3), C40Q (Q1), C60Q (Q3) mutations were created by site directed mutagenesis using pAW31 as template DNA and the primers listed below. Double mutant A1N3 was created by using A1 as template, LovD_C60A_PvuII_F and LovD_C60A_PvuII_R as primers. Most primers were designed by directly changing the codon sequence to desired amino acid codon sequence, while some were introduced one restriction site by silent mutation for easy cloning. The introduced mutations were verified by DNA sequencing.

Only the forward primers are listed below. The reverse primers are the reverse complement of the forward primers. F denotes forward primers. The number shows the position of the mutated amino acid. The characters before and after the number show that the amino acid before change and after change. The bordered bases correspond to the genetic codes for amino acids to be mutated.

```
LovD_C40A_NheI_F:
                                        (SEQ ID NO: 6)
ATCATGGCCCGAGATGCTAGCGGCAATCTAAATTAT;

LovD_C49A_MluI_F:
                                        (SEQ ID NO: 7)
TCTAAATTATACGCGTGCCTTCGGGGCTCGGAC;

LovD_C60A_MfeI_F:
                                        (SEQ ID NO: 8)
GTGCGACGGGACGAGGCCAATCAATTGCCGCCGCTACAGGTC;

LovD_C72A_F:
                                        (SEQ ID NO: 9)
CAGGTCGACACCCCGGCCCGGCTCGCCAGTGC;

LovD_C89A_F:
                                        (SEQ ID NO: 10)
TCATGGCCCTACAAGCCATGGAGCGCGGTCTC;

LovD_C216A_F:
                                        (SEQ ID NO: 11)
CTGCAGGAGAATATCGCTGCGCCGCTGGGCAT;

LovD_C266A_F:
                                        (SEQ ID NO: 12)
GCCGATGGAGAGGAGGCCTTCGGCGGCCAGG;

LovD_C380A_F:
                                        (SEQ ID NO: 13)
CCCAAAGCCGGCCTGGCCACCCTTGCGTTCTT;

LovD_C395A_F:
                                        (SEQ ID NO: 14)
TGGAATGACCCGGTCGCTCGTGATCTGACACG;

LovD_C40S_F:
                                        (SEQ ID NO: 15)
GGTCATCATGGCCCGAGATTCCAGTGGCAATCTAAATTATA;

LovD_C60S_F:
                                        (SEQ ID NO: 16)
GACGGTGCGACGGGACGAGTCCAATCAGCTGCCGCCGCTAC;

LovD_C40T_SpeI_F:
                                        (SEQ ID NO: 17)
CGGTCATCATGGCCCGAGATACTAGTGGCAATCTAAATTATAC;

LovD_C60T_F:
                                        (SEQ ID NO: 18)
GGACGGTGCGACGGGACGAGACCAATCAGCTGCCGCCGCTAC;

LovD_C40N_F:
                                        (SEQ ID NO: 19)
CGGTCATCATGGCCCGAGATAACAGTGGCAATCTAAATTATA;

LovD_C60N_F:
                                        (SEQ ID NO: 20)
GGACGGTGCGACGGGACGAGAACAATCAGCTGCCGCCGCTAC;

LovD_C40Q_F:
                                        (SEQ ID NO: 21)
CGGTCATCATGGCCCGAGATCAGAGTGGCAATCTAAATTATAC;
```

-continued and

LovD_C60Q_F:

(SEQ ID NO: 22)
GGACGGTGCGACGGGACGAG[CAG]AATCAGCTGCCGCCGCTACA.

Ep-PCR and Construction of Mutant Library

Ep-PCR procedure was modified from established protocols. The reaction consisted of 0.35 mM dATP, 0.4 mM dCTP, 0.2 mM dGTP, 1.35 mM dTTP, 4 mM MgCl$_2$, 0.25 mM MnCl$_2$, and 2.5 U Taq polymerase. The reaction mixture was submitted to 25 cycles PCR: 94° C. for 1 min, 55° C. for 1 min and 72° C. for 3 mins. The resulting PCR products were digested with DpnI, further digested with EcoRI and NdeI, and ligated to pET28(a). The ligation mixture was transformed to YT2 and plated on LB agar containing 35 mg/L kanamycin.

Protein Expression and Purification:

Each mutant was transformed into *E. coli* YT2 strain and selected by Kanamycin (Kan). The transformant was grown in 500 ml LB-Kan media at 37° C. to OD$_{600}$ 0.4~0.6, then 0.1 mM IPTG was added to induce protein expression at 20° C. for 16 hours. Cells were collected by centrifugation, resuspended in 30 ml Buffer A (50 mM Tris-HCl, pH 8.0, 2 mM DTT, 2 mM EDTA), and lysed by sonication. Cell debris and insoluble proteins were removed by centrifugation (16,000 g, 4° C., 1 h). To the cleared lysate, 2 ml of Ni-NTA resin (Qiagen) was added. Each mutant was purified using a step gradient of buffer A with increasing concentration of imidazole. Pure (>95%) LovD proteins were eluted in buffer A containing 250 mM imidazole, and then buffer exchanged into buffer A without imidazole. Glycerol was added to a final concentration of 10%, the proteins were aliquoted, and flash frozen.

Whole-Cell Biocatalysis:

Whole-cell catalytic synthesis of simvastatin acid from MJ acid and DMB-S-MMP were performed as described (see, e.g. Xie et al., 2007; Appl Environ Microbiol 73: 2054-2060). The LovD wild type and all mutants were cultured side-by-side for comparison. A single colony of the freshly transformed strains was used to inoculate a 5 ml LB culture supplemented with 35 mg/L kan and grown overnight at 37° C. The next morning, 100 μl of the overnight culture (0.2%) was inoculated into 50 ml LB medium with Kan. When OD$_{600}$ reached 0.4~0.6, 0.1 mM IPTG was added to the culture and expression of LovD was performed at 20° C. for 16 hrs. To mimic the high density fermentation conditions, the cells were concentrated 10-fold before addition of substrates. A 14 ml aliquot of the culture was collected by centrifugation (4° C., 4000 g, 10 min). The cell pellet was gently resuspended in 1330 ml of the supernatant, followed by addition of 70 ml of a MJ acid stock solution (300 mM in water) to make final concentration 15 mM. The concentrated culture was then resuspended and separated into seven 200 μl samples, 1 μl of pure DMB-S-MMP was added to each sample (final concentration ~20 mM). The cultures were then shaken at 300 rpm at room temperature. At each time point, a total extraction was performed by adding 10 μl of 20% SDS to completely lyse the cells, followed by liquid-liquid extraction with 500 μl EA/2% TFA. The organic phase was removed, evaporated, and redissolved in 500 μl ACN for HPLC analysis.

Selection of High Activity Mutants (Screening)

*N. crassa* was grown on SDA slants for 10 days and spores were harvested with 1% Tween-80. 100 ml of molten SDA was seeded with 0.3-0.5×10$^8$ spores and poured into a 230×230 mm plate. Colonies from mutation library were cultured in 96 well plates containing 250 μl LB medium (with 35 mg/L kanamycin). The cells were grown at 37° C. to saturation and transferred to duplicated plates. Protein expression was induced with 0.1 mM IPTG at OD$_{600}$ of 0.5 and the expression was performed at 25° C. for 16 h. 5 mM MJA and 10 mM DMB-SMMP were added to initiate the reaction. After a certain reaction time (45 mins to 4 hours depending on the activity of the parent), cells were removed with centrifugation (2,000 g, 4° C., 5 min). The amount of supernatant spotted on the SDA plate was typically 1~3 μl. The plates were incubated at 30° C. for 16~18 hours. The improved mutants were selected following visual comparison of the inhibition zones.

Determining Whole-Cell Biocatalysis Activity

Wild type LovD and all mutants were cultured in parallel for comparison. A single colony of the freshly transformed YT2 competent cells was used to inoculate a 5 mL LB culture supplemented with 35 mg/L kanamycin. Following overnight growth at 37° C., 100 μl of the culture was inoculated into 50 mL LB medium supplemented with 35 mg/L kanamycin. When OD$_{600}$ reached 0.4~0.6, 0.1 mM IPTG was added to the cultures and expression of all LovD variants was performed at 25° C. for 16 hr. To mimic the high density fermentation conditions, the cells were then concentrated 10-fold before addition of substrates. A 10 ml aliquot of each culture was collected by centrifugation (4° C., 2,000 g, 10 min). The cell pellet was gently resuspended in 1 ml of the medium supernatant, followed by addition of 70 μl of MJA (300 mM stock) to a final concentration of 15 mM. The concentrated culture was then divided into seven 200 μl aliquots and 1 μl of pure DMB-SMMP was added to each sample to a final concentration of 20 mM. The small cultures were then shaken at 300 rpm at 25° C. At each time point, a complete extraction of one culture aliquot was performed by adding 10 μl of 20% SDS for cells lysis, followed by extraction with 500 μl ethyl acetate containing 1% trifluoroacetic acid TFA. The organic phase was removed, evaporated, and redissolved in 500 μl acetonitrile for HPLC analysis. The whole-cell activity was determined by fitting the linear regions of the conversion time course plot.

T$_M$ Measurement by Circular Dichroism (Thermostability)

Samples were prepared by adding 50 μg of proteins to 250 μl 10 mM Tris-HCl buffer (pH 7.0). The sample was placed in a quartz cuvette with a 1 cm path length and heated in a Peltier-controlled cell at a rate of 1° C. per min. Ellipticity was monitored at 222 nm in a Jasco spectropolarimeter (Jasco Inc., Easton, Md.). The midpoint of the denaturation curve was determined with Microcal Origin 5.0 software (OriginLab Corporation, Northampton, Mass.).

Kinetic Assay of LovD Wild Type and Mutants:

To obtain K$_m$ values for MJ acid and k$_{cat}$, the DMB-S-MMP concentration was fixed at 2 mM, while the concentration of MJ acid was varied from 0.25 mM to 2 mM. Dimethyl sulfoxide (DMSO) was added to a final concentration of 10% to facilitate the solubilization of DMB-S-MMP. To compare the turnover rate of all mutants and the wild type protein, the MJ acid concentration was set at 1 mM and the DMB-S-MMP was set at 2 mM, the protein concentration was fixed at 10 uM, after the reaction was performed at room temperature for 2 hours, the reaction was quenched by adding EA/2% TFA. The organic phase was dried and redissolved in ACN for HPLC analysis.

High Density F1 Fed-Batch Fermentation

We used the same method described in our previous paper with some modification (see, e.g. Pfeifer et al., 2002; Appl Environ Microbiol 68(7):3287-92). Vitamin solution except biotin was excluded from both inoculation minimal media and fermentation media because the YT2 strain which has bioH gene knocked out requires biotin to grow normally. The strain YT2/pAW31 or YT2/A1N3 was grown overnight in 5 ml LB medium (with 35 mg/L kan) at 37° C. and 250 rpm, 1 ml overnight culture was used to inoculate a 100 ml F1 medium (with 35 mg/L kan). The F1 medium was grown for another 12 hours, a 25 ml aliquot was spun down, and the cell pellet was resuspended in 10 ml F1 medium and inoculated into a 2.5-liter Applikon Biobundle vessel containing 1 liter of F1 medium. The cells were grown at 37° C., the pH was maintained at 7.1 throughout the experiment with 2 M HCl and half concentrated NH4OH. The agitation rate and air flow rate were adjusted to maintain the dissolved oxygen (DO) level above 20%, typically the agitation maintained at 1200 rpm and the aeration was controlled at 0.4~0.5 liters/min. As soon as the glucose was consumed in the fermentor, which was indicated by a fast increase in DO level, a peristaltic pump delivered 0.3 ml/min of the feed solution to the fermentor. When the $OD_{600}$ reading reached 20, the temperature of the fermentation was decreased to 25° C. by cooling water, 0.5 mM IPTG was added to the fermentor to induce protein expression. The protein expression was maintained for another 12 hours, then the feeding and aeration were stopped, agitation was decreased to 250 rpm and pH was gradually adjusted to 7.8, both substrates MJ acid and DMB-S-MMP were added to the fermentor to initiate the bioconversion. MJ acid was dissolved in water (adding NaOH to help dissolve) to make a final concentration of 500 mM, DMB-S-MMP was added pure. The feeding rate was controlled at 4.0 mM/h (MJ acid) to minimize the disturbance of the cells and finished in about 10 hours. HPLC was used during the whole process to check the rate of the conversion.

Purification and Downstream Process

When the conversion was complete or reached at equilibrium, 20 g SDS was added to the fermentor and stirred for 30 min to completely lyse the cells, the pH was adjusted to 5.0 by adding 6M HCl and stirred for 10 mins, 1 L ethyl acetate (EA) was added and stirred for another 30 min to extract the product. The mixture was poured into a separation funnel and waited for about 1 hour and separated. The water phase was extracted again with 1 L EA. The EA phase was combined (~2 L) and concentrated by rotor vapor to around 500 ml, the EA solution was then washed with saturated NaCl aqueous solution and dried by anhydrous $Na_2SO_4$ and filtered. The EA solution was concentrated to a final volume of 150 ml and treated with 50% saturated NH4OH and 50% methanol to a final pH=9.6. The solution was kept at 4° C. for 1 hour and filtered through filter paper and washed with EA extensively to give white solid, which was dried under vacuum overnight and weighed. The purity of the final product was determined by HPLC.

Experimental Results

Two of the nine mutants showed higher whole cell activity after alanine scanning mutagenesis (see, e.g. Morrison et al., 2001; Curr Opin Chem Biol 5(3):302-7):

LovD protein was purified to homogeneity by one step Ni-NTA column (FIG. 2a). From the native gel of wild type lovD, we found that even at high DTT concentration, ~20% of the LovD protein still formed oligomer. The disulfide bonds between the proteins are spurious for protein crystallization because the monomer and oligomer are different species (see, e.g. Nemoto et al., 2006; J Appl Physiol 100(5):1688-91). One of our purposes was to remove the intermolecular disulfide bonds. By replacing the cysteine residues with alanine, we hope the resultant LovD mutant can keep the acyl-transferase activity while breaking the intermolecular disulfide bonds. We also found that more than 50% of the expressed LovD protein was insoluble when overexpressed in E. coli. We reasoned that the solubility of LovD may be changed when the intermolecular disulfide bonds between wild type LovD was eliminated (see, e.g. Lindberg et al., M. 2004; Proc Nati Acad Sci USA 101(45): 15893-8).

There are nine cysteines in LovD protein at the position of C40, C49, C60, C72, C89, C216, C266, C380, C395 (C1-C9). First we used homolog analysis to identify which of the nine cysteine residues are likely to be surface exposed, and might therefore form undesirable disulfide bonds. By using the EstB esterase as a template which has moderate sequence homology of ~20% (see, e.g. Wagner et al., 1997; Acta Crystallogr D Biol Crystallogr 53(Pt 5):596-8), five cysteines C1, C2, C3, C7, and C9 were found to be possible residues forming the responsible disulfide bond. We mutated all nine cysteine residues to alanine one by one to create nine single mutants named A1-A9. The sequence of the mutants was verified by DNA sequencing.

We ran the native gel of all the mutant proteins together with the wild type LovD protein (FIG. 2b). From the native gel, A3 formed almost all monomers, and A1 had slightly more monomers compared to the wild type LovD protein. The rest mutants didn't change the percentage of oligomer while some mutants such as A4, A5 and A7 were not very stable and formed inclusion body fast. A9 produced no soluble proteins at all. The results indicated that only the first and third cysteines may form intermolecular disulfide bonds leading to oligomerization.

Figure 3:
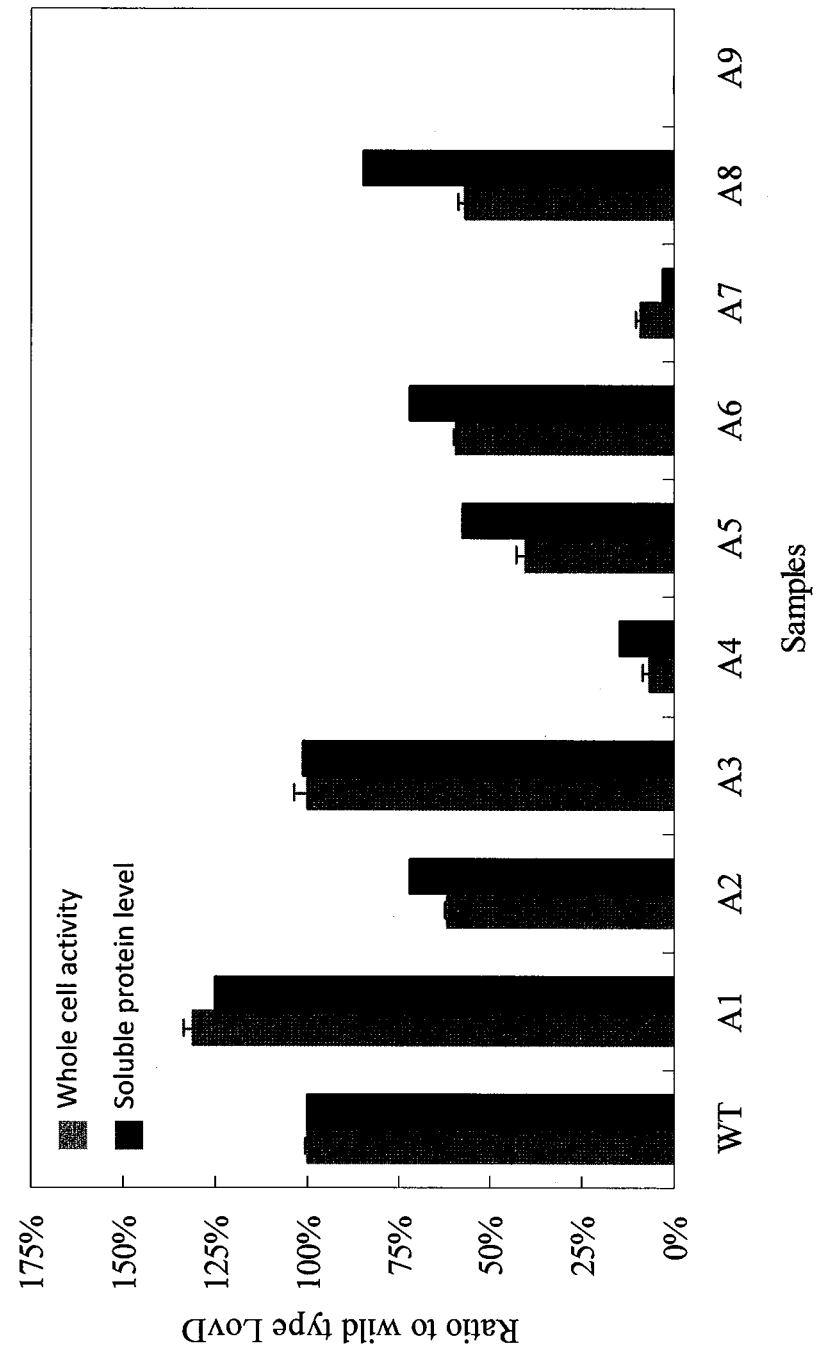
FIG. 3. Whole cell biocatalytic activities based on the conversion from MJ acid and DMB-S-MMP (gray column) and soluble protein expression level comparison between the wild type LovD and the mutants (black column). For the whole cell activity, the LB culture was concentrated 10 times to mimic high density fermentation, 15 mM MJ acid and 18 mM DMB-S-MMP were used to compare the conversion. The conversion based on 8 hours was used to compare the whole cell activity between the wild type LovD and the mutants. The wild type LovD conversion was normalized to 100%, the data points are averaged values of two runs. For the protein expression level assay, protein was expressed and purified using Ni-NTA Column from 50 ml LB culture. The concentration was determined by Bradford assay. Also the wild type LovD expression level was normalized to 100%. The whole cell activities of the mutants were proportional to the soluble expressed proteins, so the solubility may be the only reason attributed to the whole cell activities.

We then tested the in vivo activity of the nine mutants in comparison to the wild type LovD. Both the mutants and the wild type LovD strains were grown in LB media, expressed and concentrated 10 times to mimic the high density fermentation after 16 hours expression at 20° C. Both MJ acid and DMB-S-MMP were added to final 15 mM and 18 mM respectively to start the reaction. At 8 hours, 100 µl sample culture was taken out to check the total conversion from MJ acid to simvastatin acid. FIG. 3 showed relative activities of all the mutants compared to the wild type, the wild type conversion was normalized to 100° A. From the results we can see that most of the mutations were unfavorable and showed lower whole cell activity (A2, A4-A8) or no activity (A9). We reason that those cysteines may form intramolecular disulfide bonds which stabilize the structure of the protein. Most of the mutants likely disrupted the intramolecular disulfide bond, loosing the 3-dimenstional structure of the protein and making the protein unstable to form inclusion bodies (see, e.g. Wakabayashi et al., 2007; J Biol Chem 282(38):27841-6). The results gave us an idea on which cysteine stabilized the structure of protein and which cysteine was not helpful on stabilizing the structure. A1 showed highest activity among all the mutants with ~25% improved activity based on conversion compared to the wild type, and A3 has slightly higher activity compared to the wild type. The C9 position is crucial for LovD stability because there was no soluble protein can be detected when A9 was expressed.

The Higher Whole Cell Activity was Due to Higher Solubility

There are three possibilities that could contribute to the higher whole cell activity. One is that the mutants are more soluble compared to the wild type, another is that the mutants have higher turnover rate than the wild type LovD, or a combination of both. To discover why A1 and A3 showed higher activities in the whole cell experiment while the others lost activities, we measured the protein expression level of all the mutants. All nine mutants and the wild type LovD proteins were purified at the same time and under the same conditions. The proteins were purified from 50 ml LB culture. LovD was eluted in the last fraction which contains 250 mM imidazole. The concentration of the last fraction was determined by Bradford Assay using BSA as the standard. Interestingly, we found that the ratio of the soluble protein between the mutants and the wild type was consistent with the ratio of the conversion between the mutants and the wild type (FIG. 3). The solubility of A1 was 28% more than the wild type while the conversion rate of A1 at the 8 hours time point was 31% higher than the wild type. FIG. 3 showed that the different solubility of the mutant proteins may be the only reason for different whole cell activities.

To further prove that the whole cell activity of LovD mutants was caused by different solubility of the protein, an in vitro assay was used to determine the $k_{cat}$ and $K_m$ of LovD mutants. The concentration of DMB-S-MMP was fixed at 2 mM and MJ acid concentration was varied from 0.25 mM to 2.0 mM. The $k_{cat}$ of LovD wild type, and selected mutants A1, A3 were determined as 0.62, 0.62, and 0.64 min$^{-1}$, the $K_m$ of MJ acid were 0.64, 0.68, and 0.66 mM respectively. The kinetic constants between these three enzymes showed that there was actually no difference between them. For the rest LovD mutant proteins, we only checked the conversion of one time point. The assay fixed MJ acid and DMB-S-MMP concentration at 1 mM and 2 mM, LovD proteins are fixed at 10 uM, a 2 hours' conversion showed that they have the same turnover rate. In the whole cell experiment, the concentration of both substrates were much higher than $K_m$ of MJ acid and DMB-S-MMP, so the whole cell activity was only related to the $k_{cat}$ and the amount of soluble protein. The in vitro kinetic assay further confirmed that the different whole cell activity was only due to different solubility of the mutants.

Double Mutation A1N3 Showed Highest Whole Cell Activity

Figure 4:
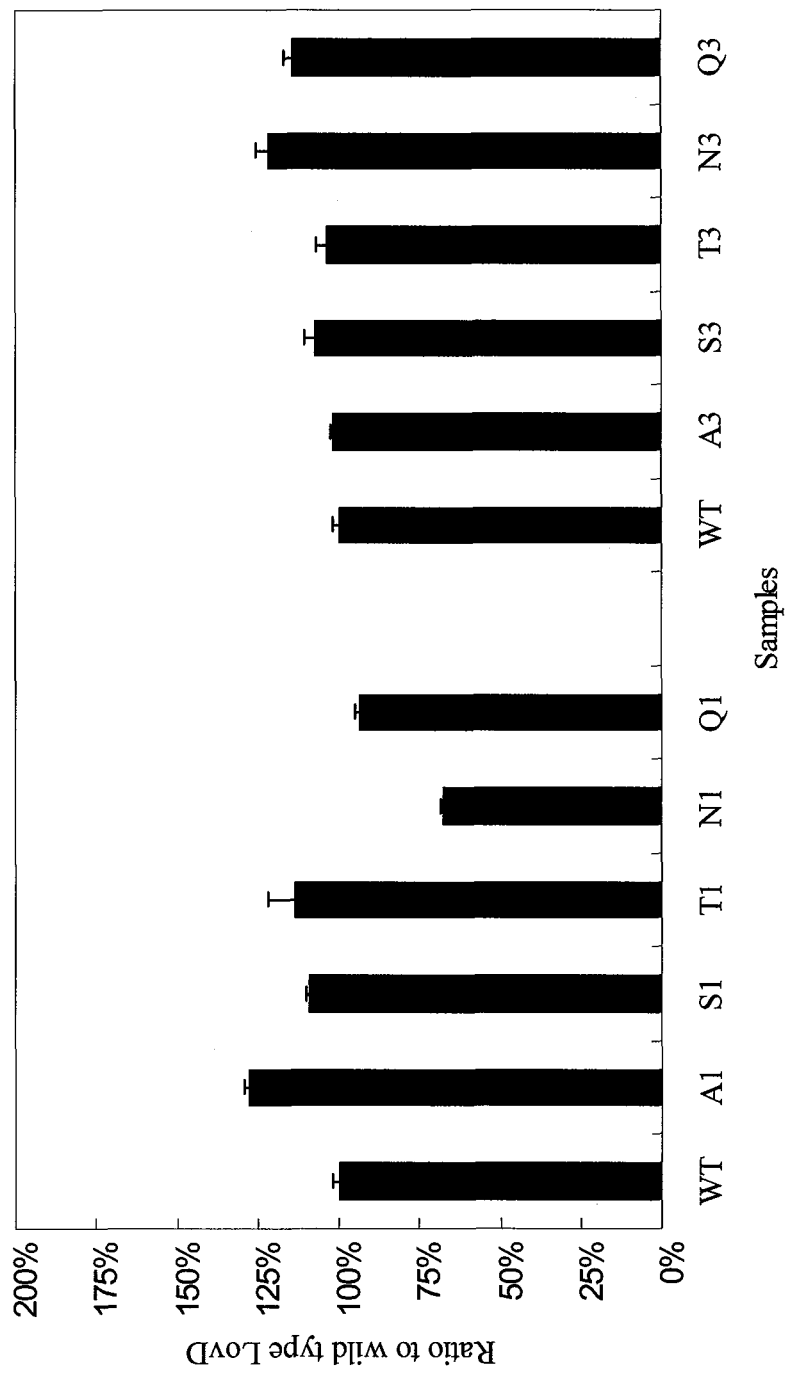
FIG. 4. Whole cell LovD activity between the mutants with the first or the third cysteine changed and the wild type LovD based on 8 hours conversion. The wild type LovD conversion was normalized to 100%, the data points are averaged values of two runs. A1 showed higher conversion than the other mutants at the first cysteine position while N3 was the highest at the third cysteine position. Both A1 and N3 showed ~25% higher whole cell activity compared to the wild type.
Figure 5:
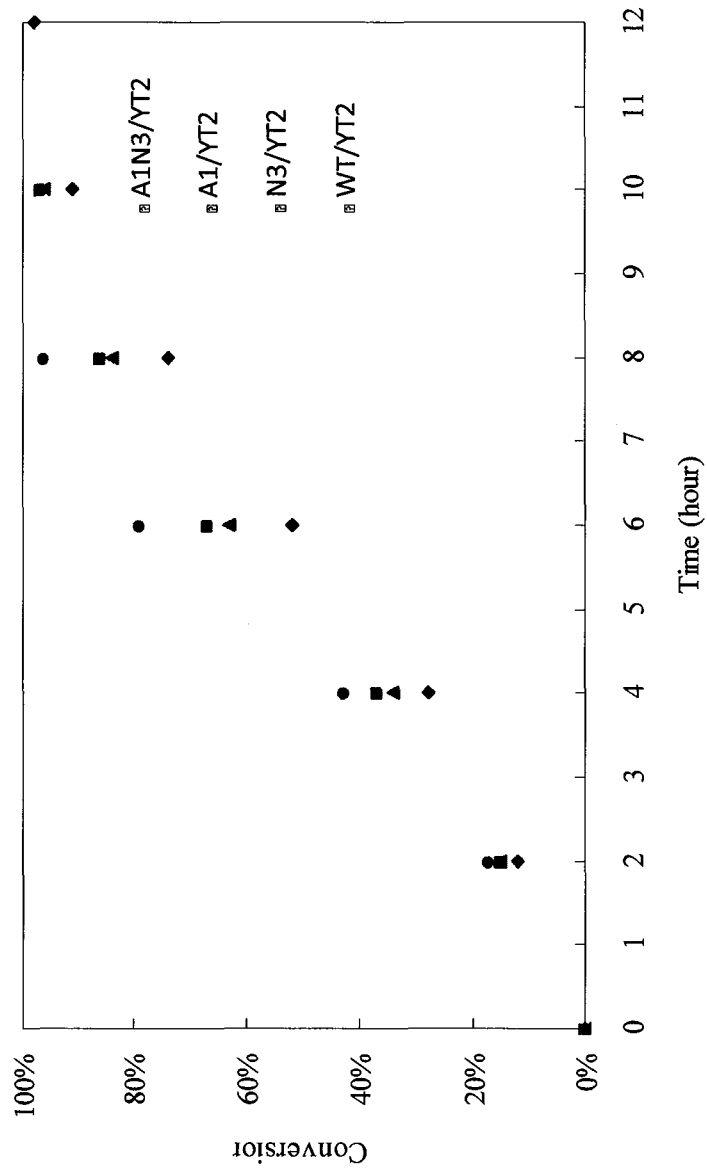
FIG. 5. Simvastatin conversion as a function of time. Assay conditions are the same as before. YT2/A1N3 (●) is the fastest mutant by combining the benefits of A1 and N3, the conversion was finished in 8 hours. Both YT2/A1 and YT2/N3 completed reaction in 10 hours with slightly higher conversion of YT2/A1 than YT2/N3. YT2/pAW31 is the wild type which converted 15 mM MJ acid in 12 hours. The higher whole cell activity resulted in short reaction time. Both YT2/A1 and YT2/N3 reduced ~20% time compared to wild type while YT2/A1N3 reduced ~50% time.

After alanine scanning mutagenesis, we found that the first and the third cysteine substitutes showed higher activity compared to the wild type. We reason that further exploration on these two sites may give better mutants. Due to the different physical properties and size between cysteine, which is polar and slightly larger, and alanine, which is nonpolar and smaller, we changed cysteine to other amino acids such as serine (S), threonine (T), asparagine (N), glutamine (Q). The mutants were derived with the same site-directed mutation methods and named as 51, S3, T1, T3, N1, N3, Q1, and Q3 respectively. We used the same in vivo experiment to check the whole cell activities of all the mutants. The conversion showed that A1 still had the highest activity at the first position while N3 had the highest activity at the third position (FIG. 4). Both mutants have ~25% improvements according to 8 hours conversion. We then combined the two mutations to create a double mutant A1N3 through site-directed mutation. In FIG. 5, we drew the time course of LovD wild type, A1, N3, and A1N3. The assay used the same conditions described before and we checked conversion every two hours. As we expected, A1N3 combined the beneficial properties of the two mutations and completed the reaction in ~8 hours. A1N3 was about 50% faster than the wild type and about 20% faster than the single mutant A1 and N3. In vitro assay and protein expression level experiments also demonstrated that the higher activity of the double mutant A1N3 was due to the higher solubility of the protein. The results of the double mutant A1N3 showed that the mutations at different position of the protein are synergistic (see, e.g. Geddie et al., 2004; J Biol Chem 279(25):26462-8).

High-Cell-Density Fermentation

Figure 6:
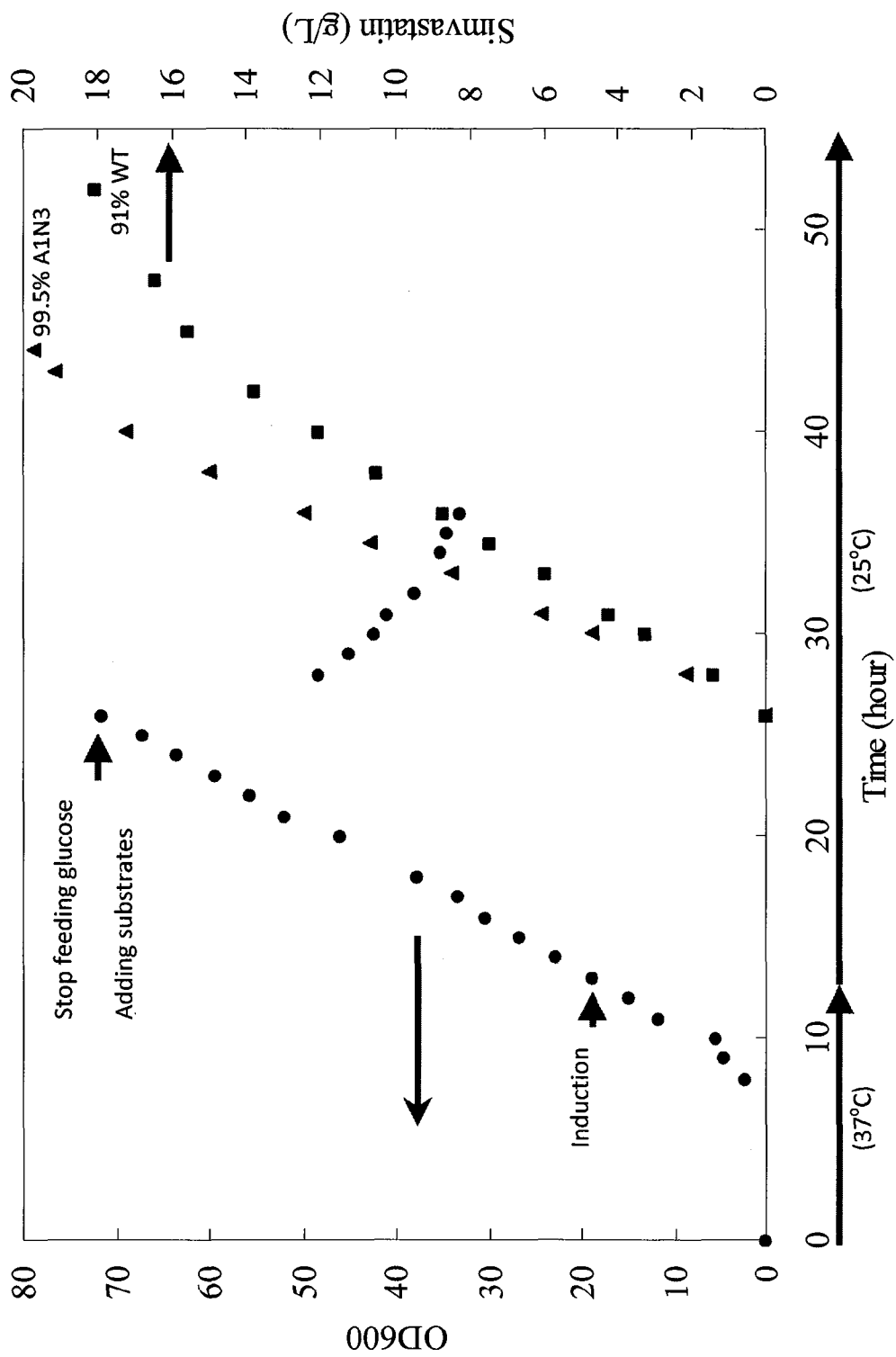
FIG. 6. High-cell-density fermentation of YT2/pAW31 and YT2/A1N. For both strains, the cells were first grown at 37° C. to $OD_{600}$ around 20, then the temperature was cooled to 25° C. and 500 µl 1M IPTG was added to induce protein expression. After the protein was expressed for ~12 hours, glucose feeding was stopped, pH was adjusted to 7.8, 15 g MJ acid and 15 ml DMB-S-MMP were added slowly to start bioconversion. The conversion was checked by HPLC, once the reaction was completed or constant, the reaction was stopped. Simvastatin was recovered by downstream purification process. The great drop on the cell density was happened after substrates addition which can be minimized by slow addition of the substrates. The conversion rate kept constant at first and slowed down with prolonged time which could be inactivation of the LovD proteins.

Our final goal was to prove that our process can be used in large scale simvastatin production, so we optimized the high-cell-density fermentation and tested both the wild type LovD and the double mutant A1N3. Both glucose limitation (glucose as the limited source) and DO limitation (dissolved oxygen as the limited source) were studied to compare the whole cell activities (see, e.g. Qoronfleh, 1999; Appl Biochem Biotechnol 80(2):107-20). We found that the specific LovD activity from glucose limitation was much higher than the activity from DO limitation even though they have very similar $OD_{600}$ reading, possibly due to the accumulation of glucose and acetate which affected the cell growth and recombinant protein expression. So during our fermentation, we kept DO level above 20% to minimize the glucose and acetate concentration. We also found that expression at 25° C. gave the highest whole cell activity. Increasing temperature resulted in more LovD precipitation while decreasing temperature resulted in slow cell growth and required longer expression time. Another important factor related to the whole cell activity of LovD was the pH value. The cells were grown and expressed at pH=7.1, which was not efficient for the reaction. A pH at 7.8 gave the highest whole cell activity in turning MJ acid into simvastatin acid, so before adding substrates, we gradually increase pH to 7.8. Substrates addition was also very important during the conversion. High concentration of MJ acid and DMB-S-MMP were harmful to the cells, so we added both substrates slowly to minimize the disturbance of the cells. Slow addition of substrates to the fermentor still resulted in a prompt decrease in the optical density of the cells (FIG. 6). After the substrates were added to the fermentor, HPLC was used to track the formation of simvastatin acid. It took 18 hours for YT2/A1N3 to completely convert 45 mM MJ acid to simvastatin acid while YT2/pAW31 had 91% conversion in 26 hours. Even with prolonged reaction time, the conversion by pAW31/YT2 cannot be increased. The average reaction rate was 2.5 mM/h for YT2/A1N3 and 1.6 mM/h for YT2/pAW31, which means the double mutant was 150% more efficient in whole cell activity than the wild type during large scale fermentation.

During downstream purification process, the cells were completely lysed to release the product because almost half of the product remained in the cells. It is hard to recover pure simvastatin either in acid form or in lactone form directly from the culture broth, we recovered the product in ammonium salt form. After the cells were lysed, the pH was adjusted to 5.0 slowly to avoid localized high concentration of HCl to make simvastatin lactone form. After the product was extracted by EA and concentrated, 50% methanol and 50% saturated NH4OH mixture was added to the EA solution to convert simvastatin acid simvastatin ammonium salt (SAS). Once SAS was formed, the salt will precipitate out from EA phase. SAS was dried overnight and weighed to calculate the yield. For this best mutant A1N3, the highest MJ acid amount we can add to completely convert to simvastatin was 45 mM. Addition of more substrates resulted in lower final conversion. Starting with 45 mM MJ acid in one liter fermentor, 36 mmol SAS can be finally recovered from the cell broth. The total yield from MJ acid to SAS was 80%. Most of the loss was during the extraction steps. With the optimization on the recovery process and further improvement of the protein, more products can be recovered and the total yield will be higher.

In conclusion, we explored each of the nine cysteines in LovD by alanine scanning mutagenesis. We found that two of the nine cysteines (C1 and C3) are responsible for intermolecular disulfide bonds formation, and that the rest cysteines are important for stabilizing the structure of the protein (C2, C4-C8). C9 is essential for LovD to fold correctly to become soluble. Two mutants, A1 and A3, showed higher whole cell activities because they were more soluble than the wild type. Different residue substitutes at the first position and the third position showed that A1 and N3 have faster conversion than the other mutants. Double mutant A1N3 showed the highest activity among all the mutants which means the two mutations acted synergistically. After optimization on High-cell-density fermentation, we compared the reaction rate of LovD wild type and mutant A1N3 using F1 minimal media. The mutant YT2/A1N3 showed improved ability and can convert 45 mM MJ acid to simvastatin acid in 18 hours, while the wild type YT2/pAW31 took longer time and can only reach 91% at the same conditions. We used random mutagenesis and DNA shuffling approaches to further improve the thermostability and turnover rate of LovD based on A1N3.

Example 2

Directed Evolution and Structural Characterization of a Simvastatin Synthase

This Example demonstrates how site-directed mutagenesis of LovD leads to LovD variants capable of elevated whole-cell simvastatin production.

In this Example, we employed directed protein evolution (see, e.g. Arnold et al., (1999) Curr. Opin. Chem. Biol. 3, 54-59) to improve the SV synthase activity of LovD. After seven rounds of screening, LovD mutants with significantly improved catalytic activities and higher thermal stability were isolated. In parallel, seven X-ray crystal structures including the parent LovD G0, an improved mutant G5, and the co-crystal structures of G5 with MJA, LVA and SVA were obtained. The crystal structures provide atomic resolution details regarding the mechanism of catalysis, substrate and product binding, protein-protein interactions with LovF, and a likely explanation for the effects of beneficial mutations on catalysis.

Figure 7:
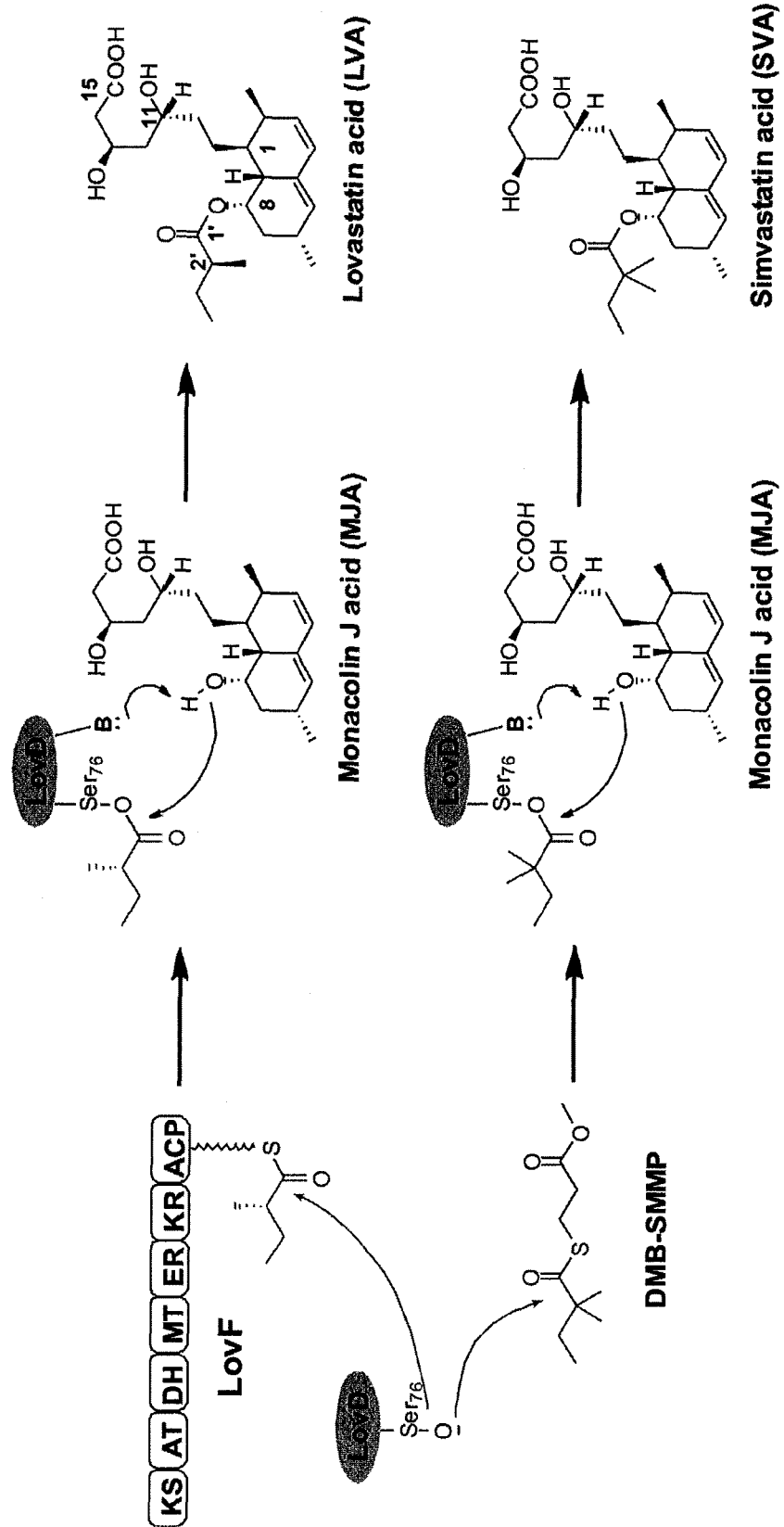
FIG. 7. Reactions catalyzed by LovD. LovD is responsible for converting MJA into LVA via acylation of the α-S-methylbutyrate side chain and can also synthesize SVA using DMB-SMMP as an acyl donor.

Tailoring enzymes found in natural product biosynthetic pathways catalyze a wide array of reactions, including acyltransfer (see, e.g. Loncaric et al., (2006) Chem. Biol. 13, 309-317), glycosylation (see, e.g. Zhang et al., (2006) Science 313, 1291-1294), hydroxylation (see, e.g. Rix et al., (2002) Nat. Prod. Rep. 19, 542-580) and halogenation (see, e.g. Neumann et al., (2008) Chem. Biol. 15, 99-109). A number of these enzymes decorate biologically inactive precursors into pharmaceutically active molecules via regioselective and stereoselective transformations. As a result, tailoring enzymes are attractive candidates as biocatalysts towards synthesis of semisynthetic derivatives and drug libraries (see, e.g. Zhou et al., (2008) Curr. Opin. Biotechnol. 19, 590-596). LovD is an acyltransferase found in *Aspergillus terreus* and is responsible for converting the inactive precursor monacolin J acid (MJA) into the cholesterol-lowering drug lovastatin (LV, acid form lovastatin acid: LVA) via acylation of the α-S-methylbutyrate side chain (see, e.g. Kennedy et al., (1999) Science 284, 1368-1372 and Xie et al., (2006) Chem. Biol. 13, 1161-1169) (FIG. 7). The importance of the hydrophobic α-S-methylbutyryl side chain for binding of LVA to HMG-CoA reductase has been structurally confirmed (see, e.g. Istvan et al., (2001) Science 292, 1160-1164). Chemical modification of the LV side chain to α-dimethylbutyrate yielded the semisynthetic derivative simvastatin (SV, acid form simvastatin acid: SVA), which is the active pharmaceutical ingredient in the blockbuster drug Zocor® (see, e.g. Hoffman et al., (1986) J. Med. Chem. 29, 849-852). Semisynthesis of SV from LV is a multiple-step chemical process and is therefore an intensely pursued target for devising an efficient biocatalytic approach (see, e.g. Morgan et al. WO 2005040107 and Berg et al. WO 2007147801). As a result, LovD is a prime candidate to serve as such a biocatalyst.

LovD is a 413-amino acid protein predicted to have an α/β hydrolase fold based on primary sequence analysis (see, e.g. Kennedy et al., (1999) Science 284, 1368-1372). Among enzymes of known structure that are homologous to LovD is cephalosporin esterase, EstB (PDB ID 1CI9, 26% sequence identity) from *Burkholderia gladioli* (see, e.g. Wagner et al., (2002) Protein Sci. 11, 467-478). The likely general base Tyr188, as well as a conserved SXXK (SEQ ID NO: 24) patch that contains the active site nucleophile Ser76, were indicated through alignment of LovD with EstB (FIG. 8A) (see, e.g. Petersen et al., (2001) J. Biotechnol. 89, 11-25). During LVA biosynthesis, the α-S-methylbutyrate side chain is synthesized by the lovastatin diketide synthase (LDKS) LovF, and is then transferred by LovD regioselectively to the C8 hydroxyl of MJA via an unprecedented polyketide offloading mechanism (see, e.g. Xie et al., (2009) J. Am. Chem. Soc. 131, 8388-8389). The protein-protein interaction between LovD and the acyl carrier protein (ACP) domain of LovF facilitates this highly efficient tailoring reaction in *A. terreus*. We have previously explored the substrate promiscuity of LovD and have shown that it can also synthesize SVA by using the small molecule substrate α-dimethylbutyryl-S-methyl-mercaptoproprionate (DMB-SMMP) as an acyl donor (see, e.g. Xie et al., (2007) 73, 2054-2060) (FIG. 7). Using *Escherichia coli* as an expression host, a whole-cell biocatalytic platform for converting MJA to SVA was established that can produce SVA with low throughput (see, e.g. Xie et al., (2007) 73, 2054-2060). However, as with many enzymes that have been removed from their natural context, LovD is catalytically suboptimal as a biocatalyst and suffers from poor thermal stability (see, e.g. Arnold, F. H. (2001) Nature 409, 253-257). The catalytic activity of SVA synthesis using DMB-SMMP is attenuated ~1,300 fold when compared to the natural substrate attached to LovF (see, e.g. Xie et al., (2009) J. Am. Chem. Soc. 131, 8388-8389), indicating there is ample opportunity for optimization by protein engineering efforts. Furthermore, the structural basis of LovD function and substrate selection had not been elucidated, limiting our ability to rationally optimize the binding of the unnatural dimethylbutyryl substrate and improve LovD efficiency as a SV synthase.

As discussed below, we employed directed protein evolution (see, e.g. Arnold et al., (1999) Curr. Opin. Chem. Biol. 3, 54-59) to improve the SV synthase activity of LovD and then characterize the crystal structures of these LovD variants to provide atomic resolution details regarding the mechanism of catalysis, substrate and product binding, protein-protein interactions with LovF, and a likely explanation for the effects of beneficial mutations on catalysis.

Results

Development of an Agar-Based Diffusion Screening Method

Figure 9A:
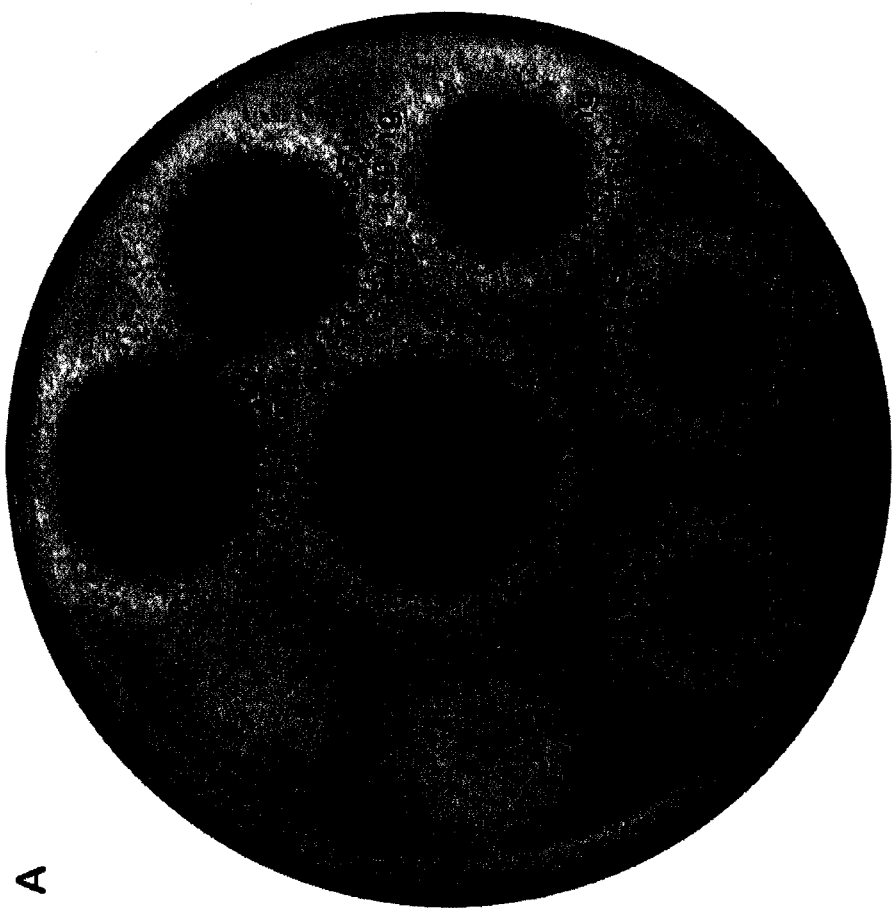
FIGS. 9A-B. Directed evolution of LovD as a simvastatin synthase.

We developed a high throughput screening method to assay for *E. coli* expressing LovD mutants with improved properties in the synthesis of SVA from MJA and DMB-SMMP. The assay relied on the growth inhibition of *Neurospora crassa* by statins, a property that was previously exploited in the screening of high LV producing *A. terreus* strains (see, e.g. Kumar et al., (2000) J. Microbiol. Methods 40, 99-104). We found that SVA can inhibit the growth of *N. crassa* at sub-microgram quantities, while inhibition by MJA requires hundred milligram quantities. To demonstrate the sensitivity and feasibility of the assay, an *E. coli* culture expressing wild type LovD was supplied with 10 mM MJA and 15 mM DMB-SMMP. At different time points, 2 µL aliquots were directly spotted on a Sabouraud's dextrose agar (SDA) plate embedded with *N. crassa* at a density of 0.3~0.5×$10^8$ spores/L. After 16 hours of incubation at 30° C., different inhibition zones were observed for samples containing different degrees of conversion of MJA to SVA (as verified by HPLC) (FIG. 9A). Based on this screening strategy, any significant contribution to whole cell LovD activity, such as improvements in solubility, catalytic efficiency and stability can lead to a detectable phenotypical change.

Screening of LovD Variants with Enhanced Whole Cell Activities

Figure 9B:
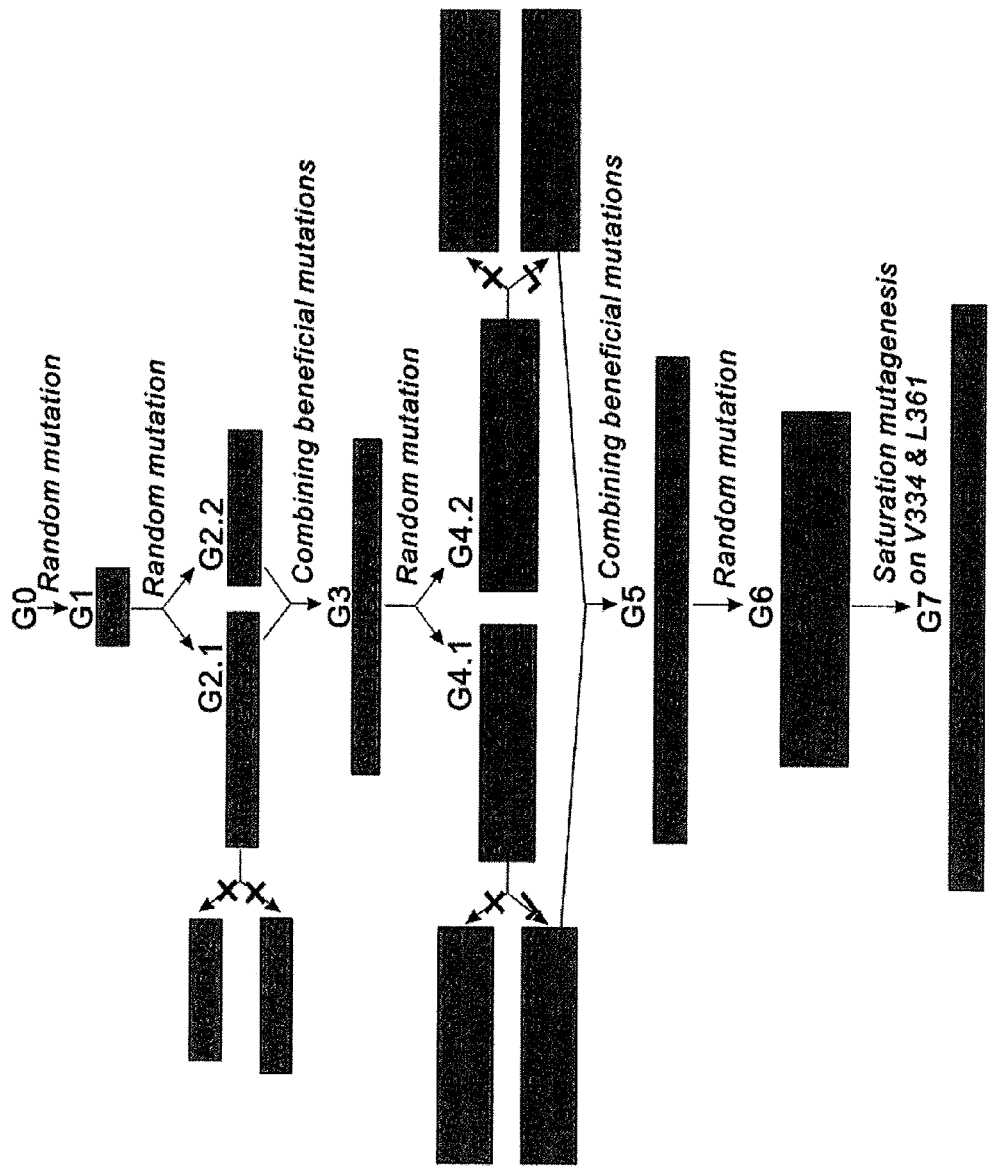

The starting LovD (generation zero or G0) used in directed evolution is the previously characterized double mutant C40A/C60N (see, e.g. Xie et al., (2009) Biotechnol. Bioeng. 102, 20-28). G0 was rationally engineered to be less prone to disulfide-mediated aggregation and was used for crystallization studies (see, e.g. Xie et al., (2009) Biotechnol. Bioeng. 102, 20-28). The mutant libraries were created by either saturation mutagenesis or error-prone Polymerase Chain Reaction (ep-PCR) that generated an average of 2.5 amino acid changes per round (see, e.g. Fromant et al., (1995) Anal. Biochem. 224, 347-353). During each round of screening, the mutant library was ligated into pET28(a) and electroplated into YT2 competent cells (see, e.g. Xie et al., (2007) Metab. Eng. 9, 379-386). The individual mutants were cultured in 96-well plates, followed by induction of LovD expression, addition of MJA and DMB-SMMP, and spotting onto *N. crassa* embedded plates. FIG. 13 shows the gradual improvement in whole cell activity obtained following four rounds of ep-PCR (G1, G2, G4, G6), one round of saturated mutagenesis (G7), and two iterations of combining individual beneficial mutations (G3, G5), with the best mutant G7 displaying ~11 fold increase in whole cell activity as a SV synthase compared to G0 (FIG. 9B). The mutant G2.1 contains amino acid changes at D12G and G275S. Construction of the corresponding single mutants using G1 as template showed that D12G alone had a large negative effect, while G275S alone had a weak positive effect compared to G1. This result suggests the two mutations in G2.1 act synergistically to enhance LovD activities. Combination of mutations from G2.1 and the A190T mutation in G2.2, which was recovered from the same round of ep-PCR, yielded the next generation mutant G3. Ep-PCR using G3 as a template yielded G4.1 and G4.2, each containing a different double mutation combination of A10V/K26E and H161Y/K227R, respectively. Site directed mutagenesis confirmed that both A10V and K227R had negative effects on the activities of LovD. Removal of these mutations and combination of K26E and H161Y yielded an improved mutant G5, which was ~6-fold improved in whole cell activity compared to G0. At this point, structural studies were performed on the G5 mutant to provide insights into the accumulated beneficial mutations. In parallel, an additional round of ep-PCR afforded G6 that contained the beneficial mutations V334D and L361M. Saturation mutagenesis was employed to optimize the combined effects of mutations at positions 334 and 361. The best mutant recovered was G7, of which the whole cell activity was increased an additional 20%. Surprisingly, we found that while position 334 was altered to phenylalanine, the previously deemed beneficial L361M mutation reverted back to leucine. Site-directed mutation of L361M in G7 confirmed that leucine was indeed the more favorable residue in the context of the V334F mutation.

In Vitro Characterization of LovD Variants

Figure 14:
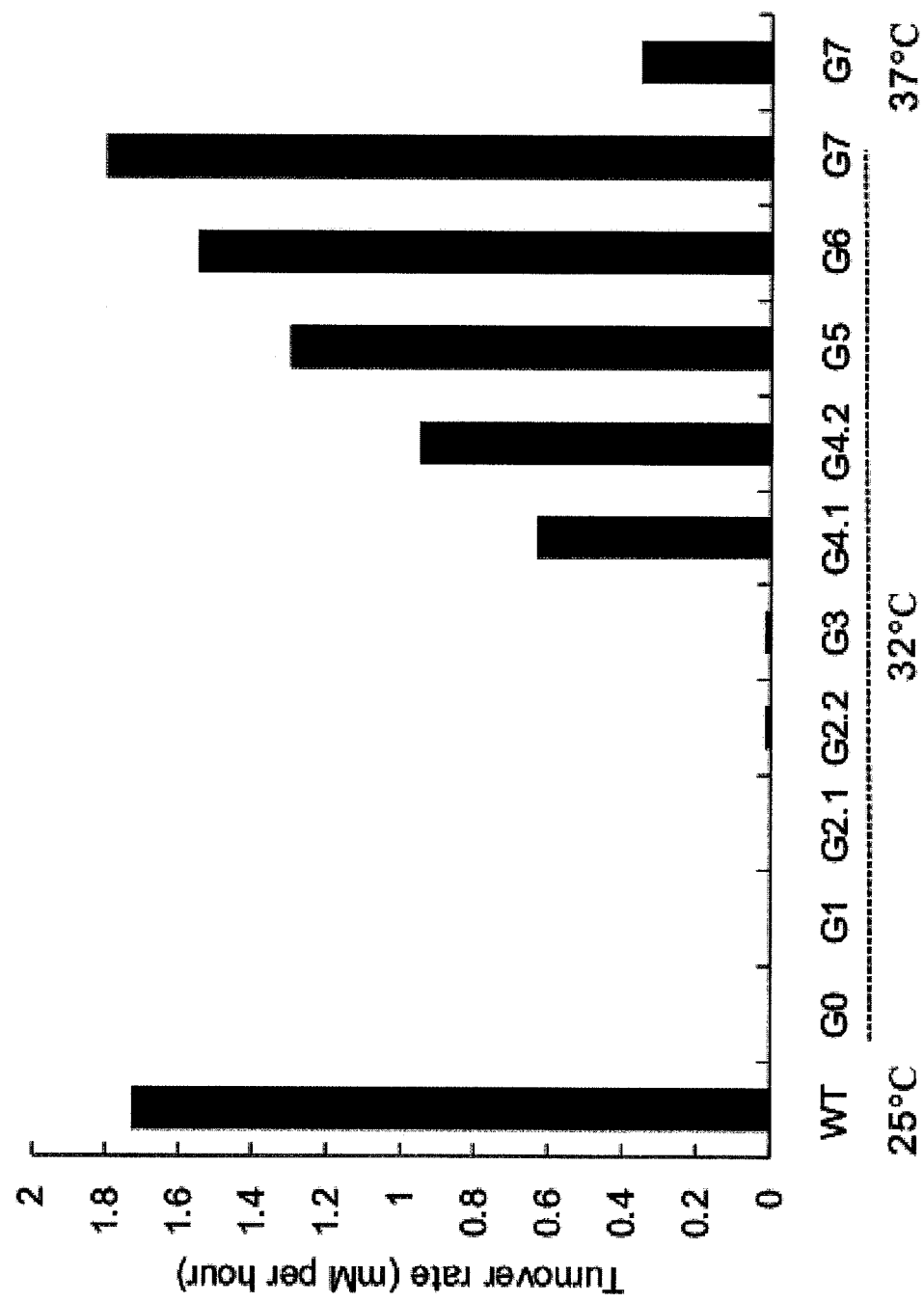
FIG. 14. Whole cell activity of LovD G0 and mutants. At 25° C., the G0 produces SVA at a rate of ~1.7 mM per hour. At 32° C., G0, G1, G2.1, G2.2, and G3 did not show any activity. G7 showed a slightly higher activity compared to the WT at 25° C. At 37° C., only G7 retained residual activity of ~0.4 mM SVA per hour.

To dissect the contributions that led to the increases in whole cell activity, kinetic parameters ($k_{cat}$, $K_M$), soluble protein levels and thermal stability of all the improved mutants were characterized and listed in FIG. 13. The binding affinities ($K_M$) of LovD mutants toward MJA and DMB-SMMP were each within a narrow range (0.7 mM to 0.9 mM for MJA and 0.6 mM to 0.7 mM for DMB-SMMP). The lack of improvement in $K_M$ towards either substrate is not surprising considering the high concentrations of substrates used in the screening assay (~10 $K_M$ of MJA and DMB-SMMP). The observed improvements in whole cell activity are mainly due to increases in the $k_{cat}$ of the mutants and levels of soluble proteins. The $k_{cat}$ and soluble protein levels were simultaneously increased ~3 fold and ~1.5 fold from G1 to G3, respectively. Impressively, the protein expression levels of G3 reached 205 mg/L. In contrast, improvements in $k_{cat}$ were the sole contribution to the increases in whole cell activities from round 4 to round 7. Most notably, a single V334F mutation from G5 to G7 nearly doubled the catalytic turnover rate. In addition, increases in thermal stability were reflected in the whole cell activities of the mutants when expressed at elevated temperatures (FIG. 14). Whereas the G0-G3 mutants have no detectable activity when expressed at 32° C., the later generation mutants retained significant SV synthase activities, with the G7 mutant exhibiting comparable activity to that of G0 at 25° C. Furthermore, the G7 mutant remained active even when expressed at 37° C. The increased thermal stabilities of the mutants have important practical implications in using LovD as a biocatalyst for SV semisynthesis.

Figure 15:
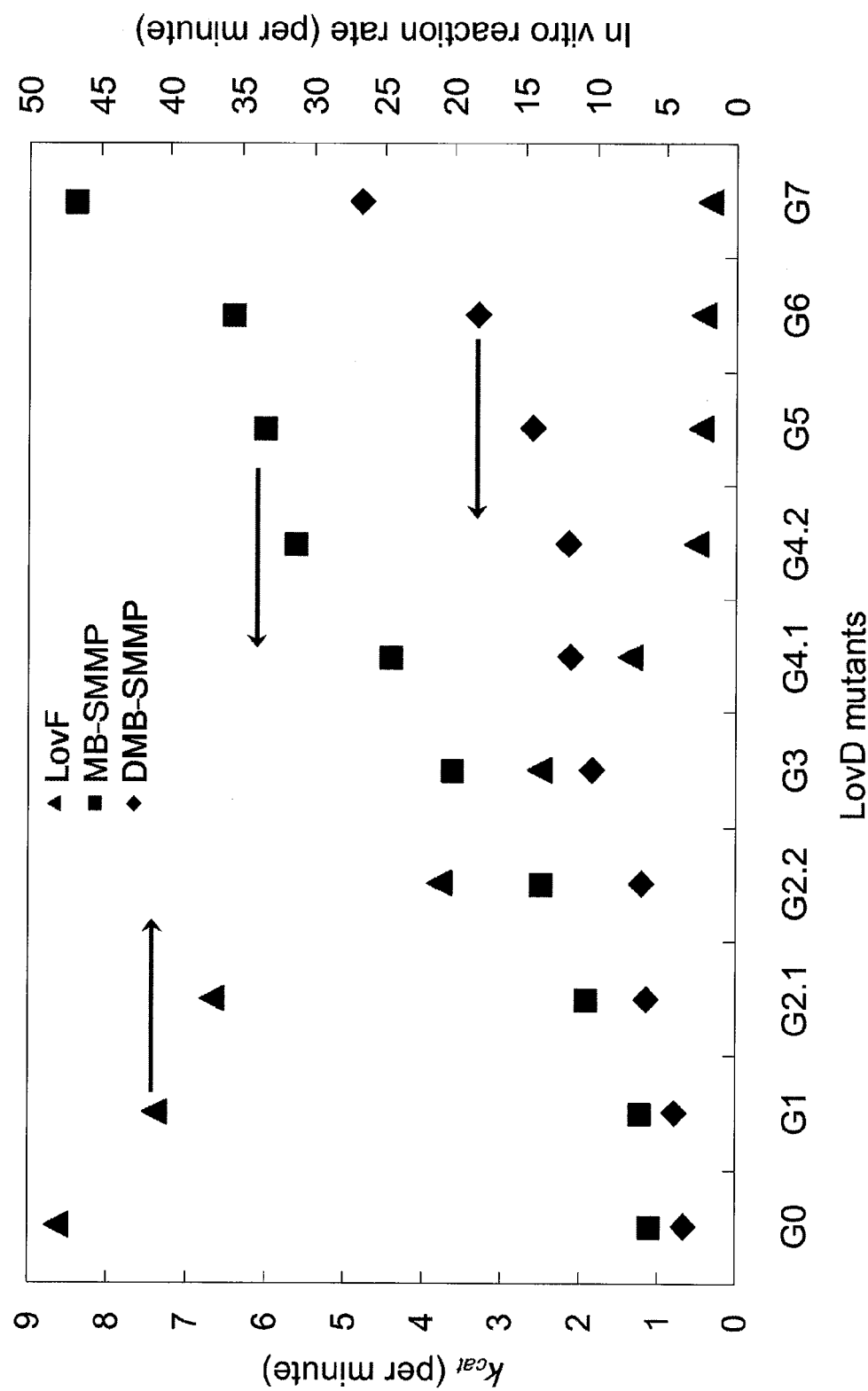
FIG. 15. Kinetic characterization of LovD mutants. Turn-over rate of LovD mutants toward SVA biosynthesis using DMB-SMNIP as substrate (, blue line, $k_{cat}$, on left y-axis), LVA biosynthesis using MB-SMMP (■, pink line, $k_{cat}$ on left y-axis) or LovF as substrate (▲, red line, apparent turnover rate on right y-axis).

To examine the activities of the mutants towards synthesis of the natural biological product LVA, we performed kinetic assays using α-methylbutyryl-SMMP (MB-SMMP) and MJA. A similar trend in the improvements of $k_{cat}$ toward LVA synthesis was observed (FIG. 15), indicating the LovD relative substrate specificity towards the acyl group (either MB or DMB) has not changed. Interestingly, when LovF was used in the kinetic assay for LVA synthesis (FIG. 7), we observed a progressive loss of activities of the LovD mutants (FIG. 15). The G7 mutant exhibited a 27-fold decrease in activities towards LovF compared to the G0 parent, most likely attributed to the deterioration of the required protein-protein interactions for catalysis (see, e.g. Xie et al., (2009) *J. Am. Chem. Soc.* 131, 8388-8389). Therefore, the mutations accumulated during directed evolution may have gradually altered the conformation of LovD to impair its communication with LovF, while not affecting binding of the SMMP-bound acyl group.

Overall Structure of LovD

Seven LovD crystal structures were determined to help illuminate the mechanism of the LovD-catalyzed reaction and possible basis for improved catalysis. These include (1) G0, (2) selenomethionyl G0 (G0-Semet), (3) the improved mutant G5, (4) G5 in complex with substrate MJA, the G5 with S76A active site mutated (called G5') in complex with (5) LVA, (6) SVA, and (7) MJA. The resolution limits of the structures range from 2.5 to 2.0 Å except for G0. The native G0 structure was resolved at 3.4 Å, but was improved to 2.5 Å in the G0-Semet variant. Refinement statistics are provided in FIG. 20.

Figure 8A:
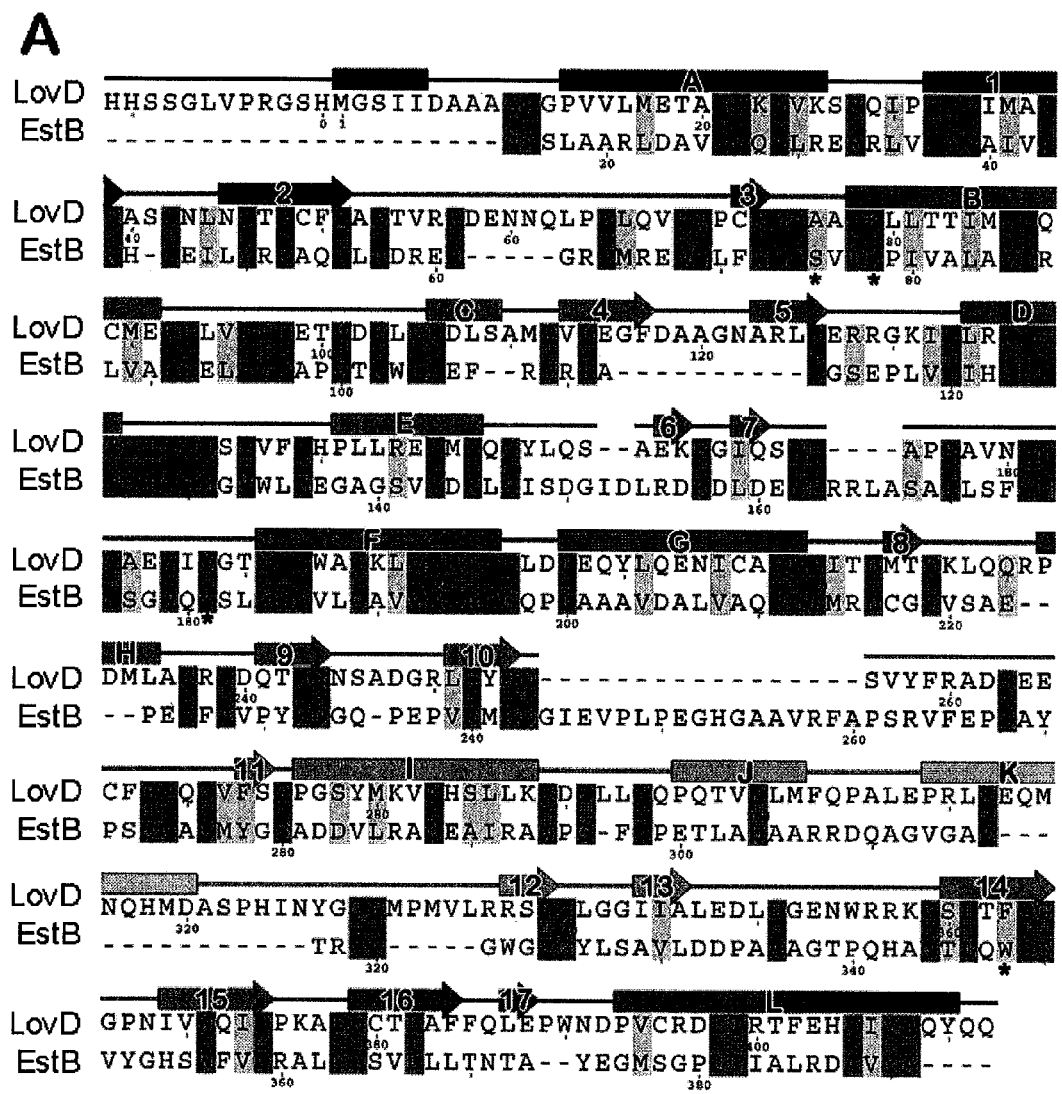
FIGS. 8A-E. The crystal structure of LovD and its relationship to EstB (SEQ ID NO: 23).
Figure 8B:
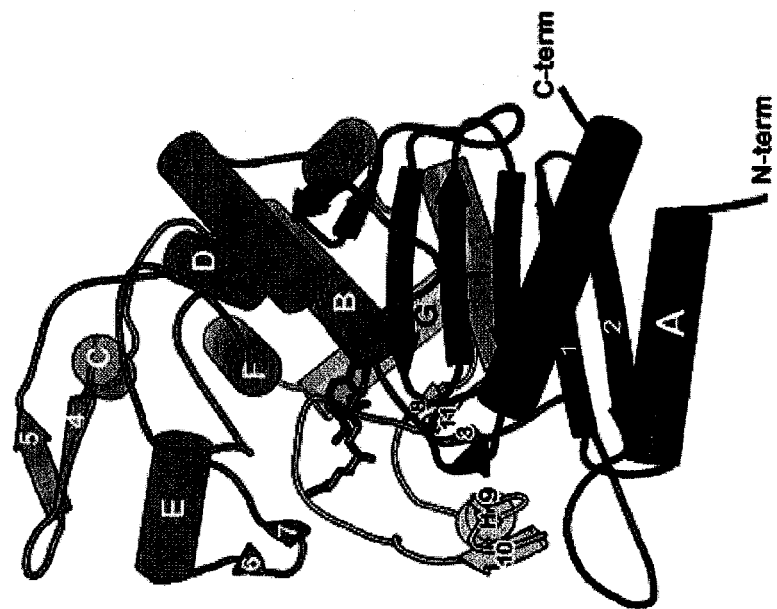
Figure 8B:
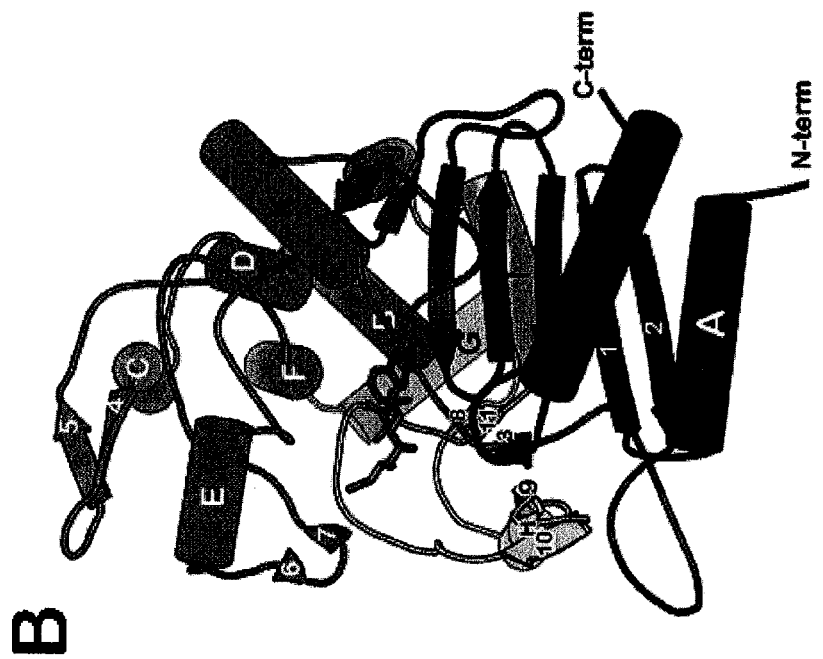
Figure 16A:
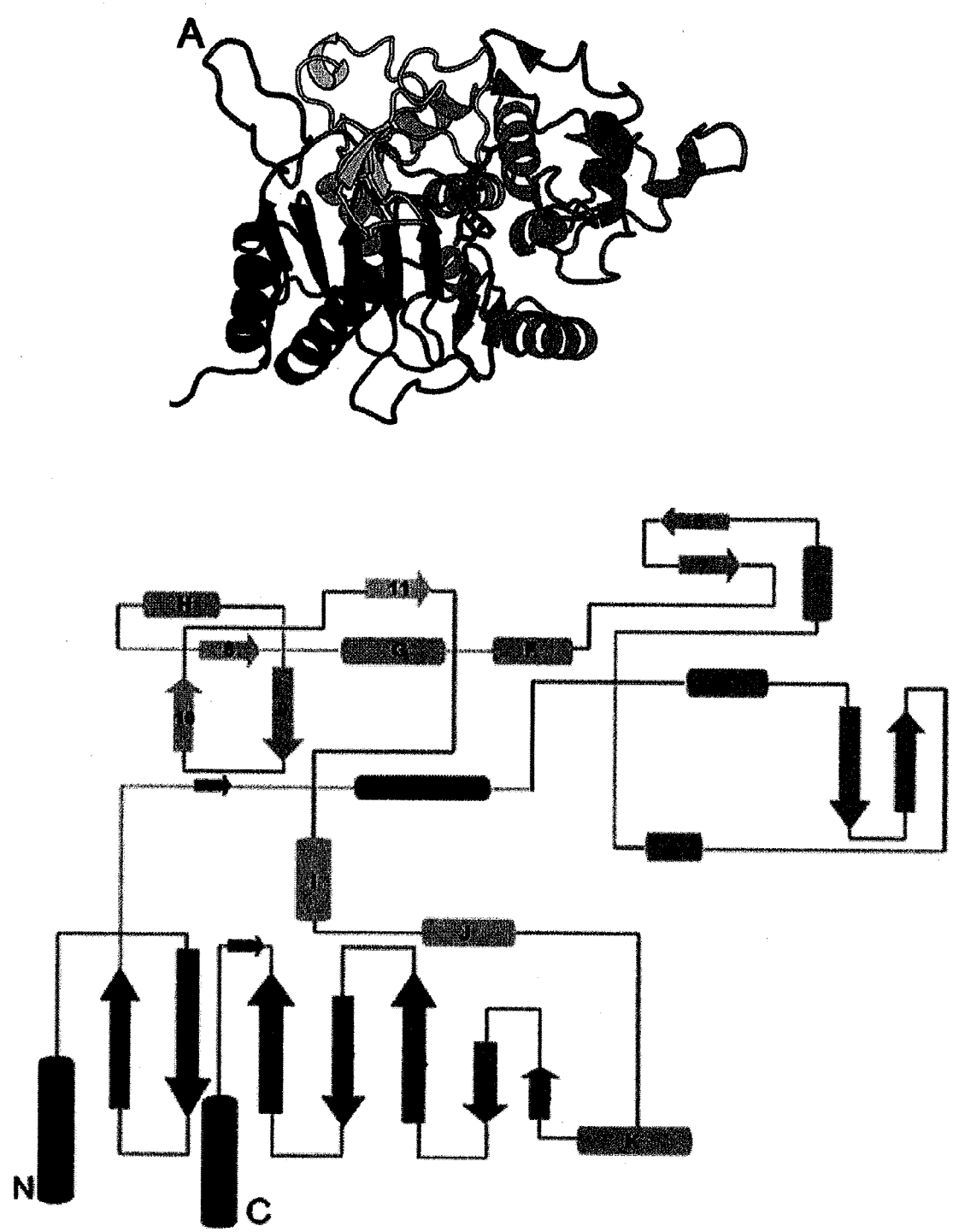
FIGS. 16A-C. LovD G5' bound to LVA and MJA.

The crystal structure of LovD G0-Semet revealed a variation of the α/β hydrolase fold (see, e.g. Heikinheimo et al., (1999) Structure 7, R141-R146 and Nardini et al., (1999) Curr. Opin. Struct. Biol. 9, 732-737). It consists of two domains. The first domain (residues 1-92 and 204-413) is a central seven-stranded antiparallel β-sheet flanked by α-helices on either face (FIGS. 8B and 16A). A cis-peptide bond is formed between Glu388 and Pro389, contributing to a kink in the sheet. The second domain is smaller (residues 93-203) and primarily α-helical. A deep and narrow cleft (11×6 Å) is formed at the interface between the two domains. At the bottom of the cleft is the catalytic Ser76 that acts as the nucleophile in the acyltransfer reaction.

Comparison Between LovD and EstB

Figure 8D:
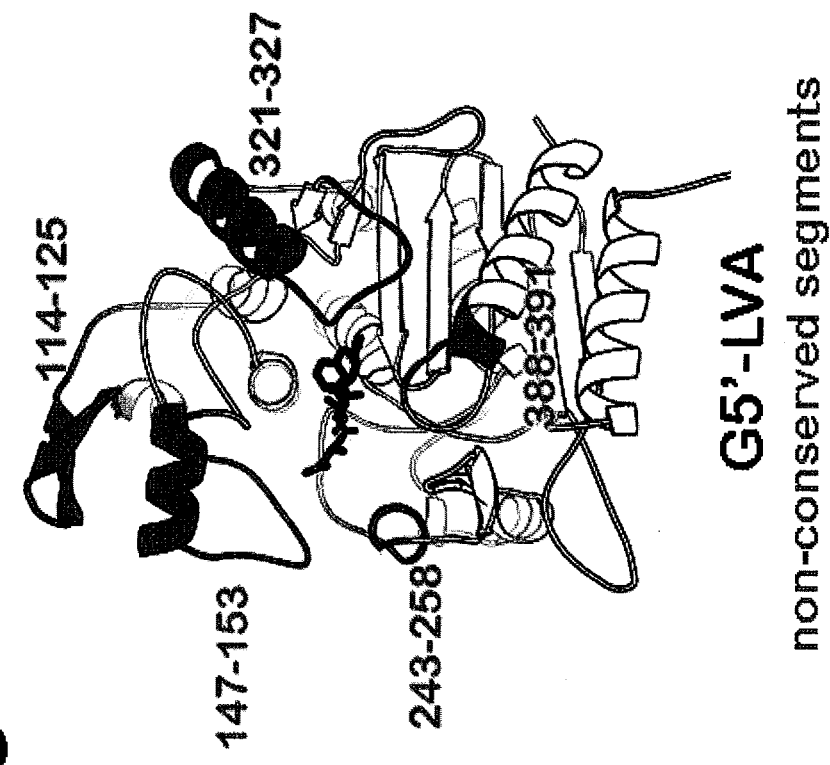
Figure 8C:
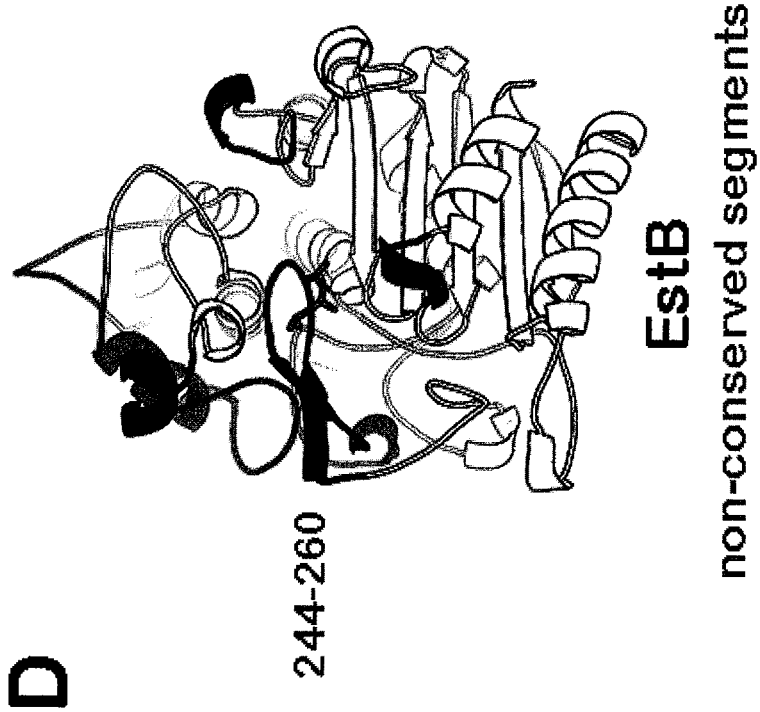
Figure 8E:
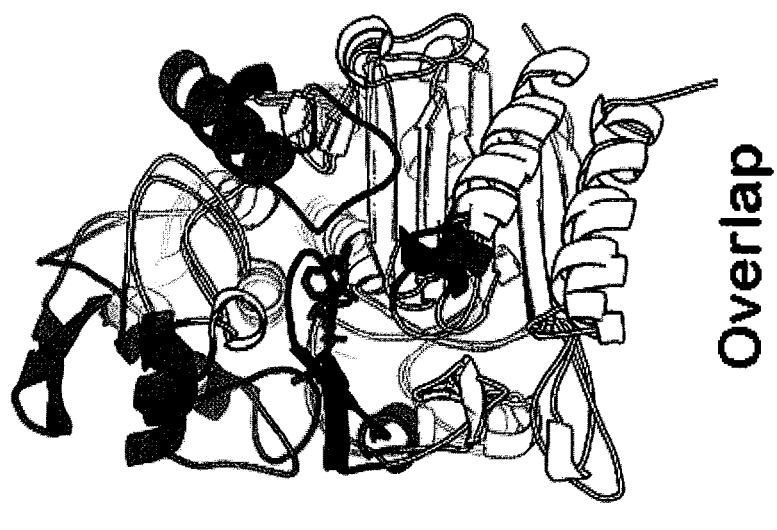
Figure 16B:
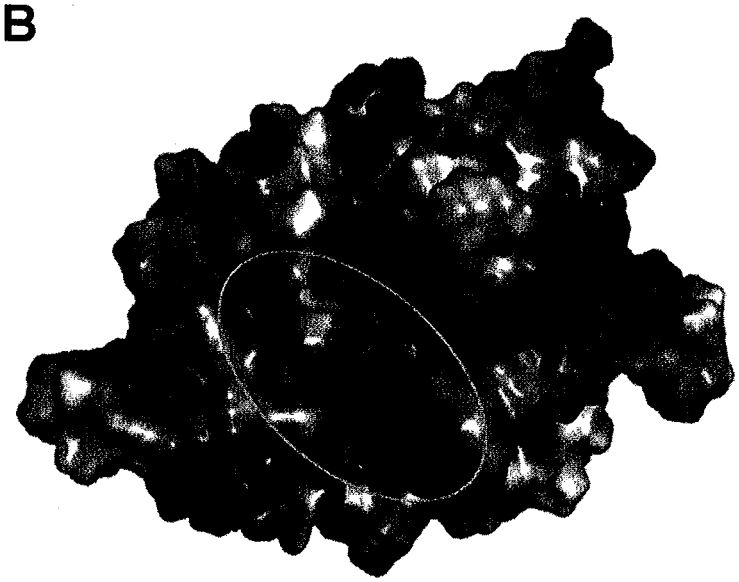

Encircling the active site cleft is a broad, ring-shaped ridge, which is absent from the homologous enzyme EstB. Their structures are superimposable with RMS deviation of only 1.5 Å over 270 pairs of α-carbons (about ⅔ of the structure) (FIG. 8E). The similarity is striking for the core of the two enzymes, but they differ notably in the loops peripheral to the active site, both in size and architecture. In LovD, these loops give the impression of a ring-shaped ridge or catcher's mitt over the active site with fingers composed of five loops: residues 114-125, 147-173, 243-258, 321-327, and 388-391 (FIG. 8C). The first and last of these loops are longer in LovD than EstB by 11 and 19 residues, respectively. The second loop is displaced 7 Å from the active site compared to EstB, extending the grasp of the "mitt". Most notably absent from the LovD molecule is the 23-residue loop that if present would obstruct the grasp of the mitt and cover the active site entrance (corresponding to residues 244-260 in EstB) (FIG. 8D). The shape and diameter of the ridge surrounding the active site (a circle of 17 Å diameter) satisfies the requirement of accommodating LovD's natural binding partner, the ACP of LovF. Moreover, a positively charged tunnel leading from the active site of LovD and the positively charged ridge surface further suggest that it binds to ACP, the surface of which tends to be negatively charged (FIG. 16B) (see, e.g. Lai et al., (2006) Biochemistry 45, 14869-14879). The distance between the rim of LovD and active site Ser76 is ~20 Å, which is roughly the same as the length of the phosphopantetheine (Ppant) arm of the ACP domain of LovF.

Crystal Structures of the Mutant G5

Figure 10:
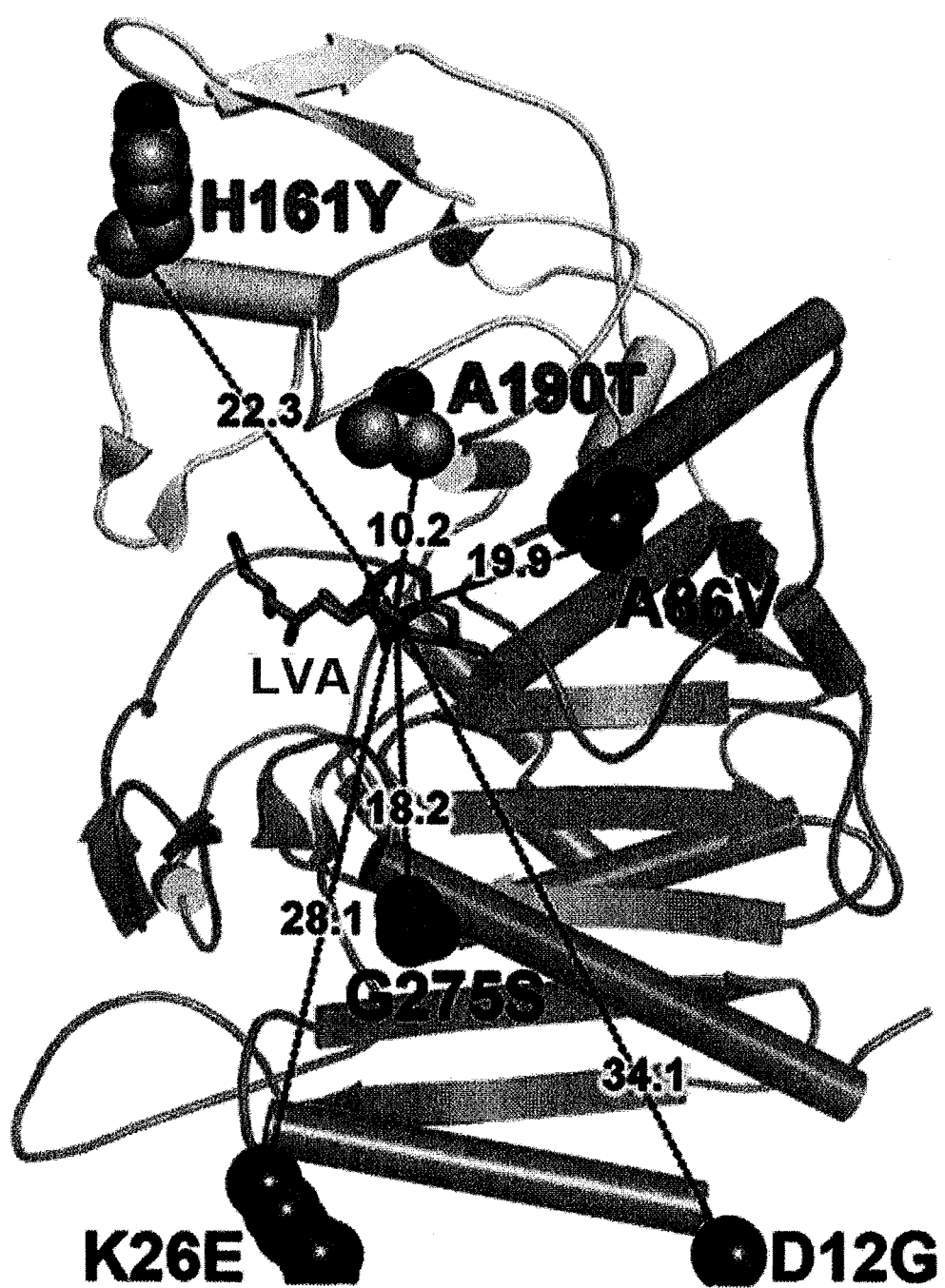
FIG. 10. Structure of the G5 mutant provides insight into improved catalysis. Positions of the amino acid changes present in the improved mutant G5, highlighting their generally large distances from the active site. Distances are drawn from the amino acid alpha carbons to the nucleophilic hydroxyl (C8) of LVA.

Knowledge of the LovD G0-Semet structure made it possible to locate in three-dimensions the residues that when mutated (in combination) were shown in this study to accelerate the catalytic activity of the LovD G5 mutant, which has a ~4 fold improvement in $k_{cat}$. These residues are scattered widely over space, forming no mutual contacts. Nor do they share a common physical environment, being located in both buried and solvent exposed regions. Moreover, distances of these residues to the active site Ser76 are relatively large, ranging from 10 to 32 Å for Thr190 and Gly12, respectively (FIG. 10). The lack of connectivity of the residues to each other and to the active site is a common phenomenon in numerous directed evolution experiments (see, e.g. Hsu et al., (2005) Proc. Nat. Acad. Sci. USA 102, 9122-9126, Oue et al., (1999) J. Biol. Chem. 274, 2344-2349, and Zhao et al., (1999) Protein Eng. 12, 47-53).

Figure 11:
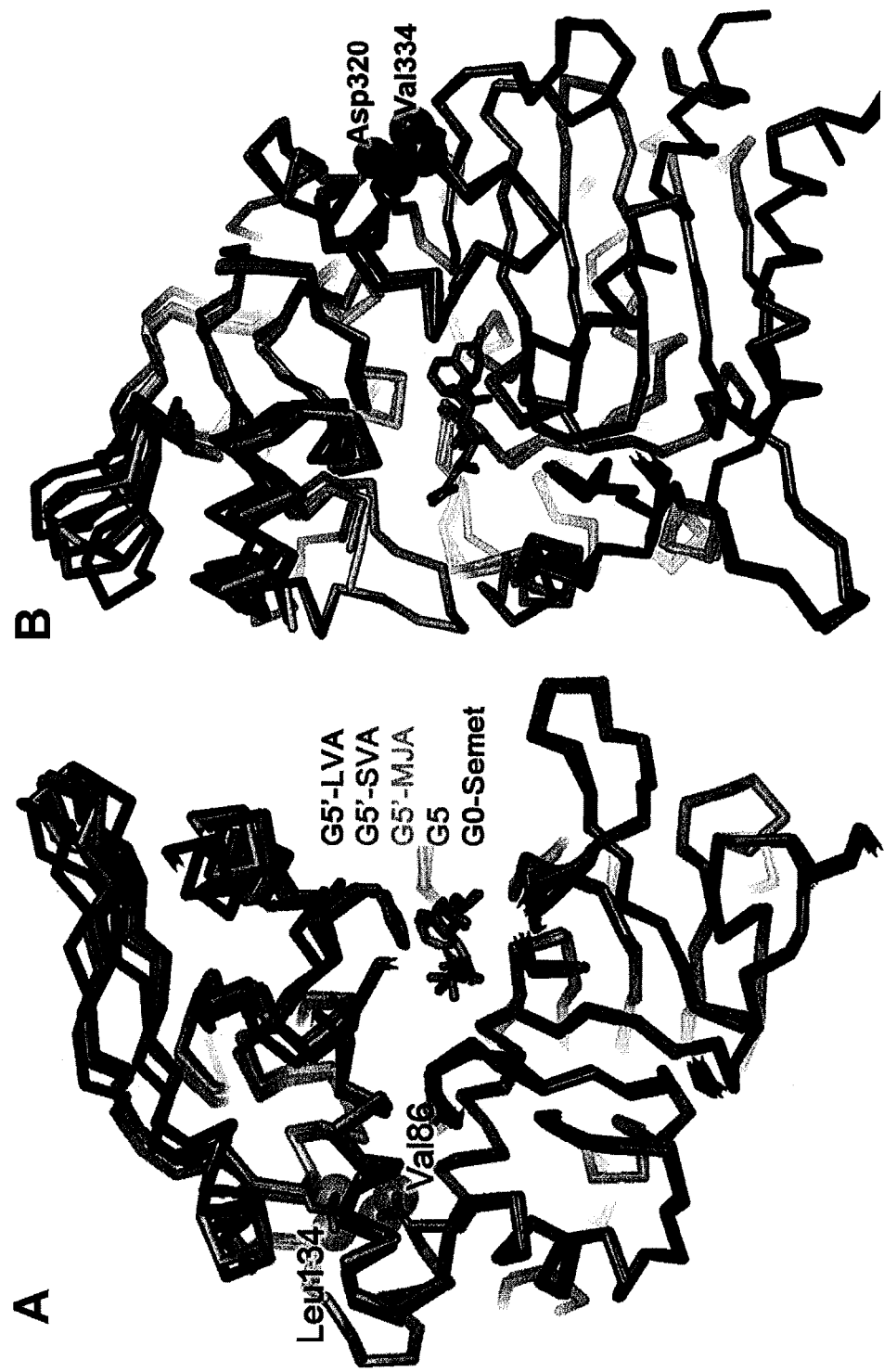
FIG. 11. Side view of the overlap of five LovD structures. This representation indicates a hinge rotation between two domains due to G5 mutations and the presence of bound ligands. (A) Two important residues (Va186 and Leu134), which may stabilize closure of the hinge, are shown in spheres. (B) Another two residues (Va1334 and Asp320) are directly in contact with each other. Mutation V334D in G6 would result in electrostatic repulsion between Asp334 and Asp320 while mutation V334F in G7 could result in steric clash between the phenyl side chain and Asp320. Both could stabilize closure of the hinge.

The crystal structure of G5, however, offered evidence to suggest that the increased activity afforded by its six mutations can be attributed to their ability to stabilize a more closed form of the active site cleft. Comparison of the G0-Semet structure with G5 revealed a rotation about the domain-domain hinge of 5°, narrowing the cleft by about 0.5 Å and producing motions up to 3 Å for atoms furthest from the hinge (FIG. 11A). Subsequent structures of G5 bound to the LVA showed larger movements along the same trajectory arising from a 14° hinge rotation. That observation suggests that the beneficial mutations in the G5 variant help promote a conformational change required for catalysis.

Figure 17:
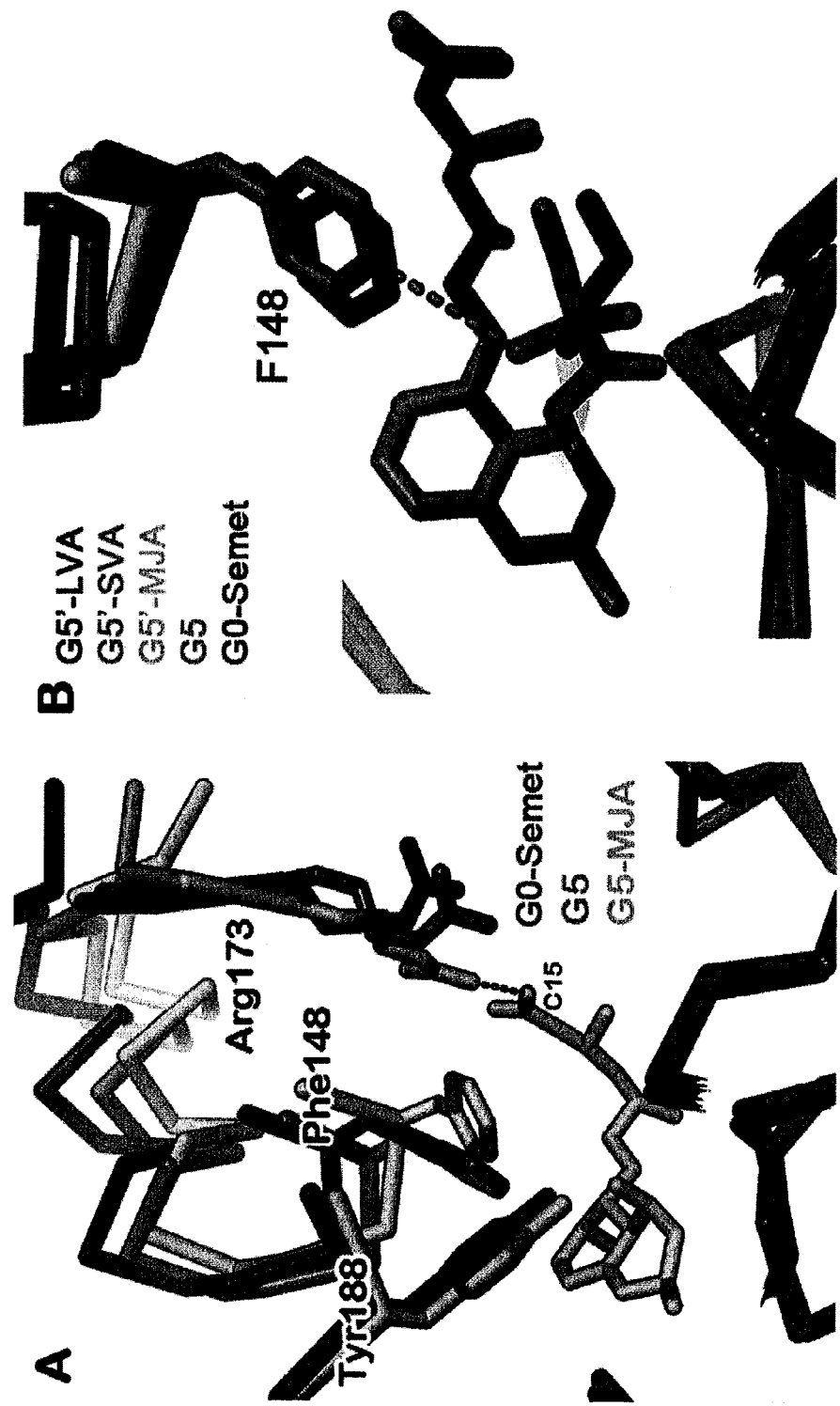
FIG. 17. Movement of key residues associated with mutations and upon binding with the ligands (A) The large domains (residues 14-92 and 204-405) of G0-Semet, G5, and G5-MJA are superimposed to indicate the movement of some key residues interacting with MJA. Domain rotation from G0-Semet to G5 closes the gap between the guanido group of Arg173 and the C15 carboxylate of MJA, which is favorable towards binding of MJA. Phe148 and Tyr188 are also closer to MJA in G5. (B) Differences between LVA and SVA binding in the LovD active site. Addition of the extra α-methyl group in SVA produces an opening of the hinge between domains via contact with Phe148.

Stabilization of the closed conformation of LovD might enhance activity by positioning residues critical for catalysis. For example, when the large domains of G0-Semet, G5, and G5-MJA are superimposed (residues 14-92 and 204-405), it is evident that domain rotation from G0-Semet to G5 closes the gap between the guanido group of Arg173 and the C15 carboxylate of MJA by 0.5 Å. This rotation could be attributed to the G5 mutations (and perhaps to a difference in crystal packing) but not to ligand binding, since the comparison is between two unliganded structures. Ligand binding produces a further rotation from G5 to G5-MJA which closes the gap between Arg173 and MJA by an additional 2.2 Å, so that a hydrogen bond is formed between the two groups. Similarly, G5 mutations bring Phe148 and Tyr188 side chains from the G0-Semet position closer to substrate (G5-MJA), although their motion is smaller since they lie closer to the hinge axis (FIG. 17A).

Figure 18A:
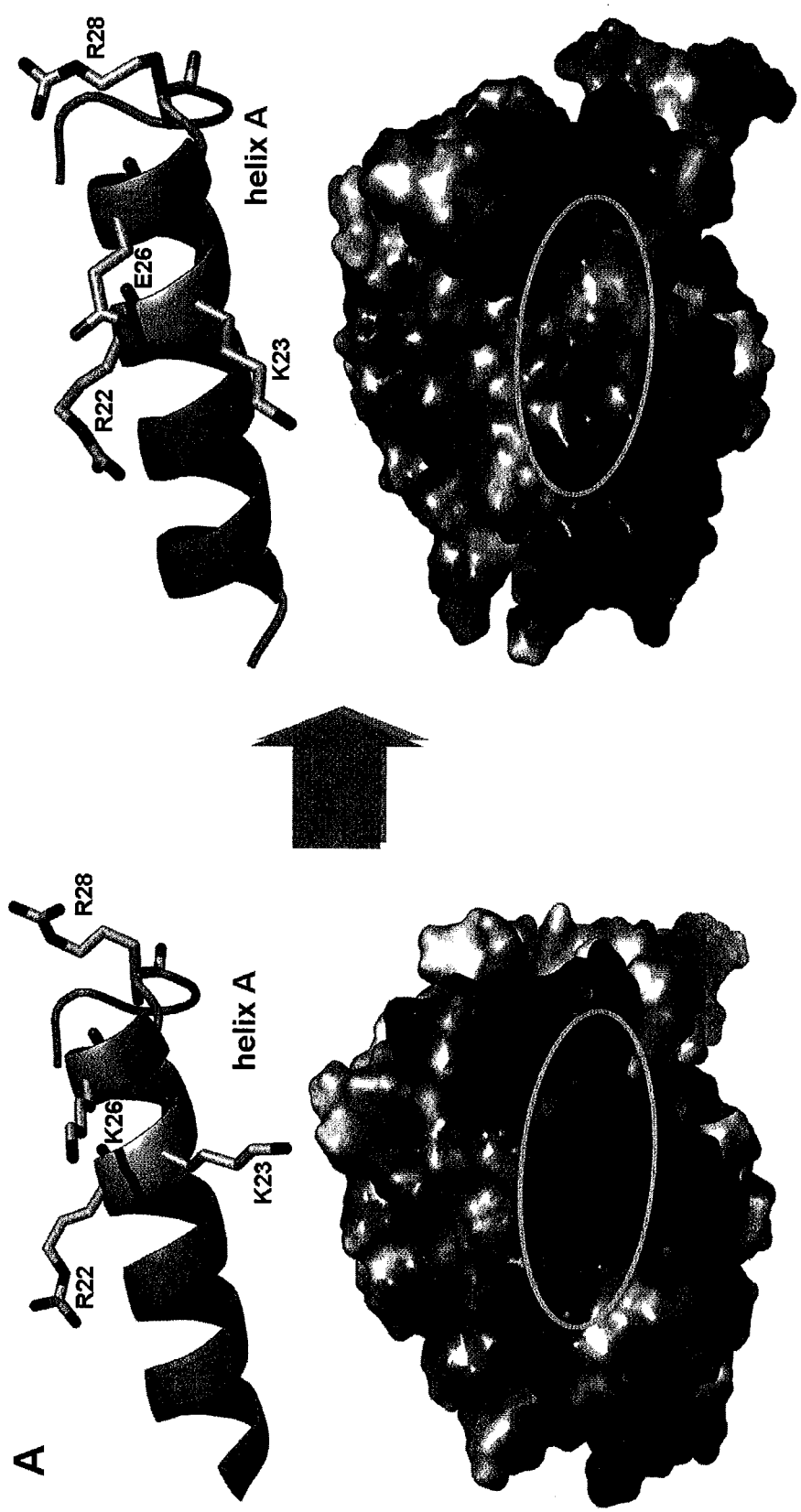
FIGS. 18A-B. Proposed mechanisms of beneficial mutations in G5.
Figure 18B:
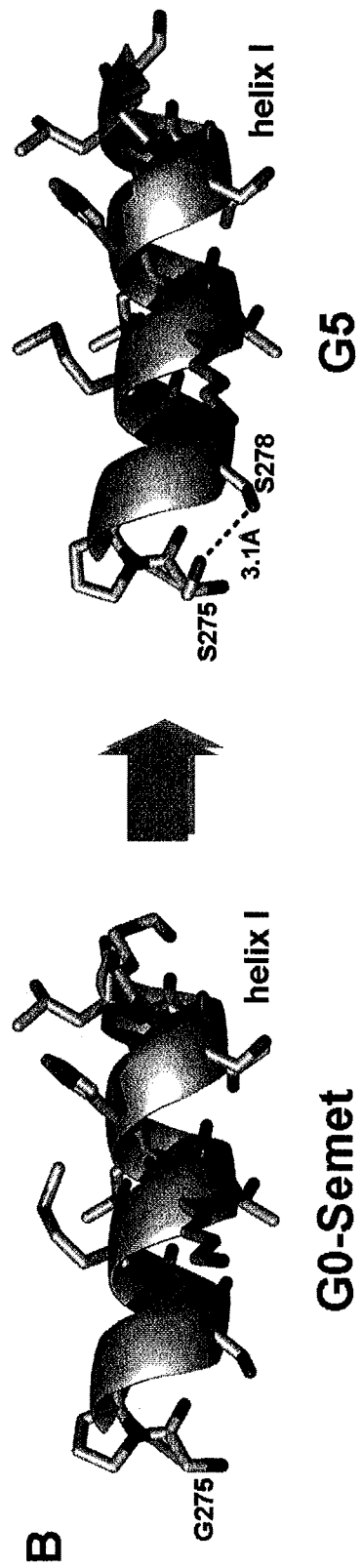

The A86V mutation in particular appears responsible for stabilizing closure of the hinge. Its two additional methyl groups buried in the boundary between domains act as a wedge pushing against Leu134 on the distal side of the hinge axis, thereby closing the active site cleft on the proximal side of the hinge axis (FIG. 11A). The beneficial effects of the K26E and G275S mutations are less obvious. The K26E mutation might improve stability of the enzyme by breaking up a patch of positively charged residues (R22, K23, K26, and R28) on the surface of helix A (FIG. 18A) (see, e.g. Schweiker et al., (2007) Protein Sci. 16, 2694-2702). The G275S mutation appears to improve stability of the enzyme by adding a hydrogen bond with the N-terminal end of helix I and decreasing torsional flexibility of the backbone (FIG. 18B).

Co-Crystallization of LovD with MJA, LVA and SVA

Figure 12:
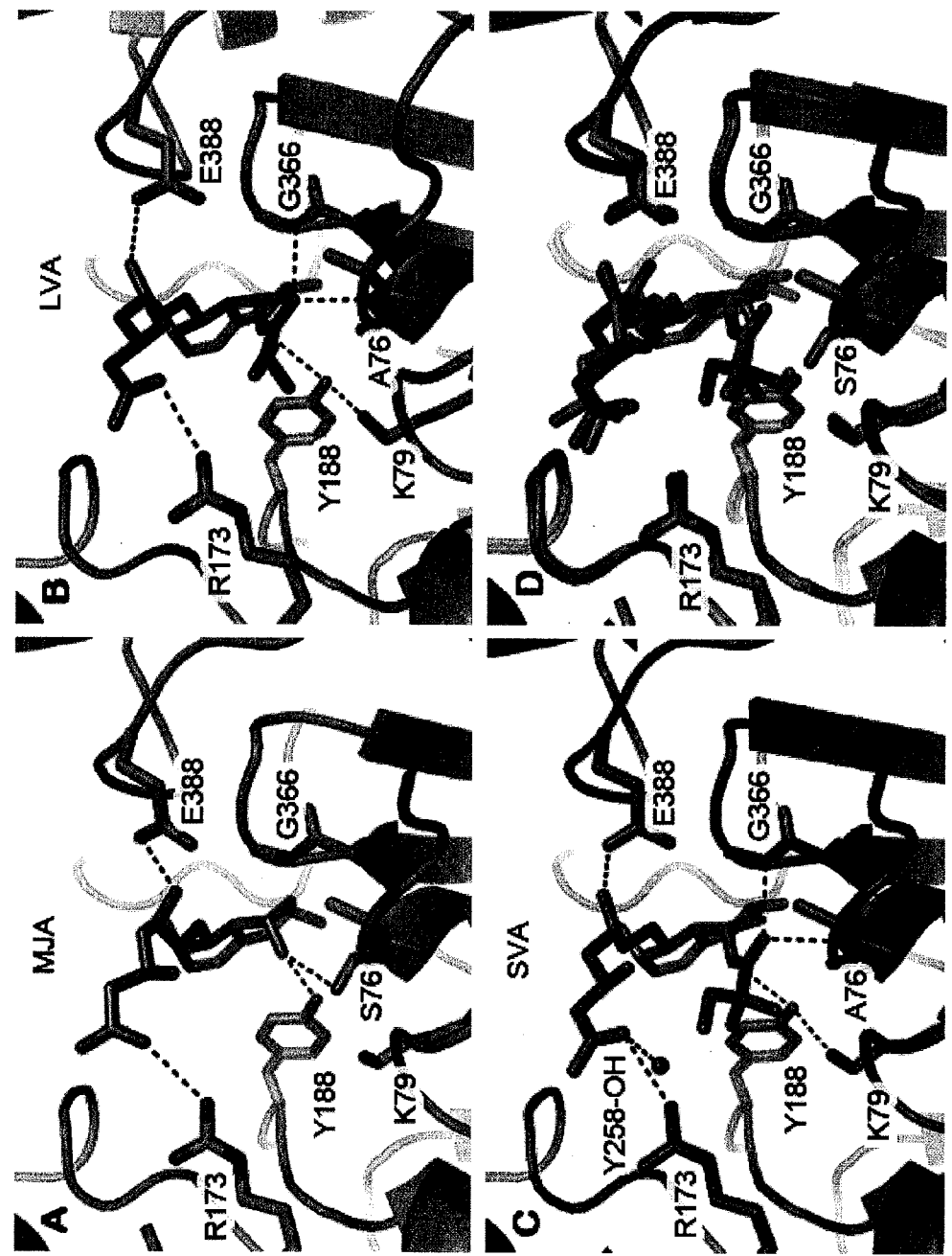
FIG. 12. Comparison of the LovD active site bound with different ligands. (A) G5 in complex with substrate MJA. (B) G5' in complex with product LVA. (C) G5' in complex with product SVA. (D) Overlay of the three structures showing conformational changes, particularly at the nucleophilic serine, associated with binding to different ligands. Dashed lines represent hydrogen bonds. The active site entrance is at the top of each figure. Some residues involved in ligand binding are not shown.
Figure 16C:
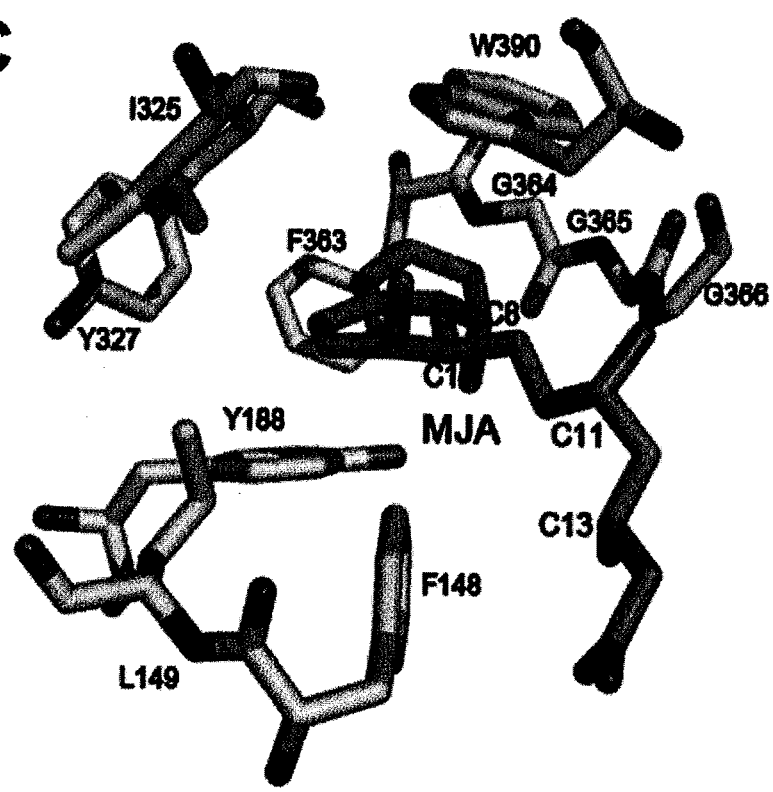
Figures 19A, 19B:
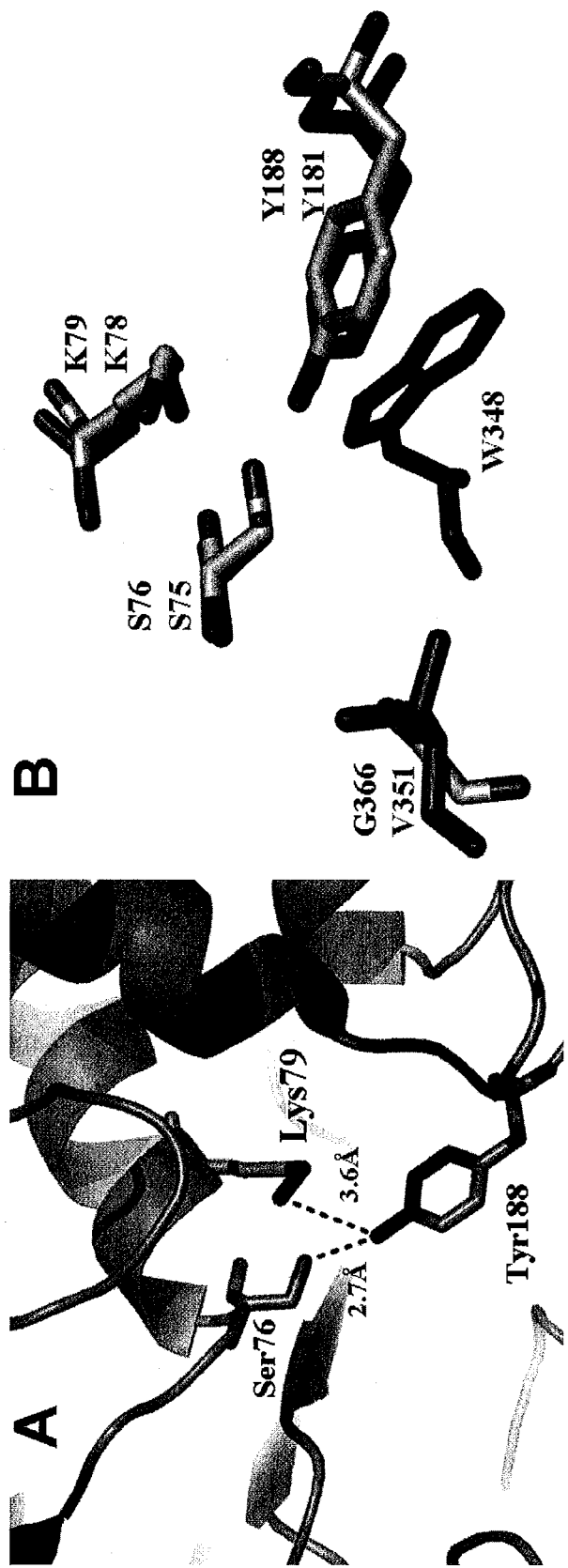
FIGS. 19A-C. Catalytic residues of LovD and proposed mechanism of LVA biosynthesis.

Structures of LovD G5' in complex with substrate and products illustrate the mode of binding of these ligands and suggest a catalytic mechanism for acyl transfer. The substrate MJA binds with its C8-hydroxyl group deep inside the cleft between domains, forming hydrogen bonds with Ser76, Tyr188, and a fortuitously bound formate molecule (used as a cryoprotectant) (FIG. 12A). The proximity of the C8-hydroxyl to the Ser76 hydroxyl is consistent with the expectation that both hydroxyl groups initiate a nucleophilic attack on the same acyl group during different steps in the reaction sequence (FIG. 19B). The two faces of the decalin ring system of MJA are sandwiched between the aromatic rings of Trp390 and Tyr188 (FIG. 16C). Additional hydrophobic and van der Waals interactions with the edges of the ring system are observed with Phe363, Ile325, Tyr327, Phe148, Ler149, and the peptide planes of Gly364, Gly365, and Gly366 (FIG. 16C). The hydrophilic tail of MJA (i.e. the C1 substituent on the decalin ring) extends away from the active site into bulk solvent. The C11 hydroxyl group hydrogen-bonds with the Glu388 side chain and the backbone amide of Trp390, the latter being mediated by a water molecule. The C15 carboxylic acid forms a salt bridge with Arg173.

The position of the α-S-methylbutyryl group is revealed in the crystal structure of the LovD G5' mutant in complex with LVA. As in the MJA complex, the decalin ring and hydrophilic tail of LVA bind with similar geometry. Interestingly, the additional methylbutyryl group extends parallel to the MJA hydrophilic tail (FIG. 12B). The proximity of the two tails gives LVA a hairpin shape, with the decalin ring forming the hairpin turn between the two tails. The hydrophobic side chain binding position is likely the site at which the acyl donor binds. The proximity of the tails also suggests how MJA competitively inhibits the acyl transfer reaction when it binds prior to the methylbutyryl substrate (see, e.g. Xie et al., (2006) Chem. Biol. 13, 1161-1169). Because the hydrophilic tail of MJA partly obstructs access of the methylbutyryl group to the active site, ordered binding of the substrates is required.

Structural comparisons between complexes of LovD G5' with LVA and SVA suggest some strain is involved in accommodating the non-natural product, SVA (FIG. 12C). SVA contains an additional methyl group compared to LVA, located on the α-S-methylbutyryl moiety. Superimposition using only α-carbons in the large domains of the two structures shows nearly identical arrangements of atoms in the large domains and the decalin rings (FIG. 12D). But contact between the additional methyl group (attached at C2') and the side chain of Phe148 appears to push open the cleft between domains. As a result, Phe148 moves approximately 0.8 Å away from its position in the LVA complex (FIG. 17B). There is also a 30° rotation about the C1'-C2' bond of the α-dimethylbutyryl moiety. The consequence of these rotations for the relative catalytic rates of the two substrates appears minor; the movements near the atoms directly involved in acyl transfer are small. This is consistent with the ability of LovD to catalyze acyl transfer using an α-dimethylbutyryl group as substrate instead of the natural α-methylbutyryl group. However, further amino acid mutations, such as the aforementioned Phe148, could improve the fit to the α-dimethylbutyryl substrate, or other variations. The structures presented here provide a framework for such design efforts.

In this Example, we show that seven amino acid changes led to the ~11 fold increase in the SV synthase activity of LovD. This level of enhancement is significant considering G0 was already an adequate SV synthase following our previous efforts in substrate and strain optimization. Although the kinetic activity of G7 is far below that of the natural reaction catalyzed by LovD using acyl-LovF, G7 is a robust mutant for high volume synthesis of SVA using the whole cell platform. Indeed, when applied in a high density fermentation environment, more than 30 g/L of MJA can be quantitatively converted to SVA within one day. The relatively few rounds of direct evolution to achieve the activities of G7 also demonstrate that LovD is highly evolvable as a biocatalyst.

Figure 19C:
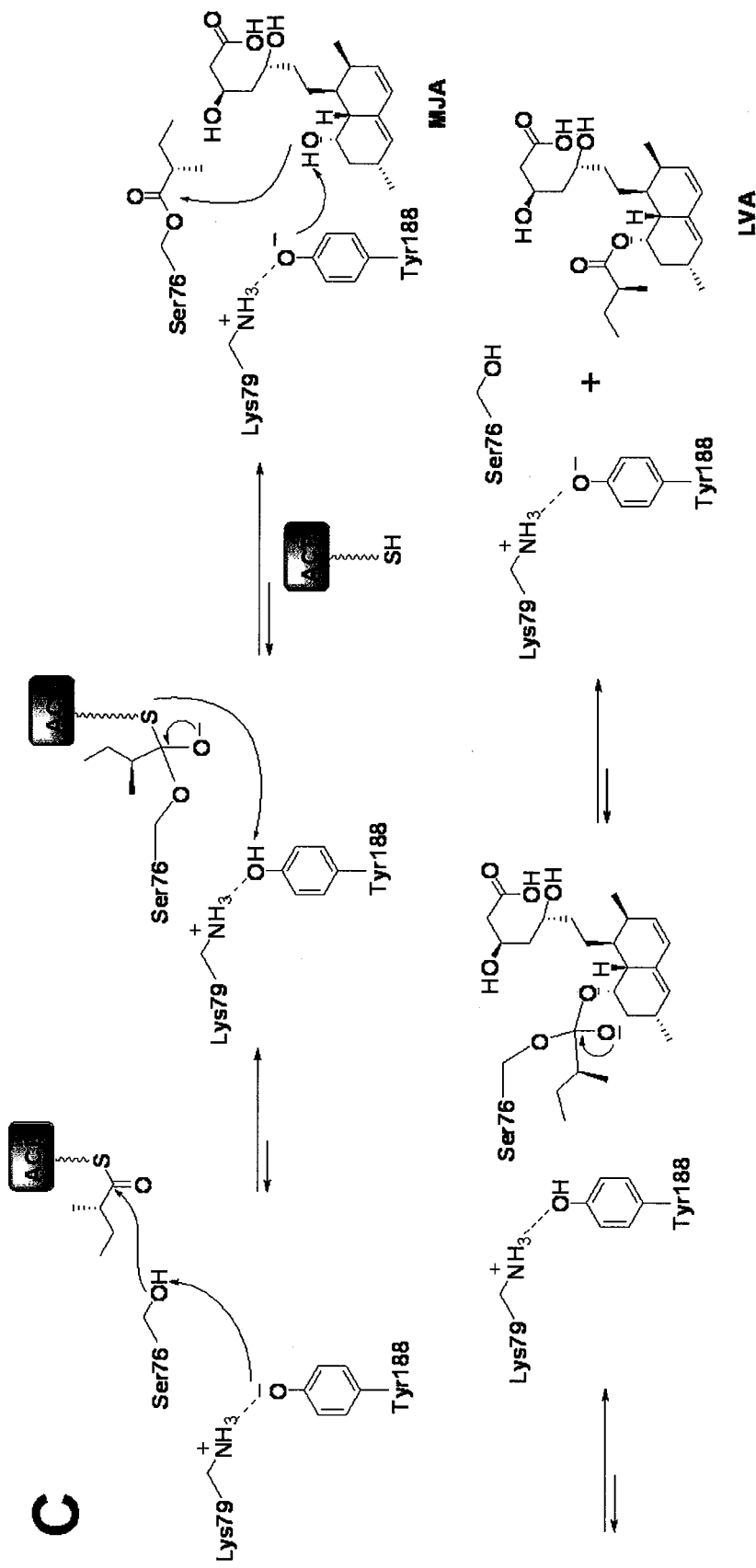

The X-ray crystal structures solved in this work provides insight into different facets of LovD enzymology. Among these, the spatial arrangement of the LovD catalytic triad Ser76-Lys79-Tyr188 was captured and is shown to be consistent with that of the esterase EstB (FIG. 19). Tyr188 (as the phenolate) appears to be the general base in initiating the two nucleophilic attacks required for completion of the acyl transfer reaction (see, e.g. Oefner et al., (1990) Nature 343, 284-288). The first nucleophilic attack is by Ser76 on the α-S-methylbutyryl group and the second attack is by the C8 hydroxyl of MJA on the acylated enzyme intermediate. In both reactions, the attacking hydroxyl group must be activated by deprotonation (FIG. 19C). Tyr188 is well-positioned to deprotonate both hydroxyl groups, forming hydrogen bonds with Ser76 in the apo-enzyme and with MJA in the G5-MJA complex. Lys79 is also well-positioned to aid in activating the two hydroxyl groups by forming a hydrogen bond relay with Tyr188 in the G5-MJA complex. Site-directed mutation of either Tyr188 or Lys79 to alanine resulted in complete loss of activity.

Details of the α-S-methylbutyryl binding pocket suggest how the transition states for the acyl transfer reactions are stabilized. As in the MJA complex, the C8 oxygen of LVA maintains a hydrogen bond to Tyr188, but the neighboring water molecule has been displaced by the carbonyl oxygen of the α-S-methylbutyryl group. This carbonyl oxygen forms a pair of hydrogen bonds with the backbone amides of Ala76 (i.e. Ser76 in the G0-Semet) and Gly366. The geometry of the hydrogen bonds appears ideal, with the amide hydrogen atoms pointed directly at the two lone electron pairs on the carbonyl oxygen. These hydrogen bonds would appear well suited to stabilize a tetrahedral transition state. The closest protein contacts with the aliphatic portion of the methylbutyryl group are aliphatic or aromatic carbons: Ala75 (Cβ), Phe148 (Cζ), Tyr146 (Cζ), and Asn270 (Cβ). Notably, the α-S-methylbutyryl aliphatic carbons are also surrounded by three positively charged side chains, Arg73, Lys79, and Arg173, all within 4.1 Å. These positive charges might help stabilize the negative charge of the oxyanion hole that forms during acyl transfer. Indeed, the pocket's affinity for negative charges is demonstrated by the fortuitous presence of a bound formate anion in this position in the G5-MJA complex.

The crystal structures provide plausible explanations for the basis of enhanced catalytic efficiency. Upon ligand binding, LovD undergoes a conformational change analogous to the closing of the catcher's mitt. Movement of the domains shown in FIG. 11A positions the catalytic residues in closer proximity to each other and to the ligands, and serves to enhance the rate of catalysis. The G5 structure suggested that beneficial mutations afforded an alternative way to pre-position the active site residues to increase the catalytic efficiency. Although the V334D and V334F mutations of G6 and G7, respectively, were discovered subsequent to the structural work of G5, the molecular explanation above can also be applied to rationalize the beneficial nature of the additional single mutations. Val334 is located in the middle of a loop between helix K and sheet 12. The two side chain methyl groups of Val334 are directly in contact with the side chain of Asp320 on helix K, which serves as one of the domain-domain hinges and is in contact with the loop where Tyr188 is located (FIG. 11B). Mutation of V334 could therefore result in movement of the domains around the helix K hinge. For example, the mutation V334D in G6 would result in electrostatic repulsion between Asp334 and Asp320. Similarly, the mutation V334F in G7 could result in steric clash between the phenyl side chain and the side chain of Asp320, further closing the active site cleft and bringing key residues (e.g. Tyr188) into more optimal positions for catalysis. On the other hand, the more compact conformations of LovD mutants are less compatible with binding to LovF, which apparently favors the open conformation of LovD.

These results disclosed herein are significant in part because Simvastatin (SV) is the active pharmaceutical ingredient of the blockbuster cholesterol-lowering drug Zocor®. Semisynthesis of SV from lovastatin (LV) is therefore an intensely pursued target for devising an efficient biocatalytic approach. Our previously developed platform for the biosynthesis of SV was powerful, but still suboptimal due to the lack of a robust biocatalyst. In this work, we employed directed evolution to engineer LovD. Several better mutants were obtained through a well designed screening method and the best mutant "G7" displaying an ~11-fold increase in SV biosynthesis compared to the parent G0. Catalytic efficiency, solubility and thermostability were improved simultaneously showing the power of our selection system. More strikingly, we have determined seven X-ray crystal structures including the parent LovD G0, an improved mutant G5, and the co-crystal structures of G5 with MJA, LVA and SVA. The structure information not only aided our understanding of the catalytic mechanism of LovD, but also afforded a great insight into how mutations affected the overall properties of LovD. Comparing the structures between LovD G0 and G5 suggests the beneficial mutations help promote a more compact conformation required for catalysis. The co-crystallization of LovD with substrate MJA, product LVA and SVA reveals how acyl transfer reaction proceeds via a ping-pong mechanism, how MJA becomes a competitive inhibitor and how the catalytic cavity is adapted to accommodate its non-natural product. Our work, therefore, can have significant impact on biocatalyst development and provides deep insights into fundamental understanding of LovD enzymology.

Experimental Procedures

Ep-PCR and Construction of Mutant Library

Ep-PCR procedure was modified from established protocols (see, e.g. Fromant et al., (1995) Anal. Biochem. 224, 347-353). The reaction consisted of 0.35 mM dATP, 0.4 mM dCTP, 0.2 mM dGTP, 1.35 mM dTTP, 4 mM $MgCl_2$, 0.25 mM $MnCl_2$, and 2.5 U Taq polymerase. The reaction mixture was submitted to 25 cycles PCR: 94° C. for 1 min, 55° C. for 1 min and 72° C. for 3 mins. The resulting PCR products were digested with DpnI, further digested with EcoRI and NdeI, and ligated to pET28(a). The ligation mixture was transformed to YT2 and plated on LB agar containing 35 mg/L kanamycin.

Selection of High Activity Mutants

N. crassa was grown on SDA slants for 10 days and spores were harvested with 1% Tween-80. 100 ml of molten SDA was seeded with 0.3-0.5×$10^8$ spores and poured into a 230×230 mm plate. Colonies from mutation library were cultured in 96 well plates containing 250 μl LB medium (with 35 mg/L kanamycin). The cells were grown at 37° C. to saturation and transferred to duplicated plates. Protein expression was induced with 0.1 mM IPTG at $OD_{600}$ of 0.5 and the expression was performed at 25° C. for 16 h. 5 mM MJA and 10 mM DMB-SMMP were added to initiate the reaction. After a certain reaction time (45 mins to 4 hours depending on the activity of the parent), cells were removed with centrifugation (2,000 g, 4° C., 5 min). The amount of supernatant spotted on the SDA plate was typically 1~3 μl. The plates were incubated at 30° C. for 16~18 hours. The improved mutants were selected following visual comparison of the inhibition zones.

Site-Directed Mutagenesis

Site-directed mutations were performed using the standard Quickchange® strategy using relevant templates. The primers were ordered from IDT (Integrated DNA Technologies). All mutations were verified by DNA sequencing (Laragen, Los Angeles, Calif.).

Saturation Mutagenesis

The LovD G6 gene was randomly mutated at positions of V334 and L361. Since the two residues are close to each other, the two random mutations were introduced in a single pair of primers. Two segments were amplified by PCR and linked together using slice-by-overlap extension (SOE) PCR to give intact LovD gene, which was subsequently introduced to pET28(a).

Determining Whole-Cell Biocatalysis Activity

Parent LovD G0 and all mutants were cultured in parallel for comparison. A single colony of the freshly transformed YT2 competent cells was used to inoculate a 5 mL LB culture supplemented with 35 mg/L kanamycin. Following overnight growth at 37° C., 100 μl of the culture was inoculated into 50 mL LB medium supplemented with 35 mg/L kanamycin. When $OD_{600}$ reached 0.4~0.6, 0.1 mM IPTG was added to the cultures and expression of all LovD variants was performed at 25° C. for 16 hr. To mimic the high density fermentation conditions, the cells were then concentrated 10-fold before addition of substrates. A 10 ml aliquot of each culture was collected by centrifugation (4° C., 2,000 g, 10 min). The cell pellet was gently resuspended in 1 ml of the medium supernatant, followed by addition of 70 μl of MJA (300 mM stock) to a final concentration of 15 mM. The concentrated culture was then divided into seven 200 μl aliquots and 1 μl of pure DMB-SMMP was added to each sample to a final concentration of 20 mM. The small cultures were then shaken at 300 rpm at 25° C. At each time point, a complete extraction of one culture aliquot was performed by adding 10 μl of 20% SDS for cells lysis, followed by extraction with 500 μl ethyl acetate containing 1% trifluoroacetic acid TFA. The organic phase was removed, evaporated, and redissolved in 500 μl acetonitrile for HPLC analysis. The whole-cell activity was determined by fitting the linear regions of the conversion time course plot.

Kinetic Assay of LovD Variants Towards MJA and DMB-SMMP

To obtain $K_M$ values for MJA and $k_{cat}$, the DMB-SMMP concentration was fixed at 2 mM, while the concentration of MJA was varied from 0.25 to 5 mM. To obtain $K_M$ values for DMB-SMMP and $k_{cat}$, the MJA concentration was fixed at 2 mM, while the concentration of DMB-SMMP was varied from 0.5 to 5 mM. Dimethyl sulfoxide (DMSO) was added to a final concentration of 10% to facilitate the solubilization of DMB-SMMP. At different time points of the kinetic assay, an aliquot of the reaction mixture was removed, quenched with 1% TFA and extracted with EA containing 1% acetic acid. The organic phase was separated, dried, resolubilized by acetonitrile (ACN) and analyzed by a Beckman Gold HPLC using a reverse phase C18 column (Alltech Apollo 5μ, 150 mm×4.6 mm) and a linear gradient: 60% ACN in water (0.1% trifluoroacetic acid (TFA)) to 95% ACN in water (0.1% TFA) for 10 min, 1 mL/min. Conversion of MJA to SVA was measured by integration of the peaks at 238 nm.

Kinetic Assay of LovD Variants Towards MB-SMMP

To compare the $k_{cat}$ of LovD mutants towards lovastatin synthesis using MB-SMMP as the substrate, both MJA and MB-SMMP were fixed at 2 mM. DMSO was added to a final concentration of 10% to facilitate the solubilization of MB-SMMP. At different time points of the kinetic assay, an aliquot of the reaction mixture was removed, quenched with 1% TFA and extracted with EA containing 1% acetic acid. The organic phase was separated, dried, resolubilized by ACN and analyzed HPLC using the same program described above.

In Vitro Assay of LovD Variants Towards LovF

50 μM LovF was incubated with 1 μM LovD variants, 2 mM MJA, 2 mM malonyl-CoA, 2 mM S-(5'-adenosyl)-L-methionine chloride (SAM), 2 mM NADPH in 100 mM PBS, pH 7.4. At 1 and 2 hours time points, an aliquot of the reaction mixture was removed, quenched with 1% TFA and extracted with EA containing 1% acetic acid. The organic phase was separated, dried, resolubilized by ACN and analyzed HPLC using the same program described above.

Comparing Expression Levels of Soluble LovD

Each expression plasmid encoding LovD mutant was transformed into *E. coli* BL21(DE3). The transformant was cultured in 50 mL LB medium containing 35 mg/L Kan at 37° C. to optical density ($OD_{600}$) value of 0.4~0.6. Protein expression was induced with 0.1 mM IPTG and the subsequent expression was performed at 25° C. for 16 h. Cells were collected by centrifugation (2,000 g, 4° C., 15 min), resuspended in 7 mL Buffer A (50 mM Tris-HCl, pH 8.0, 2 mM DTT, 2 mM EDTA), and lysed by sonication. Cell debris and insoluble proteins were removed by centrifugation (20,000 g, 4° C., 1 h). To the cleared cell lysate, 0.5 mL of Ni-NTA resin (Qiagen, Valencia, Calif.) was added to each sample. The mutants were then purified using a step gradient of Buffer A with increasing concentration of imidazole (10, 20, and 250 mM). LovD variants were eluted with 5 mL Buffer A containing 250 mM imidazole. The protein concentrations were qualitatively assessed by SDS-PAGE and quantitatively determined by the Bradford protein assay using bovine serum albumin (BSA) as the standard.

$T_M$ Measurement by Circular Dichroism

Samples were prepared by adding 50 µg of proteins to 250 µl 10 mM Tris-HCl buffer (pH 7.0). The sample was placed in a quartz cuvette with a 1 cm path length and heated in a Peltier-controlled cell at a rate of 1° C. per min. Ellipticity was monitored at 222 nm in a Jasco spectropolarimeter (Jasco Inc., Easton, Md.). The midpoint of the denaturation curve was determined with Microcal Origin 5.0 software (OriginLab Corporation, Northampton, Mass.).

Accession Numbers

The coordinates and structure factors of G0, SeMet G0, G5, G5-MJA, G5'-MJA, G5'-LVA and G5'-SVA have been deposited into the Protein Data Bank under code 3HL9, 3HLB, 3HLC, 3HLD, 3HLE, 3HLF and 3HLG, respectively.

Further Experimental Procedures and Data

Crystallization: LovD proteins were purified as previously described (see, e.g. Xie et al., (2006) Chem. Biol. 13, 1161-1169) except for selenomethionyl G0, which was purified using minimal medium (see, e.g. Doublie, S. (2007) *Methods Mol. Biol.* 363, 91-108). The proteins were dialysed overnight into 50 mM Tris pH 8.0, 150 mM NaCl and 5 mM DTT (using Spectra/Por molecular porous membrane tubing MWCO 6~8,000). LovD proteins were concentrated to a desirable concentration (using Amicon Ultra 15 MWCO 30,000).

LovD G0 (7.6 mg/ml): Crystals of G0 were grown at RT by a hanging drop vapor diffusion method using a 2:1 protein to reservoir solution ratio for a total drop size of 3 µl. Diffraction quality crystals were obtained in 3~4 days when using 20% PEG 3350, 0.1M HEPES pH 7.0, 0.25M $(NH_4)_2SO_4$, and 10 mM DTT, as a reservoir solution. In preparation for data collection crystals were briefly soaked in 30%/70% mixture of glycerol/reservoir solution and flash frozen. MJA was not observed to be present in the complex.

LovD G0 selenomethionyl (5 mg/ml): Crystals of LovD selenomethionyl G0 were grown at RT by a hanging drop vapor diffusion method using a 1:2 protein to reservoir solution ratio for a total drop size of 3 µl. Diffraction quality crystals were obtained in 5-6 days when using 22% PEG 3350, 0.1M Bis-Tris pH 6.5, 0.25M $(NH_4)_2SO_4$, and 10 mM DTT, as a reservoir solution. In preparation for data collection crystals were briefly soaked in 30%/70% mixture of glycerol/reservoir solution and flash frozen.

LovD G5 (69 mg/ml): Crystals of G5 were grown at RT by a hanging drop vapor diffusion method using a 2:1 protein to reservoir solution ratio for a total drop size of 3 µl. Diffraction quality crystals were obtained in 3~4 days when using 40% PEG 400, 0.1M HEPES pH 7.5, 0.25M $MgCl_2$, and 10 mM DTT as a reservoir solution. In preparation for data collection crystals were briefly soaked in 30%/70% mixture of glycerol/reservoir solution and flash frozen.

LovD G5+ MJA (50 mg/ml): Crystals of G5+MJA (100× molar excess of MJA) were grown at RT by a hanging drop vapor diffusion method using a 1:1 protein to reservoir solution ratio for a total drop size of 4 µl. Diffraction quality crystals were obtained in 5-6 days when using 16% PEG 3350, 0.1M magnesium formate, 0.1M Bis-Tris, pH 6.5 and 10 mM DTT, as a reservoir solution. In preparation for data collection crystals were briefly soaked in 4M lithium formate and flash frozen.

LovD G5'+MJA (66 mg/ml): Crystals of G5'+MJA (100× molar excess of MJA) were grown at RT by a hanging drop vapor diffusion method using a 1:2 protein to reservoir solution ratio for a total drop size of 3 µl. Diffraction quality crystals were obtained in 4-5 days when using 12.5% PEG 1000, 0.1M calcium acetate, 0.1M imidazole, pH 8.0 and 10 mM DTT, as a reservoir solution. In preparation for data collection crystals were briefly soaked in 30%/70% mixture of glycerol/reservoir solution and flash frozen.

LovD G5'+SVA (60 mg/ml): Crystals of G5' were grown at RT by a hanging drop vapor diffusion method using a 1:1 protein to reservoir solution ratio for a total drop size of 4 µl. Diffraction quality crystals were obtained in 3~4 days when using 20% PEG MME 550, 0.1M HEPES pH 8.0, 0.05M $MgCl_2$, and 10 mM DTT as a reservoir solution. Stock solutions of 50% Glycerol and 30% PEG MME 550 were mixed in a 70%/30% ratio, without $MgCl_2$. SVA (200 mM) was added at equal parts to the mixture above, where crystals were soaked for 10 minutes and flash frozen prior to data collection.

LovD G5'+LVA (60 mg/ml): Crystals of G5' were grown at RT by a hanging drop vapor diffusion method using a 1:1 protein to reservoir solution ratio for a total drop size of 4 µl. Diffraction quality crystals were obtained in 3~4 days when using 15% PEG MME 550, 0.1M HEPES pH 8.0, 0.05M $MgCl_2$, and 10 mM DTT, as a reservoir solution. Stock solutions of 50% Glycerol and 30% PEG MME 550 were mixed in a 70%/30% ratio, without $MgCl_2$. LVA (200 mM) was added at equal parts to the mixture above, where crystals were soaked for 10 minutes and flash frozen prior to data collection.

Data Collection

X-ray diffraction data were collected at the Advanced Photon Source (APS) beamline 24-ID-C using an ADSC Quantum 315 3×3 CCD array. Crystals were cooled to 100 K in a cryogenic nitrogen stream. Data reduction and scaling were performed using DENZO/SCALEPACK (see, e.g. Otwinowski et al., (1997) Method Enzymol. 276, 307-326). The LovD G0 data was indexed using XDS (see, e.g. Kabsch, W. (1993) J Appl. Crystallogr. 26, 795-800), as the diffraction pattern showed evidence of non-merohedral or epitaxial twinning, and XDS is superior for indexing such patterns. 5% of all reflections were selected at random from the reciprocal lattice using the CCP4 program FREERFLAG36. The same set of free R flags was maintained throughout the refinement. Care was taken to maintain the free R flags in switching between refinement programs. The data collected on G5'-MJA at the synchrotron was incomplete in the low resolution shell due to overloads on the detector. Data from an in-house source (Rigaku FR-E rotating anode generator equipped with HTC imaging plate) were used to supplement reflections that were overloaded.

Structure Determination and Refinement

The structure of LovD G0 was determined in space group P1 with molecular replacement using the program BALBES (see, e.g. Long et al., (2008) Acta Crystallogr., Sect. D: Biol. Crystallogr. 64, 125-132) and coordinates of EstB from *B. gladioli* as a search model (PDB code 1O8) (see, e.g. Wagner et al., (2002) Protein Sci. 11, 467-478). The two sequences share 32% identity over 227 residues. Four LovD molecules were found in the asymmetric unit. The first refinement steps were performed with CNS (see, e.g. Brunger et al., (1998) Acta Crystallogr. D Biol. Crystallogr. 54, 905-921), using simulated annealing and conjugate gradient algorithms and the aid of a hydrogen bond potential function (see, e.g. Fabiola et al., (2002) Protein Sci. 11, 1415-1423). Tight four-fold non-crystallographic symmetry restraints were used throughout. Later rounds of refinement were performed with REFMAC5 (see, e.g. Murshudov et al., Acta Crystallogr., Sect. D: Biol. Crystallogr. 53, 240-255) to benefit from TLS parameterization of domain disorder (see, e.g. Winn et al., (2003) Method Enzymol. 374, 300-321). After each refinement step, the model was visually inspected in Coot (see, e.g. Emsley et al., (2004) Acta Crystallogr., Sect. D: Biol. Crystallogr. 60, 2126-2132), using both 2Fo-Fc and Fo-Fc difference maps. All hydrogen atoms connected to carbon atoms and backbone nitrogen atoms were included at their geometrically calculated positions and refined using a riding model.

The structure of the selenomethionyl LovD G0 was solved in space group C2 by molecular replacement using the program PHASER (see, e.g. McCoy et al., (2007) J. Appl. Crystallogr. 40, 658-674) and coordinates of LovD G0 as a search model. Again, four LovD molecules were found in the asymmetric unit. The correctness of the molecular replacement solution was verified by the appearance of discrete peaks in the anomalous difference Fourier map over selenomethionine side chains. Both CNS and REFMAC5 were used for refinement. Tight four-fold symmetry restraints were used at first, and then reduced to medium strength at the end of the refinement.

The structure of the LovD G5 mutant was solved in space group P2$_1$2$_1$2$_1$ by molecular replacement using the program PHASER and coordinates of the selenomethionyl LovD as a search model. A single LovD G5 mutant molecule was found in the asymmetric unit. The structure was refined using REFMAC5 and COOT.

The structures of the LovD G5-MJA, G5'-MJA, S5'-SVA, and S5'-LVA were isomorphous with the uncomplexed LovD G5 mutant. Phases were obtained by the difference Fourier method, and refined as described above.

All models were validated with the following structure validation tools: PROCHECK (see, e.g. Laskowski et al., (1993) J. Appl. Crystallogr. 26, 283-291), ERRAT (see, e.g. Colovos et al., (1993) Protein Sci. 2, 1511-1519), and VERIFY3D (see, e.g. Luthy et al., (1992) Nature 356, 83-85). The coordinates of the final model and the merged structure factors have been deposited to the Protein Data Bank. The corresponding PDB codes are listed in FIG. 20.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE 1A

Acyl-thioesters as substrates of LovD[a]

| Acyl Thioester Substrate | Conversion[b], RT (min)[c] | Acyl Thioester Substrate | Conversion, RT (min) |
|---|---|---|---|
| acetyl-S-CoA | 7%, 5.1 | acetoacetyl-S-CoA | 89%, 4.6 |
| propionyl-S-CoA | 35%, 6.0 | 3-hydroxybutyryl-S-CoA | 35%, 4.2 |
| isobutyryl-S-CoA | 52%, 6.8 | crotonyl-S-CoA | 6%, 6.5 |
| butyryl-S-CoA | 87%, 6.8 | 3-hydroxy-3-methylglutaryl-S-CoA | N.R.[d] |
| hexanoyl-S-CoA | 32%, 8.7 | decanoyl-S-CoA | N.R. |

TABLE 1A-continued

Acyl-thioesters as substrates of LovD[a]

| Acyl Thioester Substrate | Conversion[b], RT (min)[c] | Acyl Thioester Substrate | Conversion, RT (min) |
|---|---|---|---|
| 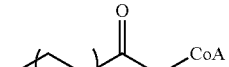 | 7%, 10.6 | 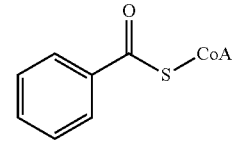 | 69%, 7.6 |
|  | 50%, 6.8 | 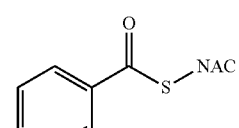 | 58%, 7.6 |
| 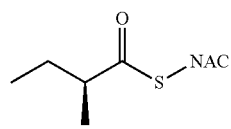 | 22%, 7.6 | 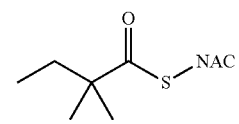 | 10%, 8.5 |
| 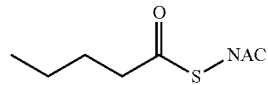 | 52%, 7.8 | 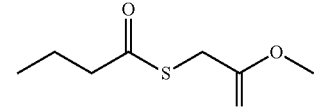 | 92%, 6.8 |
|  | 33%, 8.7 | 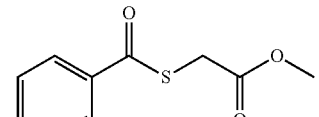 | 70%, 7.6 |
| 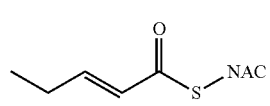 | 2%, 7.5 | 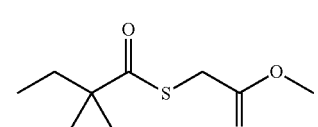 | 17%, 8.5 |

[a]The products of the reactions were verified by LC-MS. Reaction conditions: 10 μM LovD, 1 mM monacolin J, 4 mM acyl-thioester, 50 mM HEPES, pH 7.9, 25° C., 10 hours.
[b]Conversion is measured by the percent monacolin J converted to the corresponding lovastatin analog using HPLC (238 nm).
[c]HPLC (C18 reverse phase) retention time of the free acid form of product.

TABLE 1B

Comparison of initial velocities of thioester substrates.

| Thioester Substrate | Abbreviation | Initial Velocity ($k_i$, min$^{-1}$)$^a$ |
|---|---|---|
| 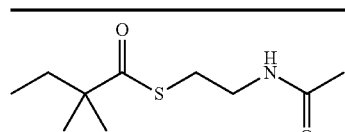 | DMB-S-NAC | 0.02 |
| 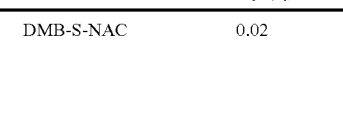 | DMB-S-MTG | 0.03 |
| 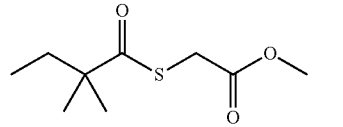 | DMB-S-MMP | 0.60 |

TABLE 1B-continued

Comparison of initial velocities of thioester substrates.

| Thioester Substrate | Abbreviation | Initial Velocity ($k_i$, min$^{-1}$)[a] |
|---|---|---|
| 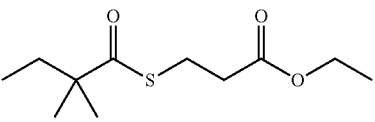 | DMB-S-EMP | 0.70 |
| 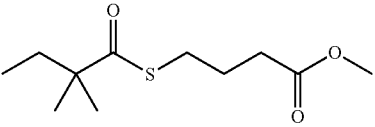 | DMB-S-MMB | 0.78 |
| 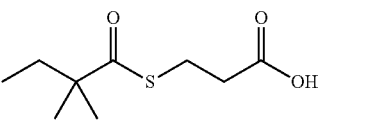 | DMB-S-MPA | 0.08 |

[a]Reaction conditions: 1 mM MJ, 4 mM thioester substrate, 10 uM pure LovD, 50 mM HEPES, pH 7.9; initial velocity is defined as the rate of initial turnover in the linear range.

TABLE 2

List of *E. coli* BW25113 mutants screened in this work. BioH was shown to be the sole enzyme responsible for DMB-S-MMP hydrolysis.

| No | Gene Deletion |
|---|---|
| 1 | ΔgloB |
| 2 | ΔmhpC |
| 3 | ΔybhA |
| 4 | ΔybiV |
| 5 | ΔycaC |
| 6 | ΔrarA |
| 7 | ΔymdC |
| 8 | ΔycfH |
| 9 | ΔycgM |
| 10 | ΔyciA |
| 11 | ΔycjT |
| 12 | ΔycjY |
| 13 | ΔynbC |
| 14 | ΔyniC |
| 15 | ΔyecD |
| 16 | ΔyegU |
| 17 | ΔlpxL |
| 18 | ΔlpxM |
| 19 | ΔyedL |
| 20 | Δddg |
| 21 | ΔcaiE |
| 22 | ΔwbbJ |
| 23 | ΔwcaF |
| 24 | ΔwcaB |
| 25 | ΔfrmB |
| 26 | ΔtesB |
| 27 | Δaes |
| 28 | ΔtesA |
| 29 | ΔybgC |
| 30 | ΔybhC |
| 31 | ΔpaaI |
| 32 | ΔyegX |
| 33 | ΔyfbT |
| 34 | ΔypfH |
| 35 | ΔypfI |
| 36 | ΔygaP |
| 37 | ΔyqaB |
| 38 | ΔyghX |
| 39 | ΔyghY |
| 40 | ΔygjP |
| 41 | ΔuxaA |
| 42 | ΔyheT |
| 43 | Δphp |
| 44 | ΔyrfG |
| 45 | ΔeptB |
| 46 | ΔyidA |
| 47 | ΔyieH |
| 48 | ΔyigB |
| 49 | ΔyigL |
| 50 | ΔysgA |
| 51 | ΔeptA |
| 52 | ΔyjfP |
| 53 | ΔcheB |
| 54 | ΔyeiG |
| 55 | ΔyqiA |
| 56 | ΔbioH |
| 57 | ΔyjjU |
| 58 | BW25113 |
| 59 | BL21(DE3) |
| 60 | BL21/pAW31 |

TABLE 3

Comparison of protein yield from different expression conditions[a]

| Fermentation Condition | LovD Concentration (mg/L)[b] |
|---|---|
| LB low density | 96 |
| F1 low density | 34 |
| TB high density | 980 |
| F1 fed-batch high density | 1500 |

[a] The reported yields represent the highest observed yield under respective conditions.
[b] The protein yield is estimated from in vitro assay using whole cell lysate as described in Materials and Methods. The conversion observed is used to estimate the LovD concentration using a turnover rate of 0.6 min$^{-1}$.

TABLE 4

Polypeptide and Polynucleotide Sequence Information

*Aspergillus terreus* LOVD transesterase. Accession AAD34555
Kennedy et al. Science. 1999 May 21; 284(5418): 1368-72

MGSIIDAAAAADPVVLMETAFRKAVKSRQIPGAVIMARDCSGNLNYTRCFGARTVRRDE
CNQLPPLQVDTPCRLASATKLLTTIMALQCMERGLVDLDETVDRLLPDLSAMPVLEGFD
DAGNARLRERRGKITLRHLLTHTSGLSYVFLHPLLREYMAQGHLQSAEKFGIQSRLAPP
AVNDPGAEWIYGANLDWAGKLVERATGLDLEQYLQENICAPLGITDMTFKLQQRPDMLA
RRADQTHRNSADGRLRYDDSVYFRADGEECFGGQGVFSGPGSYMKVLHSLLKRDGLLLQ
PQTVDLMFQPALEPRLEEQMNQHMDASPHINYGGPMPMVLRRSFGLGGIIALEDLDGEN
WRRKGSLTFGGGPNIVWQIDPKAGLCTLAFFQLEPWNDPVCRDLTRTFEHAIYAQYQQG.
(SEQ ID NO: 1)

*Penicillium citrinum* MlcH transesterase ACCESSION BAC20561
Abe et al., Mol. Genet. Genomics 267 (5), 636-646 (2002)

MAPSIDVIPTAASTAAGMISDMEAAFKSAVKLKQIPGAVVMARSMNGDIDYTRCFGART
VERDECQRLPPMEIDTPLRLASATKLLTTIMALQCMEQGLVDLDENVNRLLPDLSDMQV
LTGFDAAGNAIMRDREGIIKLRHLLTHTSGLSYAFLHPLLQEYMAKGYLKTAEKFGIQS
RLAPPAINDPGVEWIYGANLDWAGKLIERATGVDLEEFMQKNICEPLGITDMTFKLQQR
PDMLARRSDQTRRNENGSLRYDDSVYFRHDGEECFGGQGVFCGPESYMKVLNSLMKHDG
LLLKKDTIELMFQPALDAELEKKMNDHMDTTPHINYGAALPPVMRRNFGLGGIIAMGDL
DGHNWRREGSLTFGGGPNIVWQIDPTVGLCTLVVFQLEPWNDPICKDLTRKFEKAMYSQ
VKCRN.
(SEQ ID NO: 2)

*Aspergillus terreus* LOVF Polyketide Synthase AAD34559
Kennedy et al. Science. 1999 May 21; 284(5418): 1368-72

MTPLDAPGAPAPIAMVGMGCRFGGGATDPQKLWKLLEEGGSAWSKIPPSRFNVGGVYHP
NGQRVGSMHVRGGHFLDEDPALFDASFFNMSTEVASCMDPQYRLILEVVYEALEAAGIP
LEQVSGSKTGVFAGTMYHDYQGSFQRQPEALPRYFITGNAGTMLANRVSHFYDLRGPSV
SIDTACSTTLTALHLAIQSLRAGESDMAIVAGANLLLNPDVFTTMSNLGFLSSDGISYS
FDSRADGYGRGEGVAAIVLKTLPDAVRDGDPIRLIVRETAINQDGRTPAISTPSGEAQE
CLIQDCYQKAQLDPKQTSYVEAHGTGTRAGDPLELAVISAAFPGQQIQVGSVKANIGHT
EAVSGLASLIKVALAVEKGVIPPNARFLQPSKKLLKDTHIQIPLCSQSWIPTDGVRRAS
INNFGFGGANAHAIVEQYGPFAETSICPPNGYSGNYDGNLGTDQAHIYVLSAKDENSCM
RMVSRLCDYATHARPADDLQLLANIAYTLGSRRSNFRWKAVCTAHSLTGLAQNLAGEGM
RPSKSADQVRLGWVFTGQGAQWFAMGRELIEMYPVFKEALLECDGYIKEMGSTWSIIEE
LSRPETESRVDQAEFSLPLSTALQIALVRLLWSWNIQPVAVTSHSSGEAAAAYAIGALT
ARSAIGISYIRGALTARDRLASVHKGGMLAVGLSRSEVGIYIRQVPLQSEECLVVGCVN
SPSSVTVSGDLSAIAKLEELLHADRIFARRLKVTQAFHSSHMNSMTDAFRAGLTELFGA
DPSDAANASKDVIYASPRTGARLHDMNRLRDPIHWVECMLHPVEFESAFRRMCLDENDH
MPKVDRVIEIGPHGALGGPIKQIMQLPELATCDIPYLSCLSRGKSSLSTLRLLASELIR
AGFPVDLNAINFPRGCEAARVQVLSDLPPYPWNHETRYWKEPRISQSARQRKGPVHDLI
GLQEPLNLPLARSWHNVLRVSDLPWLRDHVVGSHIVFPGAGFVCMAVMGISTLCSSDHE
SDDISYILRDVNFAQALILPADGEEGIDLRLTICAPDQSLGSQDWQRFLVHSITADKND
WTEHCTGLVRAEMDQPPSSLSNQQRIDPRPWSRKTAPQELWDSLHRVGIRHGPFFRNIT
CIESDGRGSWCTFAIADTASAMPHAYESQHIVHPTTLDSAVQAAYTTLPFAGSRIKSAM
VPARVGCMKISSRLADLEARDMLRAQAKMHSQSPSALVTDVAVFDEADPVGGPVMELEG
LVFQSLGASLGTSDRDSTDPGNTCSSWHWAPDISLVNPGWLEKTLGTGIQEHEISLLE
LRRCSVHFIQEAMESLSVGDVERLSGHLAKFYAWMQKQLACAQNGELGPESSSWTRDSE
QARCSLRSVVAGSTNGEMICRLGSVLPAILRREVDPLEVMMDGHLLSRYYVDALKWSR
SNAQASELVRLCCHKNPRARILEIGGGTGGCTQLVVDSLGPNPPVGRYDFTDVSAGFFE
AARKRFAGWQNVMDFRKLDIEDDPEAQGFVCGSYDVVLACQVLHATSNMQRTLTNVRKL
LKPGGKLILVETTRDELDLFFTFGLLPGWWLSEEPERQSTPSLSPTMWRSMLHTTGFNG
VEVEARDCDSHEFYMISTMMSTAVQATPMSCSVKLPEVLLVYVDSSTPMSWISDLQGEI
RGRNCSVTSLQALRQVPPTEGQICVFLGEVEHSMLGSVTNDDFTLLTSMLQLAGGTLWV
TQGATMKSDDPLKALHLGLLRTMRNESHGKRPVSLDLDPSRNPWTGDSRDAIVSVLDLI
SMSDEKEFDYAERDGVIHVPRAFSDSINGGEEDGYALEPFQDSQHLLRLDIQTPGLLDS
LHFTKRNVDTYEPDKLPDDWVEIEPRAFGLNFRDIMVAMGQLESNVMGFECAGVVTSLS
ETARTIAPGLAVGDRVCALMNGHWASRVTTSRTNVVRIPETLSFPHAASIPLAFTTAYI

TABLE 4-continued

Polypeptide and Polynucleotide Sequence Information

SLYTVARILPGETVLIHAGAGGVGQAAIILAQLTGAEVFTTAGSETKRNLLIDKFHLDP
DHVFSSRDSSFVDGIKTRTRGKGVDVVLNSLAGPLLQKSFDCLARFGRFVEIGKKDLEQ
NSRLDMSTFVRNVSFSSVDILYWQQAKPAEIFQAMSEVILLWERTAIGLIHPISEYPMS
ALEKAFRTMQSGQHVGKIVVTVAPDDAVLVRQERMPLFLKPNVSYLVAGGLGGIGRRIC
EWLVDRGARYLIILSRTARVDPVVTSLQERGCTVSVQACDVADESQLEAALQQCRAEEM
PPIRGVIQGAMVLKDALVSQMTADGFHAALRPKVQGSWNLHRIASDVDFFVMLSSLVGV
MGGAGQANYAAAGAFQDALAEHRMAHNQPAVTIDLGMVQSIGYVAETDSAVAERLQRIG
YQPLHEEEVLDVLEQAISPVCSPAAPTRPAVIVTGINTRPGPHWAHADWMQEARFAGIK
YRDPLRDNHGALSLTPAEDDNLHARLNRAISQQESIAVIMEAMSCKLISMFGLTDSEMS
ATQTLAGIGVDSLVAIELRNWITAKFNVDISVFELMEGRTIAKVAEVVLQRYKA.
(SEQ ID NO: 3)

*Escherichia coli* Carboxylesterase bioH ACCESSION Q8FCT4
Welsch et al., Proc. Nati. Acad. Sci. U.S.A. 99 (26),
17020-17024 (2002)

MNNIWWQTKGQGNVHLVLLHGWGLNAEVWRCIDEELSSHFTLHLVDLPGFGRSRGFGAL
SLADMAEAVLQQAPDKAIWLGWSLGGLVASQIALTHPERVQALVTVASSPCFSARDEWP
GIKPDVLAGFQQQLSDDFQRTVERFLALQTMGTETARQDARALKKTVLALPMPEVDVLN
GGLEILKTVDLRQPLQNVSMPFLRLYGYLDGLVPRKVVPMLDKLWPHSESYIFAKAAHA
PFISHPAEFCHLLVALKQRV.
(SEQ ID NO: 4)

Polynucleotide encoding *Aspergillus terreus* LOVD
transesterase. EMBLCDS: AAD34555 Kennedy et al.
Science. 1999 May 21; 284(5418): 1368-72

ATGGGATCCATCATTGATGCTGCTGCGGCAGCGGATCCGGTTGTTCTGATGGAAACCGC
CTTCCGCAAGGCCGTGAAATCCAGGCAGATCCCCGGGGCGGTCATCATGGCCCGAGATT
GCAGTGGCAATCTAAATTATACGCGCTGCTTCGGGGCTCGGACGGTGCGACGGGACGAG
TGCAATCAGCTGCCGCCGCTACAGGTCGACACCCCCTGCCGGCTCGCCAGTGCGACCAA
GCTGCTGACCACGATCATGGCCCTACAATGCATGGAGCGCGGTCTCGTGGACTTGGATG
AGACGGTGGATAGGCTGCTTCCGGATTTGAGCGCGATGCCCGTGCTGGAGGGGTTTGAC
GACGCGGGAAACGCAAGATTGCGAGAGCGTCGGGGGAAGATCACGCTGCGGCACCTGCT
GACGCATACATCGGGACTGTCGTACGTCTTCCTCCATCCGTTGCTCCGGGAATACATGG
CCCAGGGCCACCTCCAGTCGGCAGAAAAGTTTGGCATCCAGAGTCGCCTGGCGCCGCCG
GCCGTCAACGACCCTGGGGCGGAGTGGATCTACGGCGCCAACCTGGACTGGGCGGGTAA
GCTCGTCGAGCGGGCCACCGGCCTCGACCTGGAGCAGTACCTGCAGGAGAATATCTGTG
CGCCGCTGGGCATCACCGACATGACCTTTAAGCTGCAGCAACGGCCGGATATGCTTGCG
CGCCGGGCCGACCAAACGCACCGCAACTCGGCGGATGGGCGCCTGCGCTACGACGACTC
GGTCTACTTCCGGGCCGATGGAGAGGAGTGCTTCGGCGGCCAGGGGGTGTTCTCGGGCC
CTGGGTCCTATATGAAGGTGCTTCACTCGCTGTTGAAGCGAGACGGGCTCCTGCTGCAG
CCACAGACCGTGGACTTGATGTTTCAGCCTGCCCTCGAGCCGCGACTCGAAGAGCAGAT
GAACCAGCACATGGACGCCAGCCCACATATCAACTACGGTGGGCCGATGCCCATGGTCC
TTCGTCGCAGCTTTGGGCTGGGGGGGATCATCGCCTTGGAGGATCTGGACGGAGAGAAC
TGGCGCCGAAAAGGTTCCTTGACCTTTGGGGGTGGCCCAAACATTGTGTGGCAAATCGA
CCCCAAAGCCGGCCTGTGCACCCTTGCGTTCTTCCAACTGGAACCCTGGAATGACCCGG
TCTGTCGTGATCTGACACGCACATTCGAGCATGCCATCTATGCGCAGTACCAGCAGGGT
TAA
(SEQ ID NO: 5)

The invention claimed is:

1. An isolated variant of a native LovD polypeptide, wherein the variant LovD polypeptide comprises at least two amino acid substitutions at an amino acid residue selected from the group consisting of: A10; D12; K26; A86; A190; H161; K227; G275; V334; and L361 of SEQ ID NO: 1, wherein the variant LovD polypeptide has an improved thermal stability as compared to the LovD polypeptide of SEQ ID NO:1.

2. The variant LovD polypeptide of claim 1, wherein the variant LovD polypeptide further comprises amino substitutions at amino acid residue positions C40 and C60 of SEQ ID NO:1.

3. The variant LovD polypeptide of claim 1, wherein the variant LovD polypeptide comprises amino acid substitutions selected from the group consisting of: A10V; D12G; K26E; C40A; C60N; A86V; H161Y; A190T; K227R; G275S; V334D; V334F; and L361M of SEQ ID NO:1.

4. The variant LovD polypeptide of claim 1, wherein the at least two amino acid substitutions of the variant LovD polypeptide include at least one amino acid residue position selected from the group consisting of: K26, G275, and L361 of SEQ ID NO:1.

5. The variant LovD polypeptide of claim 1, wherein the at least two amino acid substitutions of the variant LovD polypeptide include at least one amino acid residue selected from the group consisting of: K26E, G275S, and L361M of SEQ ID NO:1.

6. The variant LovD polypeptide of claim 2, wherein the variant exhibits:
   a decreased aggregation;
   an improved catalytic activity;
   an improved $k_{cat}/K_m$ value;
   an improved soluble expression level; or
   an improved whole cell activity at 25° C.;
as compared to the LovD polypeptide shown in SEQ ID NO:1.

7. The variant LovD polypeptide of claim 1, wherein the variant LovD polypeptide comprises amino acid substitutions at:

amino acid residue position A190;
amino acid residue positions D12, and G275;
amino acid residue positions D12, A190, and G275;
amino acid residue positions D12, K26, H161, A190, and G275;
amino acid residue positions A10, D12, K26, A190, and G275;
amino acid residue positions D12, K26, H161, A190, and G275;
amino acid residue positions D12, K26, H161, A190, G275, V334, and L361; or
amino acid residue positions D12, K26, H161, A190, G275, and V334 of SEQ ID NO:1.

8. The variant LovD polypeptide of claim 1, wherein the variant LovD polypeptide comprises amino acid substitutions at:
D12G, C40A, C60N, A86V, A190T, and G275S;
D12G, K26E, C40A, C60N, A86V, H161Y, A190T, and G275S; or
D12G, K26E, C40A, C60N, A86V, H161Y, A190T, G275S, and V334F of SEQ ID NO:1.

9. A chimeric molecule comprising the variant LovD polypeptide of claim 1, fused to a heterologous amino acid sequence.

10. An isolated variant of a native LovD polypeptide, wherein:
the variant LovD polypeptide comprises amino acid substitutions at an amino acid residue selected from the group consisting of: A10; D12; K26; A86; A190; H161; K227; G275; V334; and L361 of SEQ ID NO: 1, wherein the variant LovD polypeptide has an improved thermal stability as compared to the LovD polypeptide of SEQ ID NO:1; and
the variant LovD polypeptide is fused to a heterologous amino acid sequence.

* * * * *

SEQUENCE LISTING

<160> NUMBER OF SEQ ID NOS: 24

<210> SEQ ID NO 1
<211> LENGTH: 413
<212> TYPE: PRT
<213> ORGANISM: Aspergillus terreus

<400> SEQUENCE: 1

Met Gly Ser Ile Ile Asp Ala Ala Ala Ala Asp Pro Val Val Leu
1               5                   10                  15

Met Glu Thr Ala Phe Arg Lys Ala Val Lys Ser Arg Gln Ile Pro Gly
            20                  25                  30

Ala Val Ile Met Ala Arg Asp Cys Ser Gly Asn Leu Asn Tyr Thr Arg
        35                  40                  45

Cys Phe Gly Ala Arg Thr Val Arg Asp Glu Cys Asn Gln Leu Pro
    50                  55                  60

```
Pro Leu Gln Val Asp Thr Pro Cys Arg Leu Ala Ser Ala Thr Lys Leu
 65                  70                  75                  80

Leu Thr Thr Ile Met Ala Leu Gln Cys Met Glu Arg Gly Leu Val Asp
                 85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Ala Arg Leu Arg Glu Arg
        115                 120                 125

Arg Gly Lys Ile Thr Leu Arg His Leu Leu Thr His Thr Ser Gly Leu
130                 135                 140

Ser Tyr Val Phe Leu His Pro Leu Leu Arg Glu Tyr Met Ala Gln Gly
145                 150                 155                 160

His Leu Gln Ser Ala Glu Lys Phe Gly Ile Gln Ser Arg Leu Ala Pro
                165                 170                 175

Pro Ala Val Asn Asp Pro Gly Ala Glu Trp Ile Tyr Gly Ala Asn Leu
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
210                 215                 220

Thr Phe Lys Leu Gln Gln Arg Pro Asp Met Leu Ala Arg Arg Ala Asp
225                 230                 235                 240

Gln Thr His Arg Asn Ser Ala Asp Gly Arg Leu Arg Tyr Asp Asp Ser
                245                 250                 255

Val Tyr Phe Arg Ala Asp Gly Glu Glu Cys Phe Gly Gln Gly Val
            260                 265                 270

Phe Ser Gly Pro Gly Ser Tyr Met Lys Val Leu His Ser Leu Leu Lys
        275                 280                 285

Arg Asp Gly Leu Leu Leu Gln Pro Gln Thr Val Asp Leu Met Phe Gln
290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Leu Thr Phe Gly Gly Pro Asn
        355                 360                 365

Ile Val Trp Gln Ile Asp Pro Lys Ala Gly Leu Cys Thr Leu Ala Phe
370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
                405                 410
```

<210> SEQ ID NO 2
<211> LENGTH: 418
<212> TYPE: PRT
<213> ORGANISM: Penicillium citrinum

<400> SEQUENCE: 2

```
Met Ala Pro Ser Ile Asp Val Ile Pro Thr Ala Ala Ser Thr Ala Ala
 1               5                  10                  15

Gly Met Ile Ser Asp Met Glu Ala Ala Phe Lys Ser Ala Val Lys Leu
```

```
                  20                  25                  30
Lys Gln Ile Pro Gly Ala Val Val Met Ala Arg Ser Met Asn Gly Asp
                35                  40                  45
Ile Asp Tyr Thr Arg Cys Phe Gly Ala Arg Thr Val Glu Arg Asp Glu
 50                  55                  60
Cys Gln Arg Leu Pro Pro Met Glu Ile Asp Thr Pro Leu Arg Leu Ala
 65                  70                  75                  80
Ser Ala Thr Lys Leu Leu Thr Thr Ile Met Ala Leu Gln Cys Met Glu
                85                  90                  95
Gln Gly Leu Val Asp Leu Asp Glu Asn Val Asn Arg Leu Leu Pro Asp
                100                 105                 110
Leu Ser Asp Met Gln Val Leu Thr Gly Phe Asp Ala Ala Gly Asn Ala
                115                 120                 125
Ile Met Arg Asp Arg Glu Gly Ile Ile Lys Leu Arg His Leu Leu Thr
                130                 135                 140
His Thr Ser Gly Leu Ser Tyr Ala Phe Leu His Pro Leu Leu Gln Glu
145                 150                 155                 160
Tyr Met Ala Lys Gly Tyr Leu Lys Thr Ala Glu Lys Phe Gly Ile Gln
                165                 170                 175
Ser Arg Leu Ala Pro Pro Ala Ile Asn Asp Pro Gly Val Glu Trp Ile
                180                 185                 190
Tyr Gly Ala Asn Leu Asp Trp Ala Gly Lys Leu Ile Glu Arg Ala Thr
                195                 200                 205
Gly Val Asp Leu Glu Glu Phe Met Gln Lys Asn Ile Cys Glu Pro Leu
                210                 215                 220
Gly Ile Thr Asp Met Thr Phe Lys Leu Gln Gln Arg Pro Asp Met Leu
225                 230                 235                 240
Ala Arg Arg Ser Asp Gln Thr Arg Asn Glu Asn Gly Ser Leu Arg
                245                 250                 255
Tyr Asp Asp Ser Val Tyr Phe Arg His Asp Gly Glu Glu Cys Phe Gly
                260                 265                 270
Gly Gln Gly Val Phe Cys Gly Pro Glu Ser Tyr Met Lys Val Leu Asn
                275                 280                 285
Ser Leu Met Lys His Asp Gly Leu Leu Leu Lys Lys Asp Thr Ile Glu
                290                 295                 300
Leu Met Phe Gln Pro Ala Leu Asp Ala Glu Leu Glu Lys Lys Met Asn
305                 310                 315                 320
Asp His Met Asp Thr Thr Pro His Ile Asn Tyr Gly Ala Ala Leu Pro
                325                 330                 335
Pro Val Met Arg Arg Asn Phe Gly Leu Gly Gly Ile Ile Ala Met Gly
                340                 345                 350
Asp Leu Asp Gly His Asn Trp Arg Arg Glu Gly Ser Leu Thr Phe Gly
                355                 360                 365
Gly Gly Pro Asn Ile Val Trp Gln Ile Asp Pro Thr Val Gly Leu Cys
                370                 375                 380
Thr Leu Val Val Phe Gln Leu Glu Pro Trp Asn Asp Pro Ile Cys Lys
385                 390                 395                 400
Asp Leu Thr Arg Lys Phe Glu Lys Ala Met Tyr Ser Gln Val Lys Cys
                405                 410                 415
Arg Asn

<210> SEQ ID NO 3
<211> LENGTH: 2532
```

<212> TYPE: PRT
<213> ORGANISM: Aspergillus terreus

<400> SEQUENCE: 3

Met Thr Pro Leu Asp Ala Pro Gly Ala Pro Ala Pro Ile Ala Met Val
1               5                   10                  15

Gly Met Gly Cys Arg Phe Gly Gly Ala Thr Asp Pro Gln Lys Leu
            20                  25                  30

Trp Lys Leu Leu Glu Glu Gly Gly Ser Ala Trp Ser Lys Ile Pro Pro
        35                  40                  45

Ser Arg Phe Asn Val Gly Gly Val Tyr His Pro Asn Gly Gln Arg Val
        50                  55                  60

Gly Ser Met His Val Arg Gly Gly His Phe Leu Asp Glu Asp Pro Ala
65                  70                  75                  80

Leu Phe Asp Ala Ser Phe Phe Asn Met Ser Thr Glu Val Ala Ser Cys
                85                  90                  95

Met Asp Pro Gln Tyr Arg Leu Ile Leu Glu Val Val Tyr Glu Ala Leu
            100                 105                 110

Glu Ala Ala Gly Ile Pro Leu Glu Gln Val Ser Gly Ser Lys Thr Gly
            115                 120                 125

Val Phe Ala Gly Thr Met Tyr His Asp Tyr Gln Gly Ser Phe Gln Arg
130                 135                 140

Gln Pro Glu Ala Leu Pro Arg Tyr Phe Ile Thr Gly Asn Ala Gly Thr
145                 150                 155                 160

Met Leu Ala Asn Arg Val Ser His Phe Tyr Asp Leu Arg Gly Pro Ser
                165                 170                 175

Val Ser Ile Asp Thr Ala Cys Ser Thr Thr Leu Thr Ala Leu His Leu
            180                 185                 190

Ala Ile Gln Ser Leu Arg Ala Gly Glu Ser Asp Met Ala Ile Val Ala
            195                 200                 205

Gly Ala Asn Leu Leu Leu Asn Pro Asp Val Phe Thr Thr Met Ser Asn
210                 215                 220

Leu Gly Phe Leu Ser Ser Asp Gly Ile Ser Tyr Ser Phe Asp Ser Arg
225                 230                 235                 240

Ala Asp Gly Tyr Gly Arg Gly Glu Gly Val Ala Ala Ile Val Leu Lys
                245                 250                 255

Thr Leu Pro Asp Ala Val Arg Asp Gly Asp Pro Ile Arg Leu Ile Val
            260                 265                 270

Arg Glu Thr Ala Ile Asn Gln Asp Gly Arg Thr Pro Ala Ile Ser Thr
            275                 280                 285

Pro Ser Gly Glu Ala Gln Glu Cys Leu Ile Gln Asp Cys Tyr Gln Lys
290                 295                 300

Ala Gln Leu Asp Pro Lys Gln Thr Ser Tyr Val Glu Ala His Gly Thr
305                 310                 315                 320

Gly Thr Arg Ala Gly Asp Pro Leu Glu Leu Ala Val Ile Ser Ala Ala
                325                 330                 335

Phe Pro Gly Gln Gln Ile Gln Val Gly Ser Val Lys Ala Asn Ile Gly
            340                 345                 350

His Thr Glu Ala Val Ser Gly Leu Ala Ser Leu Ile Lys Val Ala Leu
            355                 360                 365

Ala Val Glu Lys Gly Val Ile Pro Pro Asn Ala Arg Phe Leu Gln Pro
370                 375                 380

Ser Lys Lys Leu Leu Lys Asp Thr His Ile Gln Ile Pro Leu Cys Ser
385                 390                 395                 400

```
Gln Ser Trp Ile Pro Thr Asp Gly Val Arg Arg Ala Ser Ile Asn Asn
                405                 410                 415
Phe Gly Phe Gly Gly Ala Asn Ala His Ala Ile Val Glu Gln Tyr Gly
            420                 425                 430
Pro Phe Ala Glu Thr Ser Ile Cys Pro Pro Asn Gly Tyr Ser Gly Asn
            435                 440                 445
Tyr Asp Gly Asn Leu Gly Thr Asp Gln Ala His Ile Tyr Val Leu Ser
        450                 455                 460
Ala Lys Asp Glu Asn Ser Cys Met Arg Met Val Ser Arg Leu Cys Asp
465                 470                 475                 480
Tyr Ala Thr His Ala Arg Pro Ala Asp Asp Leu Gln Leu Leu Ala Asn
                485                 490                 495
Ile Ala Tyr Thr Leu Gly Ser Arg Arg Ser Asn Phe Arg Trp Lys Ala
                500                 505                 510
Val Cys Thr Ala His Ser Leu Thr Gly Leu Ala Gln Asn Leu Ala Gly
            515                 520                 525
Glu Gly Met Arg Pro Ser Lys Ser Ala Asp Gln Val Arg Leu Gly Trp
        530                 535                 540
Val Phe Thr Gly Gln Gly Ala Gln Trp Phe Ala Met Gly Arg Glu Leu
545                 550                 555                 560
Ile Glu Met Tyr Pro Val Phe Lys Glu Ala Leu Leu Glu Cys Asp Gly
                565                 570                 575
Tyr Ile Lys Glu Met Gly Ser Thr Trp Ser Ile Ile Glu Glu Leu Ser
                580                 585                 590
Arg Pro Glu Thr Glu Ser Arg Val Asp Gln Ala Glu Phe Ser Leu Pro
            595                 600                 605
Leu Ser Thr Ala Leu Gln Ile Ala Leu Val Arg Leu Leu Trp Ser Trp
        610                 615                 620
Asn Ile Gln Pro Val Ala Val Thr Ser His Ser Ser Gly Glu Ala Ala
625                 630                 635                 640
Ala Ala Tyr Ala Ile Gly Ala Leu Thr Ala Arg Ser Ala Ile Gly Ile
                645                 650                 655
Ser Tyr Ile Arg Gly Ala Leu Thr Ala Arg Asp Arg Leu Ala Ser Val
                660                 665                 670
His Lys Gly Gly Met Leu Ala Val Gly Leu Ser Arg Ser Glu Val Gly
            675                 680                 685
Ile Tyr Ile Arg Gln Val Pro Leu Gln Ser Glu Glu Cys Leu Val Val
        690                 695                 700
Gly Cys Val Asn Ser Pro Ser Ser Val Thr Val Ser Gly Asp Leu Ser
705                 710                 715                 720
Ala Ile Ala Lys Leu Glu Glu Leu Leu His Ala Asp Arg Ile Phe Ala
                725                 730                 735
Arg Arg Leu Lys Val Thr Gln Ala Phe His Ser Ser His Met Asn Ser
            740                 745                 750
Met Thr Asp Ala Phe Arg Ala Gly Leu Thr Glu Leu Phe Gly Ala Asp
            755                 760                 765
Pro Ser Asp Ala Ala Asn Ala Ser Lys Asp Val Ile Tyr Ala Ser Pro
        770                 775                 780
Arg Thr Gly Ala Arg Leu His Asp Met Asn Arg Leu Arg Asp Pro Ile
785                 790                 795                 800
His Trp Val Glu Cys Met Leu His Pro Val Glu Phe Glu Ser Ala Phe
                805                 810                 815
```

```
Arg Arg Met Cys Leu Asp Glu Asn Asp His Met Pro Lys Val Asp Arg
        820                 825                 830

Val Ile Glu Ile Gly Pro His Gly Ala Leu Gly Gly Pro Ile Lys Gln
    835                 840                 845

Ile Met Gln Leu Pro Glu Leu Ala Thr Cys Asp Ile Pro Tyr Leu Ser
850                 855                 860

Cys Leu Ser Arg Gly Lys Ser Ser Leu Ser Thr Leu Arg Leu Leu Ala
865                 870                 875                 880

Ser Glu Leu Ile Arg Ala Gly Phe Pro Val Asp Leu Asn Ala Ile Asn
                885                 890                 895

Phe Pro Arg Gly Cys Glu Ala Ala Arg Val Gln Val Leu Ser Asp Leu
            900                 905                 910

Pro Pro Tyr Pro Trp Asn His Glu Thr Arg Tyr Trp Lys Glu Pro Arg
        915                 920                 925

Ile Ser Gln Ser Ala Arg Gln Arg Lys Gly Pro Val His Asp Leu Ile
    930                 935                 940

Gly Leu Gln Glu Pro Leu Asn Leu Pro Leu Ala Arg Ser Trp His Asn
945                 950                 955                 960

Val Leu Arg Val Ser Asp Leu Pro Trp Leu Arg Asp His Val Val Gly
                965                 970                 975

Ser His Ile Val Phe Pro Gly Ala Gly Phe Val Cys Met Ala Val Met
            980                 985                 990

Gly Ile Ser Thr Leu Cys Ser Ser  Asp His Glu Ser Asp  Asp Ile Ser
        995                 1000                1005

Tyr Ile Leu Arg Asp Val Asn  Phe Ala Gln Ala Leu  Ile Leu Pro
    1010                1015                1020

Ala Asp  Gly Glu Glu Gly Ile  Asp Leu Arg Leu Thr  Ile Cys Ala
    1025                1030                1035

Pro Asp  Gln Ser Leu Gly Ser  Gln Asp Trp Gln Arg  Phe Leu Val
    1040                1045                1050

His Ser  Ile Thr Ala Asp Lys  Asn Asp Trp Thr Glu  His Cys Thr
    1055                1060                1065

Gly Leu  Val Arg Ala Glu Met  Asp Gln Pro Pro Ser  Ser Leu Ser
    1070                1075                1080

Asn Gln  Gln Arg Ile Asp Pro  Arg Pro Trp Ser Arg  Lys Thr Ala
    1085                1090                1095

Pro Gln  Glu Leu Trp Asp Ser  Leu His Arg Val Gly  Ile Arg His
    1100                1105                1110

Gly Pro  Phe Phe Arg Asn Ile  Thr Cys Ile Glu Ser  Asp Gly Arg
    1115                1120                1125

Gly Ser  Trp Cys Thr Phe Ala  Ile Ala Asp Thr Ala  Ser Ala Met
    1130                1135                1140

Pro His  Ala Tyr Glu Ser Gln  His Ile Val His Pro  Thr Thr Leu
    1145                1150                1155

Asp Ser  Ala Val Gln Ala Ala  Tyr Thr Thr Leu Pro  Phe Ala Gly
    1160                1165                1170

Ser Arg  Ile Lys Ser Ala Met  Val Pro Ala Arg Val  Gly Cys Met
    1175                1180                1185

Lys Ile  Ser Ser Arg Leu Ala  Asp Leu Glu Ala Arg  Asp Met Leu
    1190                1195                1200

Arg Ala  Gln Ala Lys Met His  Ser Gln Ser Pro Ser  Ala Leu Val
    1205                1210                1215

Thr Asp  Val Ala Val Phe Asp  Glu Ala Asp Pro Val  Gly Gly Pro
```

```
                1220              1225              1230

Val Met Glu Leu Glu Gly Leu Val Phe Gln Ser Leu Gly Ala Ser
    1235              1240              1245

Leu Gly Thr Ser Asp Arg Asp Ser Thr Asp Pro Gly Asn Thr Cys
    1250              1255              1260

Ser Ser Trp His Trp Ala Pro Asp Ile Ser Leu Val Asn Pro Gly
    1265              1270              1275

Trp Leu Glu Lys Thr Leu Gly Thr Gly Ile Gln Glu His Glu Ile
    1280              1285              1290

Ser Leu Ile Leu Glu Leu Arg Arg Cys Ser Val His Phe Ile Gln
    1295              1300              1305

Glu Ala Met Glu Ser Leu Ser Val Gly Asp Val Glu Arg Leu Ser
    1310              1315              1320

Gly His Leu Ala Lys Phe Tyr Ala Trp Met Gln Lys Gln Leu Ala
    1325              1330              1335

Cys Ala Gln Asn Gly Glu Leu Gly Pro Glu Ser Ser Ser Trp Thr
    1340              1345              1350

Arg Asp Ser Glu Gln Ala Arg Cys Ser Leu Arg Ser Arg Val Val
    1355              1360              1365

Ala Gly Ser Thr Asn Gly Glu Met Ile Cys Arg Leu Gly Ser Val
    1370              1375              1380

Leu Pro Ala Ile Leu Arg Arg Glu Val Asp Pro Leu Glu Val Met
    1385              1390              1395

Met Asp Gly His Leu Leu Ser Arg Tyr Tyr Val Asp Ala Leu Lys
    1400              1405              1410

Trp Ser Arg Ser Asn Ala Gln Ala Ser Glu Leu Val Arg Leu Cys
    1415              1420              1425

Cys His Lys Asn Pro Arg Ala Arg Ile Leu Glu Ile Gly Gly Gly
    1430              1435              1440

Thr Gly Gly Cys Thr Gln Leu Val Val Asp Ser Leu Gly Pro Asn
    1445              1450              1455

Pro Pro Val Gly Arg Tyr Asp Phe Thr Asp Val Ser Ala Gly Phe
    1460              1465              1470

Phe Glu Ala Ala Arg Lys Arg Phe Ala Gly Trp Gln Asn Val Met
    1475              1480              1485

Asp Phe Arg Lys Leu Asp Ile Glu Asp Asp Pro Glu Ala Gln Gly
    1490              1495              1500

Phe Val Cys Gly Ser Tyr Asp Val Val Leu Ala Cys Gln Val Leu
    1505              1510              1515

His Ala Thr Ser Asn Met Gln Arg Thr Leu Thr Asn Val Arg Lys
    1520              1525              1530

Leu Leu Lys Pro Gly Gly Lys Leu Ile Leu Val Glu Thr Thr Arg
    1535              1540              1545

Asp Glu Leu Asp Leu Phe Phe Thr Phe Gly Leu Leu Pro Gly Trp
    1550              1555              1560

Trp Leu Ser Glu Glu Pro Glu Arg Gln Ser Thr Pro Ser Leu Ser
    1565              1570              1575

Pro Thr Met Trp Arg Ser Met Leu His Thr Thr Gly Phe Asn Gly
    1580              1585              1590

Val Glu Val Glu Ala Arg Asp Cys Asp Ser His Glu Phe Tyr Met
    1595              1600              1605

Ile Ser Thr Met Met Ser Thr Ala Val Gln Ala Thr Pro Met Ser
    1610              1615              1620
```

-continued

```
Cys Ser Val Lys Leu Pro Glu Val Leu Val Tyr Val Asp Ser
1625                1630                1635

Ser Thr Pro Met Ser Trp Ile Ser Asp Leu Gln Gly Glu Ile Arg
1640                1645                1650

Gly Arg Asn Cys Ser Val Thr Ser Leu Gln Ala Leu Arg Gln Val
1655                1660                1665

Pro Pro Thr Glu Gly Gln Ile Cys Val Phe Leu Gly Glu Val Glu
1670                1675                1680

His Ser Met Leu Gly Ser Val Thr Asn Asp Asp Phe Thr Leu Leu
1685                1690                1695

Thr Ser Met Leu Gln Leu Ala Gly Gly Thr Leu Trp Val Thr Gln
1700                1705                1710

Gly Ala Thr Met Lys Ser Asp Asp Pro Leu Lys Ala Leu His Leu
1715                1720                1725

Gly Leu Leu Arg Thr Met Arg Asn Glu Ser His Gly Lys Arg Phe
1730                1735                1740

Val Ser Leu Asp Leu Asp Pro Ser Arg Asn Pro Trp Thr Gly Asp
1745                1750                1755

Ser Arg Asp Ala Ile Val Ser Val Leu Asp Leu Ile Ser Met Ser
1760                1765                1770

Asp Glu Lys Glu Phe Asp Tyr Ala Glu Arg Asp Gly Val Ile His
1775                1780                1785

Val Pro Arg Ala Phe Ser Asp Ser Ile Asn Gly Gly Glu Glu Asp
1790                1795                1800

Gly Tyr Ala Leu Glu Pro Phe Gln Asp Ser Gln His Leu Leu Arg
1805                1810                1815

Leu Asp Ile Gln Thr Pro Gly Leu Leu Asp Ser Leu His Phe Thr
1820                1825                1830

Lys Arg Asn Val Asp Thr Tyr Glu Pro Asp Lys Leu Pro Asp Asp
1835                1840                1845

Trp Val Glu Ile Glu Pro Arg Ala Phe Gly Leu Asn Phe Arg Asp
1850                1855                1860

Ile Met Val Ala Met Gly Gln Leu Glu Ser Asn Val Met Gly Phe
1865                1870                1875

Glu Cys Ala Gly Val Val Thr Ser Leu Ser Glu Thr Ala Arg Thr
1880                1885                1890

Ile Ala Pro Gly Leu Ala Val Gly Asp Arg Val Cys Ala Leu Met
1895                1900                1905

Asn Gly His Trp Ala Ser Arg Val Thr Thr Ser Arg Thr Asn Val
1910                1915                1920

Val Arg Ile Pro Glu Thr Leu Ser Phe Pro His Ala Ala Ser Ile
1925                1930                1935

Pro Leu Ala Phe Thr Thr Ala Tyr Ile Ser Leu Tyr Thr Val Ala
1940                1945                1950

Arg Ile Leu Pro Gly Glu Thr Val Leu Ile His Ala Gly Ala Gly
1955                1960                1965

Gly Val Gly Gln Ala Ala Ile Ile Leu Ala Gln Leu Thr Gly Ala
1970                1975                1980

Glu Val Phe Thr Thr Ala Gly Ser Glu Thr Lys Arg Asn Leu Leu
1985                1990                1995

Ile Asp Lys Phe His Leu Asp Pro Asp His Val Phe Ser Ser Arg
2000                2005                2010
```

```
Asp Ser Ser Phe Val Asp Gly Ile Lys Thr Arg Thr Arg Gly Lys
    2015                2020                2025

Gly Val Asp Val Val Leu Asn Ser Leu Ala Gly Pro Leu Leu Gln
2030                2035                2040

Lys Ser Phe Asp Cys Leu Ala Arg Phe Gly Arg Phe Val Glu Ile
2045                2050                2055

Gly Lys Lys Asp Leu Glu Gln Asn Ser Arg Leu Asp Met Ser Thr
2060                2065                2070

Phe Val Arg Asn Val Ser Phe Ser Ser Val Asp Ile Leu Tyr Trp
2075                2080                2085

Gln Gln Ala Lys Pro Ala Glu Ile Phe Gln Ala Met Ser Glu Val
2090                2095                2100

Ile Leu Leu Trp Glu Arg Thr Ala Ile Gly Leu Ile His Pro Ile
2105                2110                2115

Ser Glu Tyr Pro Met Ser Ala Leu Glu Lys Ala Phe Arg Thr Met
2120                2125                2130

Gln Ser Gly Gln His Val Gly Lys Ile Val Val Thr Val Ala Pro
2135                2140                2145

Asp Asp Ala Val Leu Val Arg Gln Glu Arg Met Pro Leu Phe Leu
2150                2155                2160

Lys Pro Asn Val Ser Tyr Leu Val Ala Gly Gly Leu Gly Gly Ile
2165                2170                2175

Gly Arg Arg Ile Cys Glu Trp Leu Val Asp Arg Gly Ala Arg Tyr
2180                2185                2190

Leu Ile Ile Leu Ser Arg Thr Ala Arg Val Asp Pro Val Val Thr
2195                2200                2205

Ser Leu Gln Glu Arg Gly Cys Thr Val Ser Val Gln Ala Cys Asp
2210                2215                2220

Val Ala Asp Glu Ser Gln Leu Glu Ala Ala Leu Gln Gln Cys Arg
2225                2230                2235

Ala Glu Glu Met Pro Pro Ile Arg Gly Val Ile Gln Gly Ala Met
2240                2245                2250

Val Leu Lys Asp Ala Leu Val Ser Gln Met Thr Ala Asp Gly Phe
2255                2260                2265

His Ala Ala Leu Arg Pro Lys Val Gln Gly Ser Trp Asn Leu His
2270                2275                2280

Arg Ile Ala Ser Asp Val Asp Phe Phe Val Met Leu Ser Ser Leu
2285                2290                2295

Val Gly Val Met Gly Gly Ala Gly Gln Ala Asn Tyr Ala Ala Ala
2300                2305                2310

Gly Ala Phe Gln Asp Ala Leu Ala Glu His Arg Met Ala His Asn
2315                2320                2325

Gln Pro Ala Val Thr Ile Asp Leu Gly Met Val Gln Ser Ile Gly
2330                2335                2340

Tyr Val Ala Glu Thr Asp Ser Ala Val Ala Glu Arg Leu Gln Arg
2345                2350                2355

Ile Gly Tyr Gln Pro Leu His Glu Glu Glu Val Leu Asp Val Leu
2360                2365                2370

Glu Gln Ala Ile Ser Pro Val Cys Ser Pro Ala Ala Pro Thr Arg
2375                2380                2385

Pro Ala Val Ile Val Thr Gly Ile Asn Thr Arg Pro Gly Pro His
2390                2395                2400

Trp Ala His Ala Asp Trp Met Gln Glu Ala Arg Phe Ala Gly Ile
```

```
            2405                2410                2415

Lys Tyr Arg Asp Pro Leu Arg Asp Asn His Gly Ala Leu Ser Leu
    2420                2425                2430

Thr Pro Ala Glu Asp Asp Asn Leu His Ala Arg Leu Asn Arg Ala
    2435                2440                2445

Ile Ser Gln Gln Glu Ser Ile Ala Val Ile Met Glu Ala Met Ser
    2450                2455                2460

Cys Lys Leu Ile Ser Met Phe Gly Leu Thr Asp Ser Glu Met Ser
2465                2470                2475

Ala Thr Gln Thr Leu Ala Gly Ile Gly Val Asp Ser Leu Val Ala
    2480                2485                2490

Ile Glu Leu Arg Asn Trp Ile Thr Ala Lys Phe Asn Val Asp Ile
    2495                2500                2505

Ser Val Phe Glu Leu Met Glu Gly Arg Thr Ile Ala Lys Val Ala
    2510                2515                2520

Glu Val Val Leu Gln Arg Tyr Lys Ala
    2525                2530

<210> SEQ ID NO 4
<211> LENGTH: 256
<212> TYPE: PRT
<213> ORGANISM: Escherichia coli

<400> SEQUENCE: 4

Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
                20                  25                  30

Asp Glu Glu Leu Ser Ser His Phe Thr Leu His Leu Val Asp Leu Pro
            35                  40                  45

Gly Phe Gly Arg Ser Arg Gly Phe Gly Ala Leu Ser Leu Ala Asp Met
        50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110

Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240
```

His Pro Ala Glu Phe Cys His Leu Leu Val Ala Leu Lys Gln Arg Val
                245                 250                 255

<210> SEQ ID NO 5
<211> LENGTH: 1242
<212> TYPE: DNA
<213> ORGANISM: Aspergillus terreus

<400> SEQUENCE: 5

```
atgggatcca tcattgatgc tgctgcggca gcggatccgg ttgttctgat ggaaaccgcc      60
ttccgcaagg ccgtgaaatc caggcagatc cccggggcgg tcatcatggc ccgagattgc     120
agtggcaatc taaattatac gcgctgcttc ggggctcgga cggtgcgacg ggacgagtgc     180
aatcagctgc cgccgctaca ggtcgacacc ccctgccggc tcgccagtgc gaccaagctg     240
ctgaccacga tcatggccct acaatgcatg gagcgcggtc tcgtggactt ggatgagacg     300
gtggataggc tgcttccgga tttgagcgcg atgcccgtgc tggaggggtt tgacgacgcg     360
ggaaacgcaa gattgcgaga gcgtcggggg aagatcacgc tgcggcacct gctgacgcat     420
acatcgggac tgtcgtacgt cttcctccat ccgttgctcc gggaatacat ggcccagggc     480
cacctccagt cggcagaaaa gtttggcatc cagagtcgcc tggcgccgcc ggccgtcaac     540
gaccctgggg cggagtggat ctacggcgcc aacctggact gggcgggtaa gctcgtcgag     600
cgggccaccg gcctcgacct ggagcagtac ctgcaggaga atatctgtgc gccgctgggc     660
atcaccgaca tgacctttaa gctgcagcaa cggccggata tgcttgcgcg ccgggccgac     720
caaacgcacc gcaactcggc ggatgggcgc ctgcgctacg acgactcggt ctacttccgg     780
gccgatggag aggagtgctt cggcggccag ggggtgttct cgggccctgg gtcctatatg     840
aaggtgcttc actcgctgtt gaagcgagac gggctcctgc tgcagccaca gaccgtggac     900
ttgatgtttc agcctgccct cgagccgcga ctcgaagagc agatgaacca gcacatggac     960
gccagcccac atatcaacta cggtgggccg atgcccatgg tccttcgtcg cagctttggg    1020
ctgggggga tcatcgcctt ggaggatctg gacggagaga actggcgccg aaaaggttcc    1080
ttgacctttg ggggtggccc aaacattgtg tggcaaatcg accccaaagc cggcctgtgc    1140
acccttgcgt tcttccaact ggaaccctgg aatgacccgg tctgtcgtga tctgacacgc    1200
acattcgagc atgccatcta tgcgcagtac cagcagggtt aa                      1242
```

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcatggccc gagatgctag cggcaatcta aattat                                 36

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctaaattat acgcgtgcct cggggctcg gac                                     33

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgcgacggg acgaggccaa tcaattgccg ccgctacagg tc                         42

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caggtcgaca cccccgcccg gctcgccagt gc                                    32

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcatggccct acaagccatg gagcgcggtc tc                                    32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgcaggaga atatcgctgc gccgctgggc at                                    32

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccgatggag aggaggcctt cggcggccag g                                     31

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccaaagccg gcctggccac ccttgcgttc tt                                    32

```
<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggaatgacc cggtcgctcg tgatctgaca cg                                    32

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtcatcatg gcccgagatt ccagtggcaa tctaaattat a                          41

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacggtgcga cgggacgagt ccaatcagct gccgccgcta c                          41

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cggtcatcat ggcccgagat actagtggca atctaaatta tac                        43

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggacggtgcg acgggacgag accaatcagc tgccgccgct ac                         42

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cggtcatcat ggcccgagat aacagtggca atctaaatta ta                         42

<210> SEQ ID NO 20
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggacggtgcg acgggacgag aacaatcagc tgccgccgct ac                        42

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggtcatcat ggcccgagat cagagtggca atctaaatta tac                       43

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggacggtgcg acgggacgag cagaatcagc tgccgccgct aca                       43

<210> SEQ ID NO 23
<211> LENGTH: 377
<212> TYPE: PRT
<213> ORGANISM: Burkholderia gladioli

<400> SEQUENCE: 23

Ala Ala Ser Leu Ala Ala Arg Leu Asp Ala Val Phe Asp Gln Ala Leu
1               5                   10                  15

Arg Glu Arg Arg Leu Val Gly Ala Val Ala Ile Val Ala Arg His Gly
            20                  25                  30

Glu Ile Leu Tyr Arg Arg Ala Gln Gly Leu Ala Asp Arg Glu Ala Gly
        35                  40                  45

Arg Pro Met Arg Glu Asp Thr Leu Phe Arg Leu Ala Ser Val Thr Lys
    50                  55                  60

Pro Ile Val Ala Leu Ala Val Leu Arg Leu Val Ala Arg Gly Glu Leu
65                  70                  75                  80

Ala Leu Asp Ala Pro Val Thr Arg Trp Leu Pro Glu Phe Arg Pro Arg
                85                  90                  95

Leu Ala Asp Gly Ser Glu Pro Leu Val Thr Ile His His Leu Leu Thr
            100                 105                 110

His Thr Ser Gly Leu Gly Tyr Trp Leu Leu Glu Gly Ala Gly Ser Val
        115                 120                 125

Tyr Asp Arg Leu Gly Ile Ser Asp Gly Ile Asp Leu Arg Asp Phe Asp
    130                 135                 140

Leu Asp Glu Asn Leu Arg Arg Leu Ala Ser Ala Pro Leu Ser Phe Ala
145                 150                 155                 160

Pro Gly Ser Gly Trp Gln Tyr Ser Leu Ala Leu Asp Val Leu Gly Ala
                165                 170                 175

Val Val Glu Arg Ala Thr Gly Gln Pro Leu Ala Ala Ala Val Asp Ala
```

-continued

```
            180                 185                 190
Leu Val Ala Gln Pro Leu Gly Met Arg Asp Cys Gly Phe Val Ser Ala
        195                 200                 205

Glu Pro Glu Arg Phe Ala Val Pro Tyr His Asp Gly Gln Pro Glu Pro
    210                 215                 220

Val Arg Met Arg Asp Gly Ile Glu Val Pro Leu Pro Glu Gly His Gly
225                 230                 235                 240

Ala Ala Val Arg Phe Ala Pro Ser Arg Val Phe Glu Pro Gly Ala Tyr
                245                 250                 255

Pro Ser Gly Gly Ala Gly Met Tyr Gly Ser Ala Asp Asp Val Leu Arg
            260                 265                 270

Ala Leu Glu Ala Ile Arg Ala Asn Pro Gly Phe Leu Pro Glu Thr Leu
        275                 280                 285

Ala Asp Ala Ala Arg Arg Asp Gln Ala Gly Val Gly Ala Glu Thr Arg
    290                 295                 300

Gly Pro Gly Trp Gly Phe Gly Tyr Leu Ser Ala Val Leu Asp Asp Pro
305                 310                 315                 320

Ala Ala Ala Gly Thr Pro Gln His Ala Gly Thr Leu Gln Trp Gly Gly
                325                 330                 335

Val Tyr Gly His Ser Trp Phe Val Asp Arg Ala Leu Gly Leu Ser Val
            340                 345                 350

Leu Leu Leu Thr Asn Thr Ala Tyr Glu Gly Met Ser Gly Pro Leu Thr
        355                 360                 365

Ile Ala Leu Arg Asp Ala Val Tyr Ala
    370                 375

<210> SEQ ID NO 24
<211> LENGTH: 4
<212> TYPE: PRT
<213> ORGANISM: Aspergillus terreus
<220> FEATURE:
<221> NAME/KEY: MOD_RES
<222> LOCATION: (2)..(3)
<223> OTHER INFORMATION: Any amino acid

<400> SEQUENCE: 24

Ser Xaa Xaa Lys
1
```